(12) United States Patent
Matranga et al.

(10) Patent No.: US 12,397,012 B2
(45) Date of Patent: Aug. 26, 2025

(54) NUCLEIC ACID THERAPEUTICS FOR GENETIC DISORDERS

(71) Applicant: GreenLight Biosciences, Inc., Medford, MA (US)

(72) Inventors: Christian Matranga, Stow, MA (US); James Robbins Abshire, Cambridge, MA (US); Andrey J. Zarur, Winchester, MA (US); Kelsey A. Haugh, Waltham, MA (US); Katherine J. Williams, Haverhill, MA (US)

(73) Assignee: GreenLight Biosciences, Inc., Medford, MA (US)

( * ) Notice: Subject to any disclaimer, the term of this patent is extended or adjusted under 35 U.S.C. 154(b) by 978 days.

(21) Appl. No.: 17/378,580

(22) Filed: Jul. 16, 2021

(65) Prior Publication Data

US 2022/0096525 A1 Mar. 31, 2022

Related U.S. Application Data

(60) Provisional application No. 63/053,474, filed on Jul. 17, 2020.

(51) Int. Cl.
| | |
|---|---|
| *A61K 31/7115* | (2006.01) |
| *A61K 48/00* | (2006.01) |
| *C12N 15/11* | (2006.01) |

(52) U.S. Cl.
CPC .......... *A61K 31/7115* (2013.01); *A61K 48/00* (2013.01); *C12N 15/11* (2013.01); *C12N 2510/00* (2013.01); *C12N 2800/60* (2013.01); *C12N 2800/70* (2013.01)

(58) Field of Classification Search
None
See application file for complete search history.

(56) References Cited

U.S. PATENT DOCUMENTS

| | | | |
|---|---|---|---|
| 2005/0048652 A1 | 3/2005 | Voytas et al. | |
| 2017/0292138 A1 | 10/2017 | Blake et al. | |
| 2018/0087045 A1 | 3/2018 | Blake et al. | |
| 2019/0144489 A1 | 5/2019 | Cunningham et al. | |

FOREIGN PATENT DOCUMENTS

| | | |
|---|---|---|
| JP | 2005-528912 A | 9/2005 |
| WO | WO 2012/156839 A2 | 11/2012 |
| WO | WO 2013/055905 A1 | 4/2013 |
| WO | WO 2017/083356 A1 | 5/2017 |

OTHER PUBLICATIONS

Collins, et al. (2015) "Gene Therapy: progress and predictions", Proceedings of the Royal Society B, 282: 20143003, 8 pages long. (Year: 2015).*
Kaushik, et al. (2024) "Beyond the optic nerve: Genetics, diagnosis, and promising therapies for glaucoma", Gene, 894: 147983, 12 pages. (Year: 2024).*
Nora, et al. (2018) "The Art of vector engineering: towards the construction of next-generation genetic tools", Microbial biotechnology, 12(1): 125-47. (Year: 2018).*
Ganesan, et al. (2016) "Synthetic RNA-protein modules integrated with native translation mechanisms to control gene expression in malaria parasites", Nature Communications, 7: 10727, 10 pages. (Year: 2016).*
International Search Report and Written Opinion for PCT/US2021/042015 mailed Nov. 11, 2021.
Al Mosabbir et al., Genomic integration occurs in the packaging cell via unexported lentiviral precursors. Biotechnol Lett. Oct. 2016;38(10):1715-21. doi: 10.1007/s10529-016-2164-6. Epub Jun. 24, 2016.
Ansari-Lari et al., Analysis of HIV type 1 reverse transcriptase expression in a human cell line. AIDS Res Hum Retroviruses. Sep. 1994;10(9):1117-24. doi: 10.1089/aid.1994.10.1117.
Anson, D.S., The use of retroviral vectors for gene therapy-what are the risks? A review of retroviral pathogenesis and its relevance to retroviral vector-mediated gene delivery. Genet Vaccines Ther. Aug. 13, 2004;2(1):9. doi: 10.1186/1479-0556-2-9.
Cherepanov et al., High-level expression of active HIV-1 integrase from a synthetic gene in human cells. FASEB J. Jul. 2000;14(10):1389-99. doi: 10.1096/fj.14.10.1389.
Galvis et al., Conformational Changes in the 5' End of the HIV-1 Genome Dependent on the Debranching Enzyme DBR1 during Early Stages of Infection. J Virol. Nov. 14, 2017;91(23):e01377-17. doi: 10.1128/JVI.01377-17.
Groom et al., Rev regulates translation of human immunodeficiency virus type 1 RNAs. J Gen Virol. May 2009;90(Pt 5):1141-1147. doi: 10.1099/vir.0.007963-0. Epub Mar. 4, 2009.
Hughes, S.H., Reverse Transcription of Retroviruses and LTR Retrotransposons. Microbiol Spectr. Apr. 2015;3(2):MDNA3-0027-2014. doi: 10.1128/microbiolspec.MDNA3-0027-2014.
Iwatani et al., Efficient initiation of HIV-1 reverse transcription in vitro. Requirement for RNA sequences downstream of the primer binding site abrogated by nucleocapsid protein-dependent primer-template interactions. J Biol Chem. Apr. 18, 2003;278(16):14185-95. doi: 10.1074/jbc.M211618200. Epub Jan. 30, 2003.

(Continued)

*Primary Examiner* — Robert M Kelly
(74) *Attorney, Agent, or Firm* — Wolf, Greenfield & Sacks, P.C.

(57) ABSTRACT

Provided herein, are compositions based on retroviruses (e.g., lentiviruses) comprising one or more nucleic acid molecules encoding retroviral Pol polyprotein components and a nucleic acid molecule comprising one or more transgene sequences flanked by long terminal repeat sequences, for delivery of the one or more transgenes to a target cell ex vivo or in vivo. The compositions are useful for delivering to a target cell (e.g., hematopoietic stem cells (HSCs), liver cells, ocular cells, muscle cells, epithelial cells, T cells, etc.) and/or stably expressing any transgene (e.g., beta-globin, Factor VIII, RP GTPase regulator (RPGR), dystrophin, cystic fibrosis transmembrane conductance regulator (CFTR), a chimeric antigen receptor, etc.) with a biological effect to treat and/or ameliorate the symptoms associated with any disorder related to gene expression (e.g., sickle cell disease, beta-thalassemia, haemophilia B, retinitis pigmentosa, Duchenne muscular dystrophy, cystic fibrosis, cancer, etc.).

24 Claims, 11 Drawing Sheets

Specification includes a Sequence Listing.

(56) References Cited

OTHER PUBLICATIONS

Karacostas et al., Overexpression of the HIV-1 gag-pol polyprotein results in intracellular activation of HIV-1 protease and inhibition of assembly and budding of virus-like particles. Virology. Apr. 1993;193(2):661-71. doi: 10.1006/viro.1993.1174.

Koh et al., Tuning of mRNA stability through altering 3'-UTR sequences generates distinct output expression in a synthetic circuit driven by p53 oscillations. Sci Rep. Apr. 12, 2019;9(1):5976. doi: 10.1038/s41598-019-42509-y.

Krotova et al., Consensus HIV-1 FSU-A integrase gene variants electroporated into mice induce polyfunctional antigen-specific CD4+ and CD8+ T cells. PLoS One. May 8, 2013;8(5):e62720. doi: 10.1371/journal.pone.0062720.

Maruggi et al., mRNA as a Transformative Technology for Vaccine Development to Control Infectious Diseases. Mol Ther. Apr. 10, 2019;27(4):757-772. doi: 10.1016/j.ymthe.2019.01.020. Epub Feb. 7, 2019.

Mulder et al., Degradation of HIV-1 integrase by the N-end rule pathway. J Biol Chem. Sep. 22, 2000;275(38):29749-53. doi: 10.1074/jbc.M004670200.

Pardi et al., mRNA vaccines—a new era in vaccinology. Nat Rev Drug Discov. Apr. 2018;17(4):261-279. doi: 10.1038/nrd.2017.243. Epub Jan. 12, 2018.

Pardi et al., Nucleoside Modified mRNA Vaccines for Infectious Diseases. Methods Mol Biol. 2017;1499:109-121.

Richardson et al., CRISPR-Cas9 genome editing in human cells occurs via the Fanconi anemia pathway. Nat Genet. Aug. 2018;50(8):1132-1139. doi: 10.1038/s41588-018-0174-0.Epub Jul. 27, 2018.

Sundquist et al., HIV-1 assembly, budding, and maturation. Cold Spring Harb Perspect Med. Jul. 2012;2(7):a006924. doi: 10.1101/cshperspect.a006924. Erratum in: Cold Spring Harb Perspect Med. Aug. 2012;2(8). doi: 10.1101/cshperspect.a015420.

Swanstrom et al., The terminal redundancy of the retrovirus genome facilitates chain elongation by reverse transcriptase. J Biol Chem. Feb. 10, 1981;256(3):1115-21.

Wolff et al., Integrated functional and bioinformatics approach for the identification and experimental verification of RNA signals: application to HIV-1 INS. Nucleic Acids Res. Jun. 1, 2003;31(11):2839-51. doi: 10.1093/nar/gkg390.

Zimmer, G., RNA replicons—a new approach for influenza virus immunoprophylaxis. Viruses. Feb. 2010;2(2):413-34. doi: 10.3390/v2020413. Epub Jan. 29, 2010.

International Preliminary Report on Patentability, mailed Jan. 26, 2023 for International Application No. PCT/US2021/042015.

PCT/US2021/042015, Nov. 11, 2021, International Search Report and Written Opinion.

Li et al., Research progress in quality control analysis methods for gene therapy products. Chin J Pharm Anal. Jan. 25, 2020;40(1):4-12.

* cited by examiner

| | Non-dividing cells* | Genome integration | Expression site | Transgene capacity | Production titer | Major advantages | Major challenge |
|---|---|---|---|---|---|---|---|
| CRISPR/Cas9 | | ✓ | Site-specific | ++ | NA | Gene editing | Edits dividing cells only |
| Retrovirus | | ✓ | Actively transcribed genes | ++ | + | Integration | Edits dividing cells only; potential genotoxicity |
| Lentivirus | ✓ | ✓ | Actively transcribed genes | ++ | ++ | Integration | Potential genotoxicity |
| Herpesvirus | ✓ | | Episomal | +++++ | +++ | Transgene capacity | Dosing requirements |
| Adenovirus | ✓ | | Episomal | +++ | ++++ | Production titer | Dosing requirements |
| AAV | ✓ | | Episomal | + | +++++ | Production titer | Capacity, potency, repeated dosing |

FIG. 2

NUCLEIC ACID THERAPEUTICS FOR GENETIC DISORDERS

RELATED APPLICATION

This application claims the benefit under 35 U.S.C. § 119(e) of U.S. Provisional Application No. 63/053,474, filed Jul. 17, 2020, the content of which is incorporated herein by reference in its entirety.

REFERENCE TO THE SEQUENCE LISTING

The present application is being filed along with a Sequence Listing in electronic format. The Sequence Listing is provided as a file entitled G0830.70039US01-SEQ.txt created on Jul. 16, 2021, which is 75,239 bytes in size. The information in electronic format of the Sequence Listing is incorporated herein by reference in its entirety.

BACKGROUND OF THE INVENTION

Examples of current gene therapy approaches include, but are not limited to, CRISPR-based systems, such as CRISPR/Cas9, retroviruses, lentiviruses, herpesviruses, adenoviruses, and adeno-associated viruses (AAV), as seen in FIG. 2. Although there are many advantages to these various approaches, significant limitations also exist. For example, retroviruses and some CRISPR-based systems generally require cell division and homologous recombination in order to be successful, and therefore, do not function in non-dividing cells. In AAVs, there exists a transgene size limitation, effectively limiting their capacity and usefulness. Other limitations of adenoviruses, include, for example, toxicity associated with high doses due to limited efficacy and a decrease in the effectiveness of repeat dosing due to the immune response to the virus. Moreover, the production of the virus for a therapeutic dose can be quite costly.

As shown in FIG. 2, lentiviruses have previously been used as a model for gene therapy programs. Lentiviruses are ssRNA genome viruses (e.g., HIV) that infect a wide range of hosts and integrate into the genome, sometimes in a latent DNA form. In current gene therapy programs, lentiviral particles are produced using a safer, split construct design. For example, the third-generation design involves gene therapy using four plasmids: a transfer plasmid which carries the gene of interest and integrates into the genome, a packaging plasmid that provides the particle formation, reverse transcription, and integration functions, the envelope plasmid which provides a broad host range, and a plasmid that provides the nuclear export of mRNA. A general limitation of the lentiviral approach is that the production of the virus requires expansion in cells, which is slow and expensive; and the processing of viral particles is inefficient.

Thus, there remains a need for improved gene delivery systems beyond those available today.

SUMMARY OF THE INVENTION

Disclosed herein are nucleic acid compositions for in vivo gene therapy. The compositions include a minimal design which provide transgene-encoding nucleic acid molecules, nucleic acid molecules expressing reverse transcriptase and/or integrase, and can contain auxiliary nucleic acid molecules that support reverse transcription and integration of the transgenes, and can contain a delivery system. The compositions do not require nucleic acid sequences that express proteins encoded by the retroviral rev and env genes. However, the compositions can contain nucleic acid sequences that express one or more proteins encoded by the retroviral rev gene, the retroviral env gene, or both. The invention also provides nucleic acid molecules, methods of use, methods of treatment, nucleic acid templates, cells, and kits. The invention also provides for modifications to increase the stability and/or functioning of the nucleic acid and/or the stability and/or functioning of the encoded protein. These modifications can include mutations in one or more intrinsic instability (INS) elements, a functional unit, such as an integrase, with an N-terminal methionine-glycine dipeptide; fusion of a functional unit, such as an integrase, to a homing protein; use of codon optimization for expression in a host cell; and/or use of a priming oligonucleotide. Other modifications are as disclosed herein.

Some aspects of the invention include one or more nucleic acid molecules encoding one or more Pol polyprotein components flanked by 5' and 3' untranslated regions (UTRs), and a nucleic acid molecule comprising one or more reverse transcriptase priming elements and one or more promoter sequences operably linked to one or more transgenes, between a 5' long terminal repeat (LTR) and a 3' LTR. Some aspects of the invention include one or more nucleic acid molecules encoding one or more of the protein components of the Pol polyprotein flanked by 5' and 3' untranslated regions (UTRs), and a nucleic acid molecule comprising one or more reverse transcriptase priming elements and one or more promoter sequences operably linked to one or more transgenes, between a 5' long terminal repeat (LTR) and a 3' LTR, but do not include nucleic acid sequences that express proteins encoded by at least one of retroviral rev gene and retroviral env gene. Some aspects of the invention include one or more nucleic acid molecules encoding one or more Pol polyprotein components flanked by 5' and 3' untranslated regions (UTRs), and a nucleic acid molecule comprising one or more reverse transcriptase priming elements and one or more promoter sequences operably linked to one or more transgenes, between a 5' long terminal repeat (LTR) and a 3' LTR, but do not include nucleic acid sequences that express proteins encoded by both the retroviral rev and env genes. Some aspects of the invention include one or more nucleic acid molecules encoding one or more Pol polyprotein components flanked by 5' and 3' untranslated regions (UTRs), and a nucleic acid molecule comprising one or more reverse transcriptase priming elements and one or more promoter sequences operably linked to one or more transgenes, between a 5' long terminal repeat (LTR) and a 3' LTR, and are capable of integrating the one or more transgenes into a host genome in the absence of functional retroviral Rev and/or Env proteins. The expression of the Pol polyprotein components does not necessarily require translational slippage from an inline gag gene. The one or more nucleic acid molecules encoding the Pol polyprotein components may be a nucleic acid molecule comprising a 5' UTR, a nucleic acid sequence encoding a Pol polyprotein, and a 3' UTR. Alternatively, the one or more nucleic acid molecules encoding the Pol polyprotein components may be a nucleic acid molecule comprising a 5' UTR, a nucleic acid sequence encoding at least the Pol polyprotein components reverse transcriptase and integrase, and a 3' UTR. The Pol polyprotein components reverse transcriptase and integrase may be expressed on a polycistronic construct. In some embodiments, the polycistronic construct is bicistronic. In some embodiments, the polycistronic construct is tricistronic. The Pol polyprotein components reverse transcriptase and integrase may be expressed with one or more polycistronic elements. The polycistronic element may be an intervening internal ribosome entry site (IRES), a2A peptide-encoding sequence, or other polycistronic element. The one or more nucleic acid molecules encoding the Pol polyprotein components may be two nucleic acid molecules, wherein one of them comprises a 5' UTR, a nucleic acid sequence encoding at least the Pol polyprotein component reverse transcriptase, and a 3' UTR, and the other one comprises a 5' UTR, a nucleic acid sequence encoding at least the Pol polyprotein component integrase, and a 3' UTR. FIGS. 3-5C illustrate exemplary embodiments of some aspects of the invention.

Some aspects of the invention provide a composition that is packaged in a non-viral delivery system, wherein the composition comprises a first RNA molecule that includes a 5' untranslated region (UTR), a nucleic acid sequence encoding a retroviral Pol polyprotein, and a 3' UTR; and a second RNA molecule comprising one or more reverse transcriptase priming elements and one or more promoter sequences operably linked to one or more transgenes, between a 5' long terminal repeat (LTR) and a 3' LTR. Some aspects of the invention provide a composition that is packaged in a non-viral delivery system, wherein the composition comprises a first RNA molecule that includes a 5' untranslated region (UTR), a nucleic acid sequence encoding a retroviral Pol polyprotein, and a 3' UTR; and a second RNA molecule comprising one or more reverse transcriptase priming elements and one or more promoter sequences operably linked to one or more transgenes, between a 5' long terminal repeat (LTR) and a 3' LTR, but does not include nucleic acid sequences that express proteins encoded by at least one of retroviral rev gene and retroviral env gene. Some aspects of the invention provide a composition that is packaged in a non-viral delivery system, wherein the composition comprises a first RNA molecule that includes a 5' untranslated region (UTR), a nucleic acid sequence encoding a retroviral Pol polyprotein, and a 3' UTR; and a second RNA molecule comprising one or more reverse transcriptase priming elements and one or more promoter sequences operably linked to one or more transgenes, between a 5' long terminal repeat (LTR) and a 3' LTR, but does not include nucleic acid sequences that express proteins encoded by both the retroviral rev and env genes. Some aspects of the invention provide a composition that is packaged in a non-viral delivery system, wherein the composition comprises a first RNA molecule that includes a 5' untranslated region (UTR), a nucleic acid sequence encoding a retroviral Pol polyprotein, and a 3' UTR and a second RNA molecule comprising one or more reverse transcriptase priming elements and one or more promoter sequences operably linked to one or more transgenes, between a 5' long terminal repeat (LTR) and a 3' LTR, and that is capable of integrating the one or more transgenes into a host genome in the absence of functional retroviral Rev and/or Env proteins.

In some aspects, the one or more nucleic acid molecules encoding the Pol polyprotein components comprise nucleic acid sequences encoding one or more functional units. In some aspects, the one or more nucleic acid molecules encoding the Pol polyprotein components may also comprise nucleic acid sequences encoding one or more accessory proteins. The one or more accessory protein may be selected from nucleocapsid (NC), capsid protein (CA), matrix protein (MA), p6, viral infectivity factor (Vif), transactivator-of transcription (Tat), negative regulatory factor (Nef), viral protein R (Vpr), and viral protein u (Vpu). In some aspects, the accessory protein may contain one or more mutations. In some aspects, the CA is a mutant CA. In some aspects, the mutant CA has a N74D and/or E45A mutation, with the numbering corresponding to the wild-type HIV-1 capsid protein. In some aspects, the wild-type HIV-1 strain can be NL4-3. In some aspects, the one or more nucleic acid molecules encoding the Pol polyprotein components may also comprise nucleic acid sequences encoding one more Gag polyprotein accessory proteins (i.e., an accessory protein that is a Gag polyprotein component). The one or more accessory proteins may be encoded on the same nucleic acid molecule as the Pol polyprotein components. The one or more accessory proteins may also be expressed with one or more polycistronic elements. The polycistronic element may be an intervening IRES, a 2A peptide-encoding sequence, or other polycistronic element. Alternatively, the one or more accessory proteins may be encoded by one or more nucleic acid molecules different from the nucleic acid molecule encoding the Pol polyprotein components, wherein each nucleic acid molecule comprises a 5' UTR and a 3' UTR. In some embodiments, the Gag polyprotein accessory proteins may be selected from NC, CA, MA, and p6. In some embodiments, the Gag polyprotein accessory proteins may be encoded by the Gag polyprotein. In other embodiments, the one or more nucleic acid molecules encoding the Pol polyprotein components do not encode the Gag polyprotein. In some embodiments, the accessory protein MA is not encoded by any of the nucleic acid molecules. In some embodiments, the one or more nucleic acid molecules encoding the Pol polyprotein components comprises a gag-pol gene. In some embodiments, the gag-pol gene comprises a frameshift mutation. In some embodiments, the frameshift mutation is a single nucleotide insertion or deletion.

Some aspects of the invention provide that the one or more nucleic acid molecules encoding the Pol polyprotein components and/or the accessory proteins are modified to increase the stability of the nucleic acid molecules, and/or to increase the stability of the encoded proteins. In some embodiments, the one or more nucleic acid molecules encoding the Pol polyprotein components and/or the accessory proteins are RNA molecules (e.g., mRNA molecules) and can optionally comprise one or more modifications to increase the stability of the RNA molecules (e.g., mRNA molecules). In some embodiments, the one or more nucleic acid molecules encoding the Pol polyprotein components and/or the accessory proteins are DNA molecules and can optionally comprise one or more modifications to increase the stability of the DNA molecules and/or the corresponding mRNA molecules. In some embodiments, the nucleic acid molecules encoding the one or more Pol polyprotein components and/or the accessory proteins comprise one or more mutations in one or more intrinsic instability (INS) elements. The one or more INS elements may be selected from TAGAT, ATAGA, AAAAG, ATAAA, TTATA, or the like. In some embodiments, a codon in an INS element is mutated to an alternate codon for the same amino acid such that the functional protein sequence is preserved (i.e., a silent mutation) while the INS element is altered or removed. In some embodiments, the one or more nucleic acid molecules encoding the one or more Pol polyprotein components encode an integrase polypeptide comprising an N-terminal methionine-glycine dipeptide. In some embodiments, the nucleic acid molecule encoding the one or more Pol polyprotein components encodes the methionine-glycine dipeptide at the 5' end, and in some embodiments the nucleic acid molecule encoding the one or more Pol polyprotein components encodes the methionine-glycine dipeptide internally.

Some aspects of the invention provide that the one or more Pol polyprotein components (e.g., integrase) are fused to a homing protein, which can direct the component, such as integrase, to a specific sequence in the host cell. In some embodiments the homing protein recognizes a palindromic sequence, and in some embodiments, the homing protein recognizes a restriction site. In some embodiments the homing protein is a restriction enzyme. In some embodiments the restriction enzyme is I-PpoI. In some embodiments the homing protein is a nuclease-inactivated restriction enzyme. In some embodiments, the homing protein is I-PpoI N119A.

Some aspects of the invention provide for increased translations in host cells. e.g., by providing that the one or more nucleic acid molecules of the composition are codon optimized for expression in the host cell. In some aspects, the host cell is a mammalian cell. In some aspects, the host cell is a human cell. In some aspects, the host cell is an avian cell.

Some aspects of the invention provide that the composition further comprises a priming oligonucleotide. In some embodiments, the priming oligonucleotide is GUCCCU-GUUCGGGCGCCA (SEQ ID NO: 18) or GTCCCTGTTCGGGCGCCA (SEQ ID NO: 19). In some embodiments, the priming oligonucleotide may be an engineered sequence that is complementary to a reverse transcriptase priming element.

Some aspects of the invention provide that the nucleic acid molecules are RNA molecules or DNA molecules. For example, the nucleic acid molecules may be ssDNA molecules, dsDNA molecules, ssRNA molecules, or dsRNA molecules.

Some aspects of the invention provide that the nucleic acid molecule comprising the one or more transgenes can comprise two or more transgenes, where the transgenes are separated by one or more polycistronic elements. The polycistronic elements may be one or more IRESes and/or one or more sequences encoding a 2A peptide and/or other polycistronic elements. This nucleic acid molecule may comprise one or more enhancers. For example, the one or more enhancers may include a woodchuck hepatitis virus post-transcriptional regulatory element (WPRE).

Some aspects of the invention provide that the nucleic acid molecules are RNA molecules and comprise one or more modifications selected from modified ribonucleosides, a 5'-7mG cap structure, and a poly (rA) tail. In some embodiments, the modified ribonucleoside is pseudouridine or a derivative of pseudouridine (e.g., N1-methylpseudouridine). In some embodiments, the modified ribonucleoside is N6-methyladenosine. In other embodiments, the nucleic acid molecule comprising the one or more transgenes can be an RNA molecule and further comprise one or more modifications selected from a 5'-7mG cap structure and a poly (rA) tail.

Some aspects of the invention include that the Pol polyprotein components, accessory proteins, and/or LTRs are based on Pol polyprotein components, accessory proteins, and/or LTRs are from human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), bovine immunodeficiency virus (BIV), human foamy virus (HFV), murine leukemia virus (MLV), Moloney murine leukemia virus (MoLV), Friend virus (FV), Abelson murine leukemia virus (A-MLV), murine stem cell virus (MSCV), mouse mammary tumor virus (MMTV), Moloney murine sarcoma virus (MoMSV), Rous sarcoma virus (RSV), Fujinami sarcoma virus (FuSV), FBR murine osteosarcoma virus (FBR MSV), Avian myelocytomatosis virus-29 (MC29), Avian erythroblastosis virus (AEV), human T-cell leukemia virus (HTLV), Friend MLV (FrMLV), Avian sarcoma virus (ASV), Avian leukosis virus, Avian myeloblastosis virus, UR2 sarcoma virus. Y73 sarcoma virus, Jaagsiekte sheep retrovirus, Langur virus, Mason-pfizer monkey virus. Squirrel monkey retrovirus, Avian carcinoma mill hill virus 2, Bovine leukemia virus, Primate T-lymphotropic virus 1, Primate T-lymphotropic virus 2. Primate T-lymphotropic virus 3, Walleye dermal sarcoma virus, Walleye epidermal hyperplasia virus 1. Walleye epidermal hyperplasia virus 2, Chick syncytial virus, Feline leukemia virus, Finkel-Biskis-Jinkins murine sarcoma virus, Gardner-Amstein feline sarcoma virus, Gibbon ape leukemia virus, Guinea pig type-C oncovirus. Hardy-Zuckerman feline sarcoma virus, Harvey murine sarcoma virus, Kirsten murine sarcoma virus, Koala retrovirus, Moloney murine sarcoma virus, Porcine type-C oncovirus, Reticuloendotheliosis virus, Snyder-Theilen feline sarcoma virus, Trager duck spleen necrosis virus, Viper retrovirus, Wooly monkey sarcoma virus, Jembrana disease virus, Puma lentivirus. Bovine foamy virus, Equine foamy virus, Feline foamy virus, Brown greater galago prosimian foamy virus, Bornean orangutan simian foamy virus, Central chimpanzee simian foamy virus, Cynomolgus macaque simian foamy virus, Eastern chimpanzee simian foamy virus, Grivet simian foamy virus. Guenon simian foamy virus, Japanese macaque simian foamy virus, Rhesus macaque simian foamy virus, Spider monkey simian foamy virus. Squirrel monkey simian foamy virus, Taiwanese macaque simian foamy virus, Western chimpanzee simian foamy virus, Western lowland gorilla simian foamy virus. White-tufted-ear marmoset simian foamy virus, Yellow-breasted capuchin simian foamy virus, or any combination thereof. Other aspects of the invention provide that the nucleic acid molecules are packaged in a non-viral delivery system. For example, they may be packaged in lipid nanoparticles.

Aspects of the invention provide that the one or more promoters comprise one or more tissue-specific or cell-specific promoters. For example, the promoters may be specific to bone marrow, hematopoietic stem cells (HSCs), epithelial cells, liver cells, ocular cells, muscle cells, or T cells. The one or more promoters may include an hCMV promoter.

Some aspects of the invention provide that the one or more transgenes encode one or more therapeutic proteins, diagnostic proteins, or reporter proteins, or fragments thereof. For example, the one or more transgenes may encode one or more therapeutic proteins, diagnostic proteins, or reporter proteins, or fragments thereof. The therapeutic protein could be beta-globin, cystic fibrosis transmembrane conductance regulator (CFTR), Factor VIII, dystrophin, or RP GTPase regulator (RPGR). The reporter protein could be a fluorescent protein or luciferase.

Other aspects of the invention provide that the non-viral delivery system is targeted to a specific tissue or cell type. The specific tissue or cell type could be bone marrow, HSCs, epithelial cells, liver cells, ocular cells, muscle cells, or T cells. The non-viral delivery system is a lipid nanoparticle, a liposome, a polypeptide nanoparticle, a silica nanoparticle, a gold nanoparticle, a polymeric nanoparticle, a dendrimer, a cationic nanoemulsion, an inorganic carrier (such as CaP), a polymer and lipid hybrid carrier.

Methods for expressing a gene in a subject in need thereof are also provided, where the method includes administering to the subject an effective amount of the above-referenced nucleic acids or a composition thereof (e.g., lipid nanoparticle) resulting in the expression of one or more transgenes in the subject. The method results in expressing a gene in a cell by delivering the nucleic acids into the cell. The method could include using the nucleic acids or a composition thereof (e.g., lipid nanoparticle) by delivering them to a subject, thereby expressing the one or more transgenes in the subject.

Aspects of the invention provide methods of treating a disease or condition in a subject in need thereof by delivering the nucleic acids or a composition thereof (e.g., lipid nanoparticle) to the subject, thereby expressing the one or more transgenes in the subject. The disease or condition to be treated can be a genetic disease or condition. The disease or condition can be a hereditary genetic disease or condition. The disease or condition can be sickle cell disease, beta-thalassemia, haemophilia B, retinitis pigmentosa, Duchenne muscular dystrophy, cystic fibrosis, or cancer.

Some aspects of the invention provide that the one or more transgenes are integrated into the genome of a target cell. For example, the one or more transgenes may be stably expressed for at least a week, at least two weeks, at least a month, at least 6 months, at least a year, or for the lifetime of the subject.

Some aspects of the invention provide methods of eliciting an immune response in a subject in need thereof by administering to the subject an effective amount of the nucleic acids or a composition thereof (e.g., lipid nanoparticle), thereby expressing the one or more transgenes in the subject. For example, the subject can have cancer, and the one or more transgenes encode a tumor antigen. Alternatively, the subject can have or be at risk of contracting an infectious disease, and the one or more transgenes encode an antigen associated with the infectious disease. Embodiments include delivery of the nucleic acids locally or systemically.

Aspects of the invention also provide one or more nucleic acid templates comprising a 5' UTR, a nucleic acid sequence encoding one or more retroviral Pol polyprotein components, and a 3' UTR, wherein the expression of Pol polyprotein components do not require translational slippage from an in-line gag gene. Other aspects of the invention provide one or more nucleic acid templates comprising a 5' UTR, a nucleic acid sequence encoding a gag-pol gene comprising a frameshift mutation, and a 3' UTR. Yet other aspects of the invention provide one or more nucleic acid templates comprising a 5' UTR, a nucleic acid sequence encoding a gag-pol gene, and a 3' UTR, wherein the gag-pol gene does not encode the matrix protein. The nucleic acid templates can also include a nucleic acid sequence encoding one or more accessory proteins selected from MA, p6, NC, CA, Vif, Tat, Nef, Vpr, and Vpu. In some embodiments, the Pol polyprotein components and/or accessory proteins of the templates are based on Pol polyproteins and accessory proteins from either human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), bovine immunodeficiency virus (BIV), human foamy virus (HFV), murine leukemia virus (MLV), Moloney murine leukemia virus (MoLV), Friend virus (FV), Abelson murine leukemia virus (A-MLV), murine stem cell virus (MSCV), mouse mammary tumor virus (MMTV), Moloney murine sarcoma virus (MoMSV), Rous sarcoma virus (RSV), Fujinami sarcoma virus (FuSV), FBR murine osteosarcoma virus (FBR MSV), Avian myelocytomatosis virus-29 (MC29). Avian erythroblastosis virus (AEV), human T-cell leukemia virus (HTLV), Friend MLV (FrMLV), Avian sarcoma virus (ASV), Avian leukosis virus, Avian myeloblastosis virus, UR2 sarcoma virus, Y73 sarcoma virus, Jaagsiekte sheep retrovirus. Langur virus. Mason-pfizer monkey virus, Squirrel monkey retrovirus, Avian carcinoma mill hill virus 2, Bovine leukemia virus, Primate T-lymphotropic virus 1, Primate T-lymphotropic virus 2, Primate T-lymphotropic virus 3, Walleye dermal sarcoma virus, Walleye epidermal hyperplasia virus 1, Walleye epidermal hyperplasia virus 2, Chick syncytial virus, Feline leukemia virus, Finkel-Biskis-Jinkins murine sarcoma virus, Gardner-Amstein feline sarcoma virus, Gibbon ape leukemia virus, Guinea pig type-C oncovirus, Hardy-Zuckerman feline sarcoma virus, Harvey murine sarcoma virus, Kirsten murine sarcoma virus, Koala retrovirus, Moloney murine sarcoma virus, Porcine type-C oncovirus, Reticuloendotheliosis virus, Snyder-Theilen feline sarcoma virus, Trager duck spleen necrosis virus, Viper retrovirus, Wooly monkey sarcoma virus, Jembrana disease virus. Puma lentivirus, Bovine foamy virus, Equine foamy virus, Feline foamy virus, Brown greater galago prosimian foamy virus, Bornean orangutan simian foamy virus, Central chimpanzee simian foamy virus. Cynomolgus macaque simian foamy virus, Eastern chimpanzee simian foamy virus, Grivet simian foamy virus, Guenon simian foamy virus. Japanese macaque simian foamy virus, Rhesus macaque simian foamy virus, Spider monkey simian foamy virus, Squirrel monkey simian foamy virus, Taiwanese macaque simian foamy virus, Western chimpanzee simian foamy virus, Western lowland gorilla simian foamy virus, White-tufted-ear marmoset simian foamy virus, Yellow-breasted capuchin simian foamy virus, or any combination thereof. Methods of producing a nucleic acid, such as an RNA, are also provided, where the method includes the in vitro transcription of the nucleic acid template.

Other aspects of the invention provide a kit comprising the nucleic acids or nucleic acid template mentioned above. The nucleic acids or nucleic acid templates may be provided in one or more containers.

Other advantages, features, and uses of the invention will be apparent from the detailed description of certain exemplary, non-limiting embodiments, the drawings; the non-limiting working examples; and the claims.

BRIEF DESCRIPTION OF THE DRAWINGS

FIG. 2 is a table which describes examples of current approaches to gene therapy and the major advantages and challenges associated with each approach.

FIG. 5A is a schematic which illustrates an exemplary embodiment in which the protease (PR), reverse transcriptase/RNase H (RT) and integrase (IN) are each encoded on a single nucleic acid construct and where each component is separated by autoprocessing by the PR. FIG. 5B is a schematic which illustrates an exemplary embodiment in which the individual units RT and IN are on a bicistronic construct. FIG. 5C is a schematic which illustrates an exemplary embodiment in which the individual units RT and IN are on separate constructs.

FIG. 7A shows a schematic of the functional units, a Gag polyprotein RNA and a Pol polyprotein RNA (the functional unit mRNAs), and a transgene-encoding RNA (the 'genome' RNA). FIG. 7B shows the expression of the reporter transgene when transfected with the functional unit RNAs.

FIG. 8A is a schematic depicting RNA constructs encoding WT integrase (IN); stabilized Met-Gly, human codon optimized (hCO) IN; and stabilized Met-Gly hCO ΔINS IN. FIG. 8B shows a capillary electropherogram of Met-Gly, hCO ΔINS IN mRNA before and after polyadenylation. FIG. 8C shows a Western blot analysis of the expression of WT IN mRNA, Met-Gly hCO IN mRNA; and Met-Gly hCO ΔINS IN mRNA. FIG. 8D shows confocal microscopy images showing the subcellular localization of optimized integrase following RNA transfection into 293FT cells.

DETAILED DESCRIPTION

Figure 1:
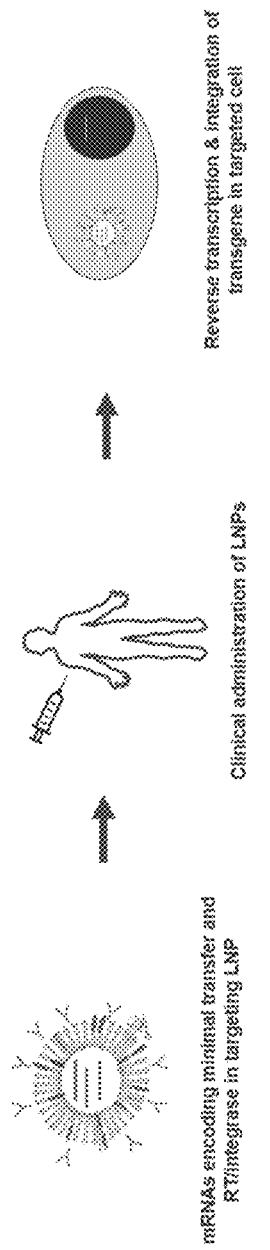
FIG. 1 is a schematic which outlines the approach for an mRNA-based gene therapy platform.

According to some aspects of the present disclosure, minimal design nucleic acid compositions are effective for in vivo gene therapy. This minimal design can overcome some of the limitations of the lentiviral approach, including the need to produce virus by expansion in cells, which is slow and expensive; and the need for processing of viral particles, which can be inefficient. These are examples of the advantages of the disclosed nucleic acid compositions, and those skilled in the art will recognize the other advantages. The disclosure also provides nucleic acid molecules, methods of use, methods of treatment, nucleic acid templates, cells, and kits. The disclosure also provides for modifications to increase the stability and/or functioning of the nucleic acid, and/or the stability and/or functioning of the encoded protein. These modifications can include mutations in one or more intrinsic instability (INS) elements; a functional unit, such as an integrase, with an N-terminal methionine-glycine dipeptide; fusion of a functional unit, such as an integrase, to a homing protein; use of codon optimization for expression in a host cell; and/or use of a priming oligonucleotide. Other modifications are as disclosed herein.

Provided herein, in some aspects, are nucleic acids and compositions of nucleic acids for the delivery of a transgene (for example, but not limited to beta-globin, cystic fibrosis transmembrane conductance regulator (CFTR). Factor VIII, dystrophin, or RP GTPase regulator (RPGR)), kits, and methods of use. In some aspects, the disclosure provides non-viral compositions based on retroviruses (e.g., lentiviruses) comprising: at least a first nucleic acid molecule encoding a retroviral Pol polyprotein which is processed to provide for protease activity, reverse transcription, and integration of a transgene-encoding nucleic acid molecule, and at least a second nucleic acid molecule comprising one or more transgenes flanked by long terminal repeat (LTR) sequences, for delivery of one or more transgenes to a target cell. The nucleic acid molecule comprising one or more transgenes may also be referred to herein as "the transgene-encoding nucleic acid molecule." In some aspects, the disclosure provides for the encoding of the components of the Pol polyprotein as separate, multiple functional units, including, but not limited to, the units encoding reverse transcription and integration activity. These multiple functional units can be encoded on one nucleic acid or two or more nucleic acids. The protease of the Pol polyprotein can also be encoded on the same or a different construct as one or more of the other Pol polyprotein components or omitted if the required enzymatic activities (e.g., reverse transcriptase, integrase) are not encoded as viral polyproteins. In some embodiments, the Pol polyprotein components are encoded on one or more nucleic acids with intervening polycistronic elements. The polycistronic elements may be IRESes and/or 2A sequences and/or other polycistronic elements. In some embodiments, the compositions of the disclosure further comprise one or more nucleic acid sequences encoding one or more accessory retroviral proteins (accessory proteins) which may enhance reverse transcription and integration of the transgene-encoding nucleic acid. As used herein, an "accessory protein" refers to any retroviral protein other than a Pol polyprotein component that can enhance reverse transcription and/or integration of the transgene-encoding nucleic acid. An accessory protein may be a structural protein, including, but not limited to, MA, CA, NC, and Env, or a non-structural protein, including, but not limited to, Tat, Rev, Nef, Vpr, Vpu, and Vif. The nucleic acid sequences encoding the one or more accessory retroviral proteins can be on one or more nucleic acids encoding the Pol polyprotein components or can be on one or more nucleic acids that do not encode the Pol polyprotein components. In some embodiments, the stability of the mRNAs is increased by, for example, introducing mutations in one or more intrinsic instability (INS) elements. In some embodiments, the stability of the translated proteins is increased by, for example, incorporating an N-terminal methionine-glycine dipeptide. In some embodiments, the translation efficiency of the mRNA is increased using codon optimization for expression in the host cell (e.g., codon optimization for expression in human cells). In some embodiments, the proteins of the disclosure, such as integrase, are fused to a homing protein. In some embodiments, the composition comprises a priming oligonucleotide. The nucleic acids and compositions of the disclosure may be used for ex vivo or in vivo expression of one or more transgenes by a cell, tissue, organ, or subject, or in vitro for the production of recombinant proteins. In addition, the nucleic acid molecules can be packaged into a non-viral delivery system (e.g., a lipid nanoparticle), thus avoiding the need to produce viral particles, which requires expansion in cells and is slow and expensive, and avoiding the risks associated with virus-based approaches such as immunogenicity.

Definitions

General methods in molecular and cellular biochemistry can be found in such textbooks as *Molecular Cloning: A Laboratory Manual*, 3rd Ed. (Sambrook et al., CSH Laboratory Press 2001); *Short Protocols in Molecular Biology*, 4th Ed. (Ausubel et al. eds., John Wiley & Sons 1999); *Protein Methods* (Bollag et al., John Wiley & Sons 1996); *Nonviral Vectors for Gene Therapy* (Wagner et al. eds., Academic Press 1999); *Viral Vectors* (Kaplift & Loewy eds., Academic Press 1995); *Immunology Methods Manual* (I. Lefkovits ed., Academic Press 1997); and *Cell and Tissue Culture: Laboratory Procedures in Biotechnology* (Doyle & Griffiths, John Wiley & Sons 1998), the disclosures of which are incorporated herein by reference.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (e.g., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, and any other modified configuration of the immunoglobulin molecule that comprises an antigen recognition site of the required specificity, including glycosylation variants of antibodies, amino acid sequence variants of antibodies, and covalently modified antibodies.

An "expression cassette" or "nucleic acid template" comprises any nucleic acid construct capable of serving as a template for the production of DNA or RNA, including a gene/coding sequence of interest as well as non-translated RNAs.

A "polyprotein" refers to a polypeptide comprising covalently conjoined smaller proteins that can occur in nature and is typically cleaved into the constituent proteins with different biological functions.

The "Gag polyprotein" refers to the precursor polyprotein encoded by the gag (group-specific antigen) gene. The Gag polyprotein is processed during maturation to form matrix protein (MA), capsid protein (CA), spacer peptide 1 (SP1), nucleocapsid protein p7 (NC), spacer peptide 2 (SP2), and P6 protein. The terms "Gag protein" and "Gag polyprotein component" refers to one or more of the proteins encoded by the gag gene, i.e., MA, CA, SP1, NC, SP2, or P6.

The "Pol polyprotein" refers to the precursor polyprotein encoded by the pol gene. The Pol polyprotein is processed to form protease (PR), reverse transcriptase/RNase H (RT/RH), and integrase (IN). Each component is separated by autoprocessing by PR. The terms "Pol protein" and "Pol polyprotein component" refer to one or more of the proteins encoded by the pol gene, i.e., RT/RH, IN, or PR.

The "percent identity" of two nucleic acid sequences may be determined by any method known in the art. In some embodiments, the percent identity of two nucleic acid sequences is determined using the algorithm of Karlin and Altschul, *Proc. Natl. Acad Sci. USA* 87:2264-68, 1990, modified as in Karlin and Altschul, *Proc. Natl. Acad Sci. USA* 90:5873-77, 1993. Such an algorithm is incorporated into the NBLAST and XBLAST programs (version 2.0) of Altschul et al., *J. Mol. Biol.* 215:403-10, 1990. BLAST nucleotide searches can be performed with the NBLAST program, score=100, wordlength-12, to obtain guide sequences homologous to a target nucleic acid. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The terms "polycistronic" and "multicistronic" are used interchangeably to refer to a nucleic acid molecule that encodes more than one polypeptide separately within the same nucleic acid molecule. For example, a polycistronic mRNA is an mRNA that encodes more than one polypeptide in the same transcript. A "polycistronic element" or "multicistronic element" refers to an element that separates individual polypeptides in a polycistronic nucleic acid to allow for independent translation and/or post-translational processing.

The terms "polypeptide" and "protein" are used interchangeably to refer to a polymer of amino acid residues linked by peptide bonds, and for the purposes of the instant disclosure, have a minimum length of at least 5 amino acids. Both full-length proteins and fragments thereof greater than 5 amino acids are encompassed by the definition. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" or "protein" refers to a protein that includes modifications, such as deletions, additions, and substitutions (generally conservative in nature as would be known to a person in the art) to the native sequence, as long as the protein maintains the desired activity relevant to the purposes of the described methods. These modifications can be deliberate, as through site-directed mutagenesis, or can be accidental, such as through mutations of hosts that produce the proteins, or errors due to PCR amplification or other recombinant DNA methods.

The terms "nucleic acid" or "nucleic acid molecule," as used herein, generally refers to deoxyribonucleic acid (DNA) or ribonucleic acid (RNA). In some embodiments, "nucleic acid" refers to individual nucleic acid residues (e.g., nucleotides and/or nucleosides). In some embodiments, "nucleic acid" refers to an oligonucleotide chain comprising individual nucleotides. As used herein, the terms "oligonucleotide" and "polynucleotide" can be used interchangeably to refer to a polymer of nucleotides (e.g., a string of at least two nucleotides). A nucleic acid may be single-stranded or double-stranded. The nucleotide monomers in the nucleic acid molecules may be naturally occurring nucleotides, modified nucleotides or combinations thereof. Modified nucleotides, in some embodiments, comprise modifications of the sugar moiety and/or the pyrimidine or purine base.

The terms "subject," and "patient." are used interchangeably herein. In some embodiments, a subject is a mammal. "Mammal" refers to any animal classified as a mammal, including humans, domestic and farm animals, and zoo, sports, or pet animals, such as dogs, horses, cats, cows, sheep, goats, pigs, camels, etc. In some embodiments, the mammal is human. In some embodiments, the subject is avian.

A "therapeutically effective amount" of the compositions of the disclosure generally refers to an amount sufficient to elicit the desired biological response, e.g., express the transgene in a target cell, treat the condition, etc. As will be appreciated by those of ordinary skill in this art, the effective amount of an agent described herein may vary depending on such factors as the condition being treated, the mode of administration, and the age, body composition, and health of the subject.

The term "transgene" or "transgene sequence" refers to an exogenous nucleotide sequence encoding a protein or RNA product of interest.

The terms "treat", "treating", "treatment", and "therapy" encompass an action that occurs while a subject is suffering from a condition which reduces the severity of the condition (or a symptom associated with the condition) or retards or slows the progression of the condition (or a symptom associated with the condition).

Minimal Gene Therapy Platform

The disclosure is based in part on the finding that nucleic acid molecules of retroviral (e.g., lentiviral) origin can be used to deliver, integrate, and stably express transgenes (e.g., for use in gene therapy) using a minimal system comprising at least a first nucleic acid encoding a retroviral Pol polyprotein which is processed to provide for, potentially among other things, reverse transcription and integration of a transgene-encoding nucleic acid, and at least a second nucleic acid molecule comprising one or more transgenes flanked by LTR sequences. In some embodiments, the components of the Pol polyprotein are encoded as separate units on one or more nucleic acid molecules. In some embodiments, the one or more nucleic acid molecules encoding the retroviral Pol polyprotein components further encode one or more accessory retroviral proteins. In some embodiments, the system comprises one or more additional nucleic acid molecules encoding one or more accessory retroviral proteins. In some embodiments, a minimal system comprises two nucleic acid molecules, one nucleic acid molecule providing the reverse transcriptase and integrase functions (either as a polyprotein that is processed with the protease, or as separately encoded units), and one nucleic acid molecule encoding the one or more transgenes. In some embodiments, the minimal system comprises two or more nucleic acid molecules (e.g., 2, 3, 4, or 5, or more). The nucleic acid molecules can be packaged into a non-viral delivery system (e.g., a lipid nanoparticle), thus bypassing the production of viral particles, which requires expansion in cells and is slow and expensive, and avoiding the risks associated with virus-based approaches, such as immunogenicity.

The compositions of the disclosure have several advantages over current gene and cell therapy approaches. Some of the challenges associated with current gene therapy approaches, such as CRISPR/Cas9, retroviruses, lentiviruses, herpesviruses, adenoviruses, and adeno-associated viruses (AAV), are shown in FIG. 2. Compared to existing approaches, the compositions of the disclosure can function in both dividing and non-dividing cells, have high transgene size capacity (e.g., 4-5 kb. 5-6 kb. 6-7 kb, 7-8 kb, 8-9 kb, 9-10 kb, or greater than 4 kb, greater than 5 kb, greater than 6 kb, greater than 7 kb, greater than 8 kb, greater than 9 kb, or greater than 10 kb), and/or do not require the costly production of viruses and/or viral particles. The compositions of the disclosure also overcome some of the limitations associated with HIV-1 and third generation lentiviral vectors. In HIV-1 vectors, all of the components required for the HIV-1 life cycle are on a single RNA genome. HIV-1 vectors are also replication competent (i.e., it can replicate after integration), have a packaging signal, which allows for packaging the genome into a viral particle, have an mRNA nuclear export element for HIV-1 mRNA, and have viral machinery in cis. HIV-1 vectors present safety concerns that preclude their in vivo use. Next generation lab-based lentiviruses, on the other hand, feature self-inactivation after the integration step, viral machinery in trans on separate constructs, and transgenes with promoter/enhancer regions. However, these require co-transfection of packaging cells with multiple plasmids, resulting in inefficient viral particle production. Partially packaged or mispackaged viral particles are also highly immunogenic. In an improvement upon the aforementioned lentiviral vectors, the minimal RNA design described herein does not require particle formation or packaging, and in some embodiments, features only reverse transcription and integration functions in trans on a separate construct. By requiring only minimal components providing reverse transcription and integration and transfer (i.e., transgene-encoding) functions, while being self-inactivating and bypassing the production of viral particles, the compositions of the disclosure address the challenges associated with current lentiviral approaches. Further, non-viral delivery systems can be easily functionalized with targeting moieties, simplifying administration and nucleic acid synthesis (e.g., RNA synthesis) and delivery system production can both be cell-free, thus simplifying the manufacturing process.

The compositions described herein comprise the following basic components: one or more nucleic acid molecules encoding retroviral Pol polyprotein components for reverse transcription, for example RT/RH, and integration, for example IN, of a transgene-encoding nucleic acid, and a nucleic acid molecule comprising one or more transgene sequences flanked by LTR sequences. The Pol polyprotein can be expressed and processed to provide protease activity (for example with the PR protein), reverse transcriptase activity (for example with the RT/RH protein), and integration (for example with the IN protein) of the transgene-encoding nucleic acid molecule. The Pol polyprotein components can instead be expressed as separate, multiple functional units on one or more nucleic acid molecules. When expressed as separate units, the Pol polyprotein component providing protease activity may or may not be expressed. The compositions of the disclosure may optionally further comprise one or more nucleic acid sequences encoding one or more accessory retroviral proteins to enhance reverse transcription and integration of the transgene-encoding nucleic acid. The one or more accessory proteins may be encoded in cis or in trans with the one or more Pol polyprotein components. In some embodiments, the nucleic acid molecules encoding the Pol polyprotein further encode one or more accessory retroviral proteins. In some embodiments, the compositions of the disclosure comprise one or more additional nucleic acid molecules encoding one or more accessory retroviral proteins. In some embodiments, a composition comprises two nucleic acid molecules, one nucleic acid molecule providing the reverse transcriptase and integrase functions (for example, but not limited to Pol polyprotein and/or one or more accessory retroviral proteins) and one nucleic acid molecule encoding the one or more transgenes. In some embodiments, a composition comprises two or more nucleic acid molecules (e.g., 2, 3, 4, or 5, or more). In some embodiments, a composition does not comprise any accessory retroviral proteins. The compositions of the disclosure are packaged in a non-viral delivery system (e.g., a lipid nanoparticle) for in vivo or ex vivo delivery.

The nucleic acid molecules may be RNA molecules or DNA molecules, both genomic and/or cDNA, or a hybrid of RNA and DNA, wherein the nucleic acid contains any combination of deoxyribonucleotides and ribonucleotides (e.g., artificial or natural). The nucleic acid molecules may be single-stranded (ss) or double-stranded (ds), or may contain portions of both single-stranded and double-stranded sequence. In some embodiments, the nucleic acid molecules are DNA molecules. The DNA molecules may be ssDNA molecules or dsDNA molecules (e.g., linear dsDNA molecules). In some embodiments, the nucleic acid molecules are RNA molecules. The RNA molecules may be ssRNA or dsRNA molecules. In some embodiments, the RNA molecules may be ssRNA molecules. In some embodiments, the nucleic acid molecules may be mRNA molecules.

Figure 6:
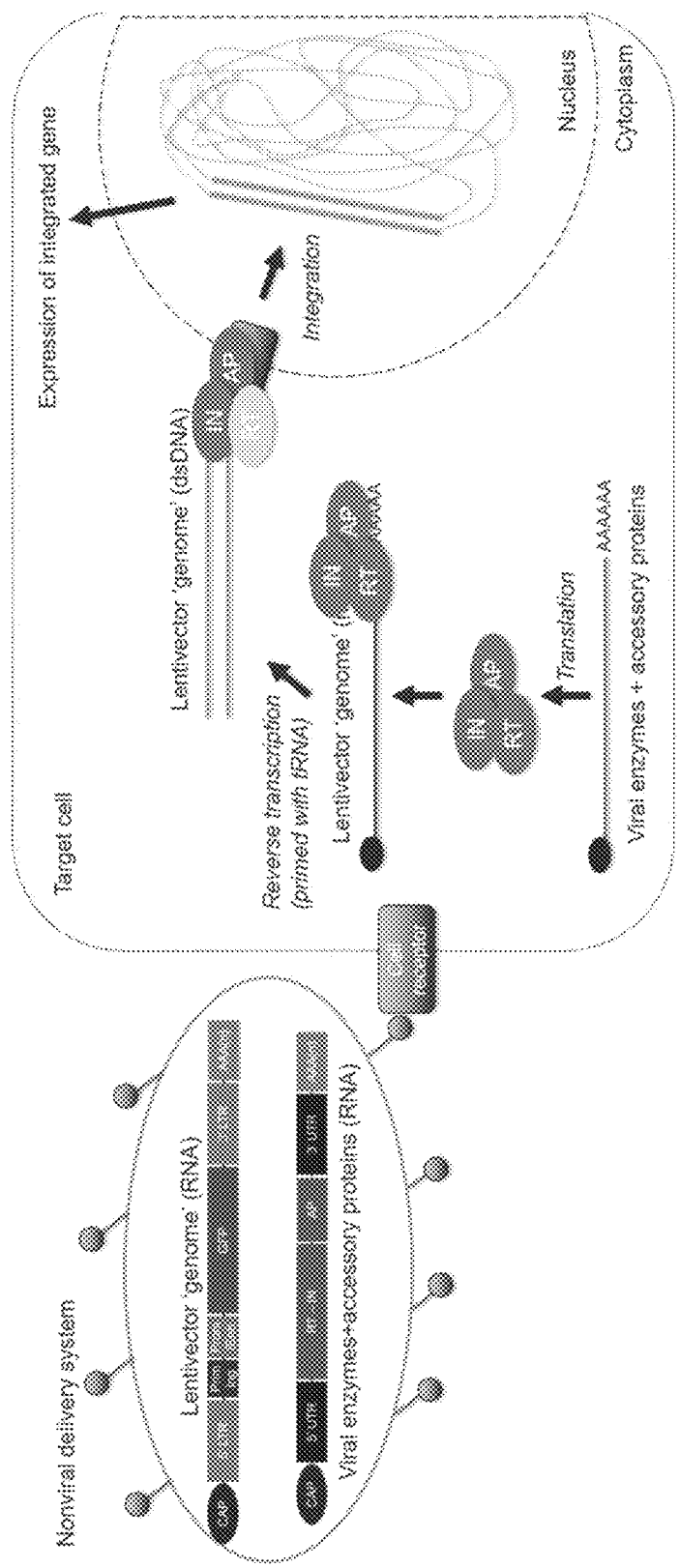
FIG. 6 is another schematic depicting an mRNA-based gene therapy approach. The viral machinery required for reverse transcription and integration (e.g., viral enzymes and/or one or more accessory proteins) and the transgene are provided on separate RNAs. A non-viral delivery system, optionally using surface markers, is used to deliver the RNAs to the target cell. The transgene-encoding RNA is also referred to as the lentivector 'genome' RNA. The expression of the transgene relies on the translation of the viral enzymes, conversion of the lentivector 'genome' RNA into DNA, and integration of the DNA into genomic DNA in the target cell, which results in long-lasting expression of the transgene.

In some embodiments, a composition of the disclosure comprises one or more RNA molecules encoding retroviral Pol polyprotein components, and an RNA molecule comprising one or more transgene sequences flanked by LTR sequences. In some embodiments, a composition of the disclosure comprises two RNA molecules: a first RNA molecule encoding a retroviral Pol polyprotein and a second RNA molecule comprising a transgene sequence flanked by LTR sequences. In some embodiments, the RNA molecule encoding the Pol polyprotein expresses the polyprotein as a canonical unit with each component separated by protease processing. In some embodiments, the RNA molecule encoding the Pol polyprotein components expresses them as individual units, for example, as a bicistronic construct. In some embodiments, the RNA molecule encoding the Pol polyprotein further encodes one or more accessory retroviral proteins as described herein. In some embodiments, the composition comprises one or more additional RNA molecules encoding one or more accessory retroviral proteins. The in vivo approach for embodiments in which the nucleic acid molecules are RNA molecules is outlined in FIG. 1 and FIG. 6.

Reverse Transcription and Integration Functions

Figure 9:
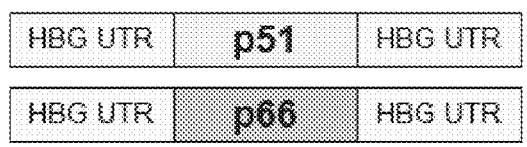
FIG. 9 illustrates an exemplary embodiment where the reverse transcriptase is encoded as individual p51 and p66 subunits.

One or more nucleic acids of the system encode the retroviral Pol polyprotein which is processed to provide for the functional units responsible for protease activity, reverse transcription, and integration of the one or more transgenes. In some embodiments, a nucleic acid molecule comprising a 5' UTR, a nucleic acid sequence encoding a retroviral Pol polyprotein (the retroviral pol gene), and a 3' UTR, provides the reverse transcription and integration functions. Thus, in some embodiments, all Pol polyprotein components are encoded on one nucleic acid molecule with a 5' and 3' UTR. In some embodiments, the Pol polyprotein components are encoded on two or more nucleic acid molecules each with a 5' and 3' UTR. In some embodiments, the Pol polyprotein components are encoded on one or more nucleic acid molecules each with a 5' and 3' UTR and are separated by one or more poly cistronic elements (e.g., one or more IRESes and/or 2A peptide-encoding sequences, and/or other polycistronic elements). Any other polycistronic element that will facilitate translation could also be used. In some embodiments, the nucleic acid molecules do not encode the Pol protease, e.g., where the Pol polyprotein components reverse transcriptase and integrase are encoded as separate units on one or more nucleic acid molecules or are separated by intervening polycistronic elements (e.g., IRESes and/or 2A peptide-encoding sequences, and/or other polycistronic elements). In further embodiments, the Pol polyprotein component reverse transcriptase may be encoded as individual p51 and p66 subunits (FIG. 9). In some embodiments, p51 and p66 are encoded on separate nucleic acid molecules each with a 5' and 3' UTR. In some embodiments, p51 and p66 are encoded as separate units on the same nucleic acid separated by a polycistronic element (e.g., an IRES or 2A peptide-encoding sequence, or other polycistronic element).

Compared to the canonical design w % here translational slippage from gag is required for pol expression, in some embodiments, expression of Pol proteins can be increased by producing the Pol polyprotein or the individual Pol polyprotein components from a separate construct and by encoding different UTRs for mRNA stability and high levels of translation. In some embodiments, heterologous UTRs are selected to improve mRNA stability and/or level of translation. In some embodiments, the UTRs include 3' or 5' sequences from mRNA molecules which are stable and highly translated (for example, but not limited to, β-globin, actin, GAPDH, tubulin, histone, or citric acid cycle enzymes). Engineered or synthetic UTRs (i.e., UTRs based on rational design that are non-naturally occurring and distinct from mutated naturally-occurring UTRs) may also be used to enhance stability and/or translation. The sequences of human UTRs are available on GenBank.

In some embodiments, in addition to encoding functional units, the nucleic acid sequences encode one or more accessory retroviral proteins to enhance reverse transcription and/or integration. In some embodiments, the one or more accessory proteins are encoded in cis (i.e., encoded by the same nucleic acid molecule) with one or more Pol polyprotein components. In some embodiments, the one or more accessory proteins are encoded in cis with all Pol polyprotein components. In some embodiments, the one or more accessory proteins are encoded in cis with the Pol polyprotein. Thus, in some embodiments, all Pol polyprotein components and accessory proteins are encoded by one nucleic acid molecule with a 5' and 3' UTR. In some embodiments, the nucleotide sequences encoding the Pol polyprotein components and/or the accessory proteins are separated by one or more polycistronic elements (e.g., one or more IRESes and/or 2A peptide-encoding sequences, and/or other polycistronic elements). In some embodiments, the nucleotide sequences encoding the Pol polyprotein components and/or the accessory proteins encode a fusion protein comprising the Pol polyprotein components and/or the accessory proteins. In some embodiments, the one or more accessory proteins are encoded in trans (i.e., encoded by a separate nucleic acid molecule) from the Pol polyprotein components. In some embodiments, the Pol polyprotein components and accessory proteins are encoded by two or more (e.g., two, three, four, or five, or more) nucleic acid molecules, each with a 5' and 3' UTR In some embodiments, the UTRs include 3' or 5' sequences from mRNA molecules which are stable and highly translated (including, but not limited to, globin, actin. GAPDH, tubulin, histone, or citric acid cycle enzymes).

In some embodiments, the one or more accessory proteins are selected from gag matrix protein (MA) (p17), nucleocapsid (NC) (p9), capsid protein (CA) (p24), p6, viral infectivity factor (Vif), transactivator-of-transcription (Tat), negative regulatory factor (Nef), viral protein R (Vpr), and viral protein u (Vpu). In some embodiments, the accessory proteins may be wild-type proteins or may be mutated proteins. In some embodiments, a mutated accessory protein is CA N74D or CA E45A. The numbering corresponds to the wild-type HIV-1 CA protein and corresponding mutations in other retroviral CA proteins can be readily determined by one of skill in the art. In some aspects, the wild-type HIV-1 strain can be NL4-3. In some embodiments, the system comprises one accessory protein selected from MA, NC, CA, p6, Vif, Tat, Nef, Vpr, and Vpu. In some embodiments, the accessory protein is NC. In some embodiments, the accessory protein is CA. In some embodiments, a composition of the disclosure comprises two accessory proteins selected from MA, NC, CA, p6 Vif, Tat, Nef, Vpr, and Vpu. In some embodiments, a composition of the disclosure comprises three accessory proteins selected from MA, NC, CA, p6, Vif, Tat, Nef, Vpr, and Vpu. In some embodiments, a composition of the disclosure comprises four, five, six, seven, or eight accessory proteins selected from MA, NC, CA, p6, Vif, Tat, Nef, Vpr, and Vpu. In some embodiments, the system comprises MA, NC, CA, p6, Vif, Tat, Nef, Vpr, and Vpu.

In some embodiments, the one or more accessory proteins are expressed from the gag polyprotein (p55). Thus, in some embodiments, a nucleic acid molecule comprises the retroviral gag gene. In some embodiments, a nucleic acid molecule of the disclosure comprises a nucleic acid sequence comprising the gag and pol genes in the canonical gag-pol overlapping orientation. In some embodiments, a nucleic acid molecule of the disclosure comprises a nucleic acid sequence encoding a fusion of the Gag and Pol polyproteins. In some embodiments, a nucleic acid of the disclosure comprises a nucleic acid sequence encoding Gag and Pol polyproteins separated by a 2A peptide-encoding sequence. In some embodiments, a nucleic acid molecule of the disclosure encodes one or more Pol polyprotein components and one or more Gag polyprotein components as separate units. In some embodiments, the separate units are joined by one or more polycistronic elements (e.g., one or more 2A peptide-encoding sequences and/or IRESes and/or other polycistronic elements). In some embodiments, a nucleic acid of the disclosure comprises a modified gag-pol gene that does not encode the matrix protein (MA). In some embodiments, a nucleic acid of the disclosure comprises a modified gag-pol gene comprising a frameshift mutation. In some embodiments, a nucleic acid of the disclosure comprises a modified gag-pol gene comprising a single nucleotide insertion disrupting the gag-pol frameshift mechanism. In some embodiments, a nucleic acid of the disclosure comprises a gag gene that does not encode MA.

In some embodiments, the nucleic acid molecules or compositions of the disclosure are capable of integrating the one or more transgenes into the host genome in the absence of functional retroviral Rev and/or Env proteins. In some embodiments, the nucleic acid molecules or compositions of the disclosure do not contain nucleic acid sequences that express proteins encoded by at least one of: retroviral rev and retroviral env. In some embodiments, the nucleic acid molecules or compositions of the disclosure do not contain nucleic acid sequences that express proteins encoded by both retroviral rev and env genes. In some embodiments, the nucleic acid molecules or compositions of the disclosure do not comprise any nucleic acid sequences encoding retroviral Gag proteins. In other embodiments, the nucleic acid molecules or compositions of the disclosure do not comprise nucleic acid sequences that are able to express all retroviral Gag proteins. In some embodiments, the nucleic acid molecules or compositions of the disclosure do not comprise nucleic acid sequences encoding the following retroviral Gag proteins: MA, SP1, SP2, and p6. In some embodiments, the nucleic acid molecules or compositions of the disclosure do not comprise nucleic acid sequences encoding MA. In some embodiments, the nucleic acid molecules or compositions of the disclosure do not comprise any nucleic acid sequences encoding retroviral Gag proteins. In other embodiments, the nucleic acid molecules or compositions of the disclosure do not comprise nucleic acid sequences that are able to express all retroviral Gag proteins.

In some embodiments, a composition of the disclosure further comprises a nucleic acid sequence encoding NC. In some embodiments, NC is encoded by a separate nucleic acid molecule comprising a 5' UTR and a 3' UTR In some embodiments, the one or more nucleic acid molecules encoding the retroviral Pol polyprotein components further comprise a nucleic acid sequence encoding NC in cis. In some embodiments, a nucleic acid molecule encoding a Pol polyprotein encodes NC in cis. In some embodiments, nucleic acid sequences encoding other Gag proteins (including MA, CA, SP1. SP2, and p6) are not present. In some embodiments, nucleic acid sequences encoding MA, SP1, SP2, and p6 are not present.

In some embodiments, a composition of the disclosure further comprises a nucleic acid sequence encoding CA. In some embodiments, CA is encoded by a separate nucleic acid molecule comprising a 5' UTR and a 3' UTR. In some embodiments, the one or more nucleic acid molecules encoding the retroviral Pol polyprotein components further comprise a nucleic acid sequence encoding CA in cis. In some embodiments, a nucleic acid molecule encoding a Pol polyprotein encodes CA in cis. In some embodiments, nucleic acid sequences encoding other Gag proteins (including MA, NC, SP1. SP2, and p6) are not present. In some embodiments, nucleic acid sequences encoding MA, SP1, SP2, and p6 are not present.

In some embodiments, a composition of the disclosure further comprises a nucleic acid sequence encoding Vif. In some embodiments, Vif is encoded by a separate nucleic acid molecule comprising a 5' UTR and a 3' UTR. In some embodiments, the one or more nucleic acid molecules encoding the retroviral Pol polyprotein components further comprises a nucleic acid sequence encoding Vif in cis. In some embodiments, a nucleic acid molecule encoding a Pol polyprotein encodes Vif in cis.

In some embodiments, a composition of the disclosure further comprises a nucleic acid sequence encoding Tat. In some embodiments, Tat is encoded by a separate nucleic acid molecule comprising a 5' UTR and a 3' UTR. In some embodiments, the one or more nucleic acid molecules encoding the retroviral Pol polyprotein components further comprise a nucleic acid sequence encoding Tat in cis. In some embodiments, a nucleic acid molecule encoding a Pol polyprotein encodes Tat in cis.

In some embodiments, a composition of the disclosure further comprises a nucleic acid sequence encoding Nef. In some embodiments, Nef is encoded by a separate nucleic acid molecule comprising a 5' UTR and a 3' UTR In some embodiments, the one or more nucleic acid molecules encoding the retroviral Pol polyprotein components further comprise a nucleic acid sequence encoding Nef in cis. In some embodiments, a nucleic acid molecule encoding a Pol polyprotein encodes Nef in cis.

In some embodiments, a composition of the disclosure further comprises a nucleic acid sequence encoding Vpr. In some embodiments, Vpr is encoded by a separate nucleic acid molecule comprising a 5' UTR and a 3' UTR In some embodiments, the one or more nucleic acid molecules encoding the retroviral Pol polyprotein components further comprise a nucleic acid sequence encoding Vpr in cis. In some embodiments, a nucleic acid molecule encoding a Pol polyprotein encodes Vpr in cis.

In some embodiments, a composition of the disclosure further comprises a nucleic acid sequence encoding Vpu. In some embodiments, Vpu is encoded by a separate nucleic acid molecule comprising a 5' UTR and a 3' UTR. In some embodiments, the one or more nucleic acid molecules encoding the retroviral Pol polyprotein components further comprise a nucleic acid sequence encoding Vpu in cis. In some embodiments, a nucleic acid molecule encoding a Pol polyprotein encodes Vpu in cis.

In some embodiments, a composition of the disclosure further comprises a nucleic acid sequence encoding MA. In some embodiments, MA is encoded by a separate nucleic acid molecule comprising a 5' UTR and a 3' UTR. In some embodiments, the one or more nucleic acid molecules encoding the retroviral Pol polyprotein components further comprise a nucleic acid sequence encoding MA in cis. In some embodiments, a nucleic acid molecule encoding a Pol polyprotein encodes MA in cis.

In some embodiments, a composition of the disclosure further comprises a nucleic acid sequence encoding p6. In some embodiments, p6 is encoded by a separate nucleic acid molecule comprising a 5' UTR and a 3' UTR In some embodiments, the one or more nucleic acid molecules encoding the retroviral Pol polyprotein components further comprise a nucleic acid sequence encoding p6 in cis. In some embodiments, a nucleic acid molecule encoding a Pol polyprotein encodes p6 in cis.

In some embodiments, the nucleic acid sequences encoding the Pol polyprotein components and/or one or more accessory proteins are based on nucleic acid sequences from one or more retroviruses. In some embodiments, the nucleic acid sequences encoding the Pol polyprotein components and/or one or more accessory proteins are based on nucleic acid sequences from the same retrovirus. In some embodiments, the nucleic acid sequences encoding the Pol polyprotein components and/or one or more accessory proteins are based on nucleic acid sequences from two or more different retroviruses. In some embodiments, the nucleic acid sequences encoding the Pol polyprotein components and/or one or more accessory proteins are based on nucleic acid sequences from the murine leukemia virus (MLV). Moloney murine leukemia virus (MoLV), Friend virus (FV), Abelson murine leukemia virus (A-MLV), murine stem cell virus (MSCV), mouse mammary tumor virus (MMTV), Moloney murine sarcoma virus (MoMSV). Rous sarcoma virus (RSV), Fujinami sarcoma virus (FuSV), FBR murine osteosarcoma virus (FBR MSV), Avian myelocytomatosis virus-29 (MC29), Avian erythroblastosis virus (AEV), human T-cell leukemia virus (HTLV), avian sarcoma leukosis virus (ASLV), endogenous xenotropic MuLV-related virus VP62 (XMRV), primate T-lymphotropic virus (PTLV), walleye dermal sarcoma virus (WDSV), the human foamy virus (HFV), Friend MLV (FrMLV), Avian sarcoma virus (ASV), Avian leukosis virus, Avian myeloblastosis virus, UR2 sarcoma virus, Y73 sarcoma virus, Jaagsiekte sheep retrovirus, Langur virus, Mason-pfizer monkey virus, Squirrel monkey retrovirus, Avian carcinoma mill hill virus 2, Bovine leukemia virus, Primate T-lymphotropic virus 1, Primate T-lymphotropic virus 2, Primate T-lymphotropic virus 3, Walleye dermal sarcoma virus, Walleye epidermal hyperplasia virus 1, Walleye epidermal hyperplasia virus 2, Chick syncytial virus, Feline leukemia virus, Finkel-Biskis-Jinkins murine sarcoma virus, Gardner-Amstein feline sarcoma virus, Gibbon ape leukemia virus, Guinea pig type-C oncovirus, Hardy-Zuckerman feline sarcoma virus, Harvey murine sarcoma virus, Kirsten murine sarcoma virus, Koala retrovirus, Moloney murine sarcoma virus, Porcine type-C oncovirus. Reticuloendotheliosis virus, Snyder-Theilen feline sarcoma virus, Trager duck spleen necrosis virus, Viper retrovirus, Wooly monkey sarcoma virus, Jembrana disease virus, Puma lentivirus, Bovine foamy virus, Equine foamy virus, Feline foamy virus, Brown greater galago prosimian foamy virus, Bornean orangutan simian foamy virus, Central chimpanzee simian foamy virus, Cynomolgus macaque simian foamy virus, Eastern chimpanzee simian foamy virus. Grivet simian foamy virus, Guenon simian foamy virus, Japanese macaque simian foamy virus, Rhesus macaque simian foamy virus, Spider monkey simian foamy virus, Squirrel monkey simian foamy virus, Taiwanese macaque simian foamy virus, Western chimpanzee simian foamy virus, Western lowland gorilla simian foamy virus, White-tufted-ear marmoset simian foamy virus, Yellow-breasted capuchin simian foamy virus, or a combination thereof. In some embodiments, the nucleic acid sequences are based on nucleic acid sequences from HFV. In some embodiments, the nucleic acid sequences encoding the Pol polyprotein components and/or one or more accessory proteins are based on nucleic acid sequences from one or more lentiviruses. In some embodiments, the nucleic acid sequences encoding the Pol polyprotein components and/or one or more accessory proteins are based on nucleic acid sequences from: human immunodeficiency virus (HIV) (e.g., HIV-1, HIV-2), simian immunodeficiency virus (SIV), visna/maedi virus (VMV), caprine arthritis-encephalitis virus (CAEV), equine infectious anaemia virus (EIAV), feline immunodeficiency virus (FIV), bovine immunodeficiency virus (BIV), jembrana disease virus, puma lentivirus, or a combination thereof. In some embodiments, the nucleic acid sequences are based on nucleic acid sequences from HIV-1 (e.g., GenBank Accession No. AF033819). Nucleotide sequences from the HIV genome are available to the skilled artisan. See, e.g., HIV Genome Browser (Los Alamos National Laboratory): www.hiv.lanl.gov/content/sequence/genome_browser/browser and "Numbering positions in HXB2": Korber et al—Journal unknown, affiliated with UCSD and referenced by LANL database. An in-depth annotation resource for identifying genes within HIV is also provided at www.hiv.lanl.gov/content/sequence/HIV/MAP/annotation.

It will be understood that the terms "based on" or "derived from" indicate that the nucleic acid sequence (or amino acid sequence) may comprise one or more modifications relative to a base sequence. Thus, the nucleic acid sequences may comprise one or more modifications (e.g., a deletion of one or more nucleotides, an addition of one or more nucleotides, a substitution of one or more nucleotides, or a combination thereof) relative to the corresponding wild-type nucleic acid sequence. In some embodiments, the nucleic acid sequences encoding the Pol polyprotein components and/or one or more accessory proteins have at least 60% identity (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 9%, 96%, 95%, 98%, or 99% identity) to the corresponding wild-type nucleic acid sequence. In some aspects, the wild-type Pol polyprotein is from the HIV-1 strain NL4-3.

The one or more nucleic acid molecules encoding the Pol polyprotein components and/or one or more accessory proteins may comprise one or more chemical or biological modifications relative to a naturally occurring nucleic acid molecule. The modifications may enhance nucleic acid or protein stability and/or transcriptional/translational efficiency and/or reduce immunogenicity. The modifications may include, but are not limited to, modified nucleobases, modified backbones (e.g., phosphoramide, phosphorothioate, phosphorodithioate, O-methylphosphoramidite linkages and/or peptide nucleic acids).

In some embodiments, the one or more nucleic acid molecules encoding the Pol polyprotein components and/or one or more accessory proteins comprise one or more mutations that improve mRNA or corresponding mRNA stability. In some embodiments, the one or more nucleic acid molecules encoding the Pol polyprotein components and/or one or more accessory protein comprise one or more mutations that improve Rev independence. In some embodiments, the nucleic acid sequences comprise mutations (e.g., a deletion of one or more nucleotides, an addition of one or more nucleotides, a substitution of one or more nucleotides, or a combination thereof) in one or more intrinsic instability (INS) elements. In some embodiments, a codon in an INS element is replaced with an alternate codon to preserve the protein sequence, while altering or removing the INS element. In some embodiments, the INS elements are replaced with codons optimized for expression in humans. In some embodiments, one or more INS elements are selected from TAGAT, ATAGA, AAAAG, ATAAA, and TTATA, or other INS elements (e.g., those described in Wolff et al. *Nucleic Acids Res.* 31(11):2839-51 (2003)). In some embodiments, INS elements are completely removed. In some embodiments, INS elements are partially removed. In some embodiments, the nucleic acid sequences are codon optimized for expression in a human. These modifications may be present in nucleotide sequences encoding one or more of reverse transcriptase, integrase, capsid, matrix, nucleocapsid, p6, Vif, Nef, Vpu, or Vpr.

In some embodiments, the one or more nucleic acid molecules encoding the Pol polyprotein components and/or one or more accessory proteins comprise one or more mutations that improve the stability of the corresponding protein. In some embodiments, a nucleic acid molecule of the disclosure encodes an integrase polypeptide comprising a stabilizing methionine-glycine dipeptide. In some embodiments, a nucleic acid of the disclosure encodes an integrase polypeptide comprising an N-terminal methionine-glycine dipeptide.

In some embodiments, the one or more nucleic acid molecules encoding the Pol polyprotein components and/or one or more accessory proteins comprise one or more mutations that improve translation efficiency in host cells. In some embodiments, the codons of the nucleic acid molecule of the disclosure are optimized for expression in a human.

In some embodiments, the one or more nucleic acid molecules encoding the Pol polyprotein components and/or one or more accessory proteins comprise one or more modifications selected from: codon optimization for expression in a host cell (e.g., human or other mammalian or avian cell), partial or complete remove of INS elements, and modification of integrase with a stabilizing methionine-glycine dipeptide. In some embodiments, the one or more nucleic acid molecules encoding the Pol polyprotein components and/or one or more accessory proteins are codon optimized for expression in a host cell (e.g., human or other mammalian or avian cell), comprise complete or partial removal of INS elements, and encode an integrase polypeptide modified with a methionine-glycine dipeptide.

Figure 10:
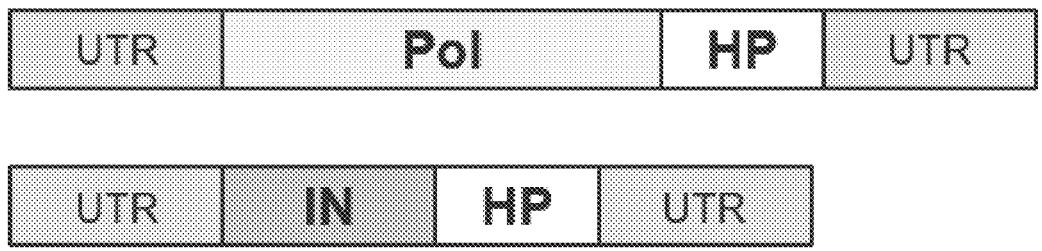
FIG. 10 illustrates an exemplary embodiment where integrase is fused to a homing protein for site-directed genome integration. Integrase may be fused to a homing protein when expressed as a part of the Pol polyprotein or when expressed as an individual unit.

In some embodiments, the one or more nucleic acid molecules encoding the Pol polyprotein components encode an integrase fused to a homing protein for site-directed genome integration (FIG. 10). A homing protein recognizes specific DNA sequences and thus directs the integrase to a specific sequence. This approach has the potential to be less genotoxic. In some embodiments, integrase is encoded by the Pol polyprotein. In some embodiments, the integrase is encoded as a separate unit. In some embodiments, the Pol polyprotein is fused to a homing protein. In some embodiments, a homing protein targets the genomic locus of the transgene. In some embodiments, a homing protein is an enzyme that recognizes a restriction site. Enzymes that recognize restriction sites are known in that art. See, e.g., www.neb.com/tools-and-resources/selection-charts/alpha-betized-list-of-recognition-specificities. Non-limiting examples of enzymes that recognize restrictions sites include, but are not limited to, AatII, AbaSI, Acc65I, AccI, AciI, AclI, AcuI, AfeI, AflII, AflIII, AgeI, AhdI, AleI-v2, AluI, AlwI, AlwNI, ApaI, ApaLI, ApoI, AscI, AseI, AsiSI, AvaI, BsoBI, AvaII, AvrII, BaeGI, BaeI, BamHI, BanI, BanII, BbsI, BbvCI, BbvI, BccI, BceAI, BcgI, BciVI, BclI, BfaI, BglI, BglII, BlpI, BmgBI, BmrI, BmtI, BpmI, BpuEI, Bpu10I, BsaAI, BsaBI, BsaHI, BsaJI, BsaWI, BsaXI, BseRI, BseYI, BsgI, BsiEI, BsiHKAI, BsiWI, BslI, BsmAI BcoDI, BsmBI-v2, BsmFI, BsmI, BspCNI, BspEI, BspHI, Bsp1286I, BspMI, BfuAI, BsrBI, BsrDI, BsrFI-v2, BsrGI, BssHII, BssSI-v2, BstAPI, BstBI, BstEII, BstNI, BstUI, BstXI, BstYI, Bsu36I, BtgI, BtgZI, BtsCI, BtsIMutI, BtsI-v2, Cac8I, ClaI, BspDI, CspCI, CviAII, CviKI-1, CviQI, DdeI, DpnI, DraI, DrdI, EaeI, EarI, EciI, Eco53kI, EcoNI, EcoO109I, EcoP15I, EcoRI, EcoRV, Esp3I, FatI, FauI, Fnu4HI, FokI, FseI, FspEI, FspI, HaeII, HaeIII, HgaI, HhaI, HincII, HindIII, HinfI, HinPII, HpaI, HphI, HpyAV, HpyCH4III, HpyCH4IV, HpyCH4V, Hpy99I, Hpy188I, Hpy166II, Hpy188III, I-CeuI, I-SceI, KasI, KpnI, LpnPI, MboI, Sau3AI, DpnII, MboII, MfeI, MluCI, MluI, MlyI, MmeI, MnlI, MscI, MseI, MslI, MspA1I, MspI, HpaII, MspJI, MwoI, NaeI, NarI, Nb.BbvCI, Nb.BsmI, Nb.BsrDI, Nb.BssSI. Nb.BtsI, NcoI, NdeI, NgoMIV, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaqCI, PciI, PflMI, PI-PspI, PI-SceI, PleI, PluTI, PmeI, PmlI, PpuMI, PshAI, PsiI-v2, PspGI, PspOMI, PspXI. PstI. PvuI, PvuII, RsaI, RsrII, SacI, SacII, SalI, SapI BspQI, Sau96I, SbfI, ScrFI, SexAI, SfaNI, SfcI, SfiI, SfoI, SgrAI, SmaI, SmlI, SnaBI, SpeI, SphI, SrfI, SspI, StuI, StyD4I, SwaI, TaqI-v2, TfiI, TseI, ApeKI, Tsp45I, TspRI, Tth111I, PflFI, XbaI, XcmI, XhoI, PaeR7I, XmaI, TspMI, XmnI, and ZraI. In some embodiments, a homing protein is a homing endonuclease. Homing endonucleases are known in the art, such as those disclosed in Stoddard, B. I., *Homing endonucleases from mobile group 1 introns: discovery to genome engineering.* Mobile DNA 5, 7 (2014). Non-limiting examples of homing endonucleases include I-TevI, I-HmuI, I-Bth035I, I-CreI, I-AniI, I-PpoI, and I-Ssp6803I. In some embodiments, the homing protein is I-PpoI. In some embodiments, the homing protein may be modified to remove any unwanted nuclease activity to prevent any genomic damage. In some embodiments, the homing protein is I-PpoI(N119A) or the like. In some embodiments, the integrase polypeptide is modified to remove any unwanted nuclease activity. In some embodiments, the integrase polypeptide comprises a D64V mutation or the like.

In certain embodiments, the nucleic acid molecules encoding the Pol polyprotein components and/or one or more accessory proteins are RNA molecules (e.g., ssRNA molecules such as mRNA molecules). In some embodiments, the RNA molecule comprising a 5' UTR, a nucleic acid sequence encoding a retroviral Pol polyprotein, and a 3' UTR provides the RT and integrase functions. In some embodiments, a nucleic acid molecule comprising a 5' UTR, nucleic acid sequences encoding individual Pol polyprotein components, and a 3' UTR provides the RT and integrase functions. In some embodiments, all Pol polyprotein components are encoded on one RNA molecule with a 5' and 3' UTR. In some embodiments, the Pol polyprotein components are encoded on two or more RNA molecules each with a 5' and 3' UTR. In some embodiments, the Pol polyprotein components are encoded on one or more RNA molecules each with a 5' and 3' UTR and are separated by one or more polycistronic elements. The one or more polycistronic elements may be IRESes and/or 2A peptide-encoding sequences and/or other polycistronic elements. In some embodiments, the RNA molecules do not encode the Pol polyprotein protease, for example when the Pol polyprotein components for RT and integrase are encoded on separate RNA molecules or are separated by polycistronic elements such as intervening IRESes and/or 2A peptide-encoding sequences, and/or other polycistronic elements. In some embodiments, nucleic acid molecules encoding one or more accessory proteins to enhance reverse transcription and/or integration are additionally present. In some embodiments, the one or more accessory proteins are encoded in cis (i.e., encoded by the same RNA molecule) with one or more Pol polyprotein components. In some embodiments, the one or more accessory proteins are encoded in cis with all Pol polyprotein components. In some embodiments, the one or more accessory proteins are encoded in cis with the Pol polyprotein. Thus, in some embodiments, all Pol polyprotein components and accessory proteins are encoded on one RNA molecule with a 5' and 3' UTR. In some embodiments, the nucleotide sequences encoding the Pol polyprotein components and/or the accessory proteins are separated by one or more one or more polycistronic elements such as IRESes and/or 2A peptide-encoding sequences, and/or other polycistronic elements. In some embodiments, the one or more accessory proteins are encoded in trans (i.e., encoded by a separate nucleic acid molecule) from the Pol polyprotein components. In some embodiments, each of the Pol polyprotein components and accessory proteins are encoded by two or more (e.g., two, three, four, or five, or more) RNA molecules, each with a 5' and 3' UTR In some embodiments, the UTRs include 3' or 5' sequences from mRNA molecules which are stable (including, but not limited to, globin, actin, GAPDH, tubulin, histone, or citric acid cycle enzymes).

In some embodiments, the nucleic acid molecules or compositions of the disclosure are capable of integrating the one or more transgenes into the host genome in the absence of functional retroviral Rev and/or Env proteins. In some embodiments, the compositions of the disclosure do not contain nucleic acid sequences that express proteins encoded by at least one of; retroviral rev gene and retroviral env gene. In some embodiments, the nucleic acid molecules or compositions of the disclosure do not contain nucleic acid sequences that express proteins encoded by both retroviral rev and env genes. In some embodiments, the compositions of the disclosure do not contain nucleic acid sequences encoding the following retroviral Gag proteins: MA, SP1, SP2, and p6. In some embodiments, the compositions of the disclosure do not comprise any nucleic acid sequences encoding retroviral Gag proteins. In other embodiments, the compositions of the disclosure do not comprise nucleic acid sequences that are able to express all retroviral Gag proteins.

In some embodiments, the RNA molecules encoding retroviral Pol polyprotein components and/or one or more accessory proteins comprise one or more modified ribonucleosides. In some embodiments, the modified ribonucleoside is selected from 2-thiouridine, 5-azauridine, pseudouridine, 4-thiouridine, 5-methyluridine, 5-methylpseudouridine, 5-aminouridine, 5-aminopseudouridine, 5-hydroxyuridine, 5-hydroxypseudouridine, 5-methoxyuridine, 5-methoxypseudouridine, 5-ethoxyuridine, 5-ethoxypseudouridine, 5-hydroxymethyluridine, 5-hydroxymethylpseudouridine, 5-carboxyuridine, 5-carboxypseudouridine, 5-formyluridine, 5-formylpseudouridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methoxycytidine, 5-ethoxycytidine, 5-hydroxymethylcytidine, 5-carboxycytidine, 5-formylcytydine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine. 2-thio-5-hydroxycytidine, 2-thio-5-methyl-5-azacytidine. 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine. N4-methyl-5-amino-5-azacytidine, N4-methyl-5-hydroxy-5-azacytidine. N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine. N4-amino-5-methylcytidine. N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine. 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine. 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine. 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine. N6-amino-7-deazaadenosine, N6-amino-8-azaadenosine, N6-amino-7-deaza-8-azaadenosine. N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, 6-thio-7-deaza-8-azaguanosin, and N1-methylpseudouridine. In some embodiments, the modified ribonucleoside is pseudouridine or a derivative of pseudouridine. In some embodiments, the derivative of pseudouridine is N1-methylpseudouridine. In some embodiments, the modified ribonucleoside is N6-methyladenosine.

In some embodiments, the RNA molecules encoding retroviral Pol polyprotein components and/or one or more accessory proteins comprise one or more modifications including, but not limited to: a 5' terminal cap (e.g., a 5'-7mG cap structure); inclusion of a poly(rA) tail; alteration of the 3' UTR or the 5' UTR; complexing the mRNA with an agent (e.g., a protein or a complementary nucleic acid molecule); inclusion of elements which change the structure of an mRNA molecule (e.g., which form secondary structures); and reduction of the number of C and/or U residues. In some embodiments, the poly(rA) sequence is from about 10-500 nucleotides. In some embodiments, the poly(rA) sequence is at least 10, at least 20, at least 30, at least 40, at least 50, at least 60, at least 70, at least 80, at least 90, at least 100, at least 200, at least 300, at least 400, or at least 500 nucleotides. Other chemical and biological modifications to RNA molecules are known in the art.

Pol Polyprotein Component and Accessory Protein Nucleic Acid Templates

In one aspect, the disclosure also provides nucleic acid templates (e.g., a recombinant DNA construct) for the production of the nucleic acid molecules encoding the Pol polyprotein components and/or one or more accessory proteins described herein. In some embodiments, the nucleic acid templates are used to produce RNA molecules. In some embodiments, the RNA molecules are produced using cell-free methods (e.g., in vitro transcription or cell-free RNA synthesis). See. e.g., US Patent Publications No. 2017-0292138, 2018-0087045 2019-0144489, incorporated herein by reference in their entireties. In some embodiments, a nucleic acid template comprises a 5' UTR, a nucleic acid sequence encoding one or more Pol polyprotein components, and a 3' UTR, in addition to RNA production elements (e.g., a T7 promoter, digestion sites, etc.). In some embodiments, a nucleic acid template comprises a T7 promoter, a 5' UTR, a nucleic acid sequence encoding a retroviral Pol polyprotein, and a 3' UTR, and optionally, one or more restriction digestion sites for template linearization. In some embodiments, a nucleic acid template comprises a T7 promoter, a 5' UTR, nucleic acid sequences encoding individual Pol polyprotein components, and a 3' UTR, and optionally, one or more restriction digestion sites for template linearization. In some embodiments, two or more nucleic acid templates, each with a T7 promoter, and a 5' and 3' UTR, encode the Pol polyprotein components. In some embodiments, one or more templates, each with a T7 promoter, and a 5' and 3' UTR, encode the Pol polyprotein components, wherein the Pol polyprotein components are separated by one or more polycistronic elements. The one or more polycistronic elements may be IRESes and/or 2A peptide-encoding sequences, and/or other polycistronic elements. In some embodiments, the nucleic acid templates do not encode the Pol polyprotein protease.

In some embodiments, the nucleic acid templates additionally comprise nucleic acid sequences encoding one or more accessory retroviral proteins to enhance reverse transcription and/or integration. In some embodiments, the one or more accessory proteins are encoded in cis (i.e., encoded by the same nucleic acid molecule) with one or more Pol polyprotein components. In some embodiments, the one or more accessory proteins are encoded in cis with all Pol polyprotein components. In some embodiments, the one or more accessory proteins are encoded in cis with the Pol polyprotein. In some embodiments, one nucleic acid template encodes all Pol polyprotein components and accessory proteins. In some embodiments, the nucleotide sequences encoding the Pol polyprotein components and/or the accessory proteins are separated by one or more polycistronic elements. The polycistronic elements may be IRESes and/or 2A peptide-encoding sequences, and/or other polycistronic elements. In some embodiments, the one or more accessory proteins are encoded in trans (i.e., encoded by a separate nucleic acid molecule) from the Pol polyprotein components. In some embodiments, each of the Pol polyprotein components and accessory proteins are encoded by two or more (e.g., two, three, four, or five, or more) nucleic acid templates, each with a T7 promoter, and a 5' and 3' UTR. In some embodiments, nucleic acid template comprises a T7 promoter, a 5' UTR, a nucleic acid sequence encoding agag-pol gene, a 3' UTR, and optionally, one or more restriction digestion sites for template linearization. In some embodiments, a nucleic acid template comprises a T7 promoter, a 5' UTR, a nucleic acid sequence encoding a gag-pol gene comprising a frameshift mutation, a 3' UTR, and optionally, one or more restriction digestion sites for template linearization. In some embodiments, the gag-pol gene does not encode the matrix protein.

In some embodiments, the UTRs include 3' or 5' sequences from mRNA molecules which are stable and highly translated (including, but not limited to, globin, actin, GAPDH, tubulin, histone, or citric acid cycle enzymes).

Figure 4:
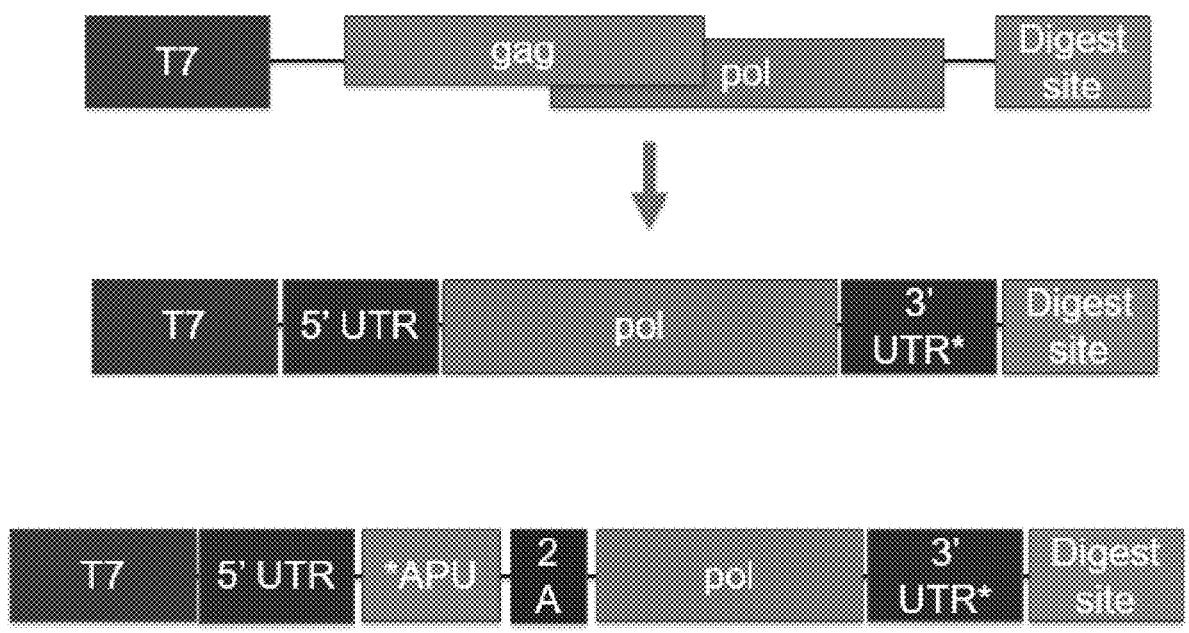
FIG. 4 is a schematic which illustrates an exemplary embodiment of a reverse transcription and integration complex design, compared to the canonical design. The Pol polyprotein is produced from a separate construct as compared to the inline gag/pol design from the canonical design so translational slippage is no longer required. In some embodiments, one or more accessory retroviral proteins are encoded in cis with the Pol polyprotein. RNA production elements include an RNA polymerase promoter (e.g., the T7 RNA polymerase promoter) and optionally, one or more restriction digestion sites for template linearization.

In some embodiments, the nucleic acid templates do not contain nucleic acid sequences that express proteins encoded by retroviral rev and env genes. In some embodiments, the nucleic acid templates do not comprise nucleic acid sequences encoding the following retroviral Gag proteins: MA, SP1, SP2, and p6. In some embodiments, the nucleic acid templates do not comprise nucleic acid sequences encoding MA. In some embodiments, the nucleic acid templates comprise nucleic acid sequences encoding one or more of NC and CA. In some embodiments, the compositions of the disclosure do not comprise any nucleic acid sequences encoding retroviral Gag proteins (MA, CA, NC, SP1, SP2, P6). In other embodiments, the compositions of the disclosure do not comprise nucleic acid sequences that are able to express all retroviral Gag proteins. In some embodiments, the nucleic acid templates comprise nucleic acid sequences encoding one or more of NC, CA, MA, p6, Vif, Tat, Nef, Vpr, and Vpu. Exemplary nucleic acid templates encoding Pol polyproteins and/or accessory proteins are shown in FIGS. 4-5. In some embodiments, the RNA molecules are produced using cell-free methods (e.g., in vitro transcription, cell-free RNA synthesis).

Transgene-Encoding Nucleic Acid

In one aspect, the disclosure provides a nucleic acid molecule comprising one or more transgenes flanked by LTR sequences, which facilitate integration of the one or more transgenes into the host genome. The nucleic acid molecule may not comprise a viral packaging signal (e.g., the Psi packaging element) and/or a Rev response element (RRE). Thus, the transgene-encoding nucleic acid molecule encodes the one or more transgenes and contains the sequences that will assist in integrating the one or more transgenes into the host cell genome; however, the system does not allow for the production of any viral particles. In some embodiments, the transgene-encoding nucleic acid molecule comprises one or more reverse transcriptase priming elements and one or more promoter sequences operably linked to one or more transgenes, between a 5' LTR and a 3' LTR.

The term "long terminal repeat" or "LTR", as used herein, refers to the sequences of RNA or DNA that repeat hundreds or thousands of times and is found at either end of proviral DNA formed by reverse transcription of retroviral RNA. LTRs are used by viruses to integrate their genetic material into host genomes (e.g., the ends of the LTRs participate in integration of the provirus into the host genome). In some embodiments, the LTRs are self-inactivating. The 3' LTR may have a deletion (e.g., a deletion of the transcriptional enhancers or the enhancers and promoter in the U3 region of the 3' LTR) that is transferred to the 5' LTR after a single round of reverse transcription. The deletion in the 3' LTR (e.g., a deletion of the transcriptional enhancers or the enhancers and promoter in the U3 region of the 3' LTR) may be 10-50, 50-100, 100-150, 150-200, or more nucleotides. In some embodiments, the deletion in the 3' LTR is 100-150 nucleotides. In some embodiments, the deletion in the 3' LTR is 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleotides. In some embodiments, the LTRs, Pol polyprotein components, and/or one or more accessory proteins are based on nucleic acid sequences from the same retrovirus. In some embodiments, the LTRs, the Pol polyprotein components and/or one or more accessory proteins are based on nucleic acid sequences from two or more different retroviruses. In some embodiments, the LTRs are based on LTRs from murine leukemia virus (MLV), Moloney murine leukemia virus (MoLV), Friend virus (FV), Abelson murine leukemia virus (A-MLV), murine stem cell virus (MSCV), mouse mammary tumor virus (MMTV), Moloney murine sarcoma virus (MoMSV), Rous sarcoma virus (RSV), Fujinami sarcoma virus (FuSV), FBR murine osteosarcoma virus (FBR MSV), Avian myelocytomatosis virus-29 (MC29), Avian erythroblastosis virus (AEV), human T-cell leukemia virus (HTLV), avian sarcoma leukosis virus (ASLV), endogenous xenotropic MuLV-related virus VP62 (XMRV), primate T-lymphotropic virus (PTLV), walleye dermal sarcoma virus (WDSV), the human foamy virus (HFV), Friend MLV (FrMLV), Avian sarcoma virus (ASV), Avian leukosis virus, Avian myeloblastosis virus, UR2 sarcoma virus, Y73 sarcoma virus, Jaagsiekte sheep retrovirus. Langur virus, Mason-pfizer monkey virus, Squirrel monkey retrovirus, Avian carcinoma mill hill virus 2, Bovine leukemia virus, Primate T-lymphotropic virus 1, Primate T-lymphotropic virus 2. Primate T-lymphotropic virus 3, Walleye dermal sarcoma virus, Walleye epidermal hyperplasia virus 1, Walleye epidermal hyperplasia virus 2. Chick syncytial virus. Feline leukemia virus, Finkel-Biskis-Jinkins murine sarcoma virus, Gardner-Amstein feline sarcoma virus, Gibbon ape leukemia virus, Guinea pig type-C oncovirus, Hardy-Zuckerman feline sarcoma virus, Harvey murine sarcoma virus, Kirsten murine sarcoma virus, Koala retrovirus, Moloney murine sarcoma virus, Porcine type-C oncovirus, Reticuloendotheliosis virus, Snyder-Theilen feline sarcoma virus, Trager duck spleen necrosis virus, Viper retrovirus, Wooly monkey sarcoma virus, Jembrana disease virus, Puma lentivirus, Bovine foamy virus. Equine foamy virus. Feline foamy virus, Brown greater galago prosimian foamy virus, Bornean orangutan simian foamy virus, Central chimpanzee simian foamy virus, Cynomolgus macaque simian foamy virus, Eastern chimpanzee simian foamy virus, Grivet simian foamy virus, Guenon simian foamy virus, Japanese macaque simian foamy virus, Rhesus macaque simian foamy virus, Spider monkey simian foamy virus, Squirrel monkey simian foamy virus. Taiwanese macaque simian foamy virus, Western chimpanzee simian foamy virus, Western lowland gorilla simian foamy virus, White-tufted-ear marmoset simian foamy virus, Yellow-breasted capuchin simian foamy virus, or a combination thereof. In some embodiments, the LTRs are based on LTRs from HFV. In some embodiments, the LTRs are lentiviral LTRs. In some embodiments, the lentiviral LTRs are based on LTRs from: human immunodeficiency virus (HIV) (e.g., HIV-1, HIV-2), simian immunodeficiency virus (SIV), visna/maedi virus (VMV), caprine arthritis-encephalitis virus (CAEV), equine infectious anaemia virus (EIAV), feline immunodeficiency virus (FIV), bovine immunodeficiency virus (BIV), jembrana disease virus, puma lentivirus, or a combination thereof. In some embodiments, the LTRs are based on LTRs from HIV-1 (e.g., HIV-1 with the genomic sequence in GenBank Accession No. AF033819). Other LTRs can be found in the art, for example on GenBank, as described above.

It will be understood that the terms "based on" or "derived from" indicate that the nucleic acid sequence may comprise one or more modifications relative to a base sequence. Thus, the LTRs may comprise one or more modifications (e.g., a deletion of one or more nucleotides, an addition of one or more nucleotides, a substitution of one or more nucleotides, or a combination thereof) relative to the corresponding wild-type nucleic acid sequence.

In some embodiments, the LTRs have at least 60% identity (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 9%, 96%, 95%, 98%, or 99% identity) to the wild-type LTRs.

HIV-1 RT depends on cytoplasmic tRNAs for priming of the viral genome prior to the reverse transcription reaction. In some embodiments, the transgene-encoding nucleic acid molecule may comprise one or more reverse transcriptase priming elements (e.g., 1, 2, 3, 4, 5, 6, 7, 8, 9, 10, or more).

In some embodiments, a reverse transcriptase priming element is a binding site for an endogenous tRNA. In some embodiments, the priming element is a binding site for lysyl tRNA. In some embodiments, a reverse transcriptase priming element is a synthetic primer binding site. In some embodiments, a reverse transcriptase priming element is a synthetic primer binding site, and one or more synthetic primers are provided for use in conjunction with the transgene-encoding nucleic acid molecule and the nucleic acid molecules encoding the Pol polyprotein components. A synthetic primer is a non-naturally occurring primer based on rational design. It will be understood that the synthetic primer may be based on naturally occurring sequences. A synthetic primer binding site is the complementary sequence. In some embodiments, a nucleic acid molecule of the disclosure is primed with one or more RNA or DNA priming oligonucleotides prior to delivery to target cells. In some embodiments, a nucleic acid molecule of the disclosure is co-delivered with one or more short RNA or DNA priming oligonucleotides. In some embodiments, an RNA or DNA priming oligonucleotide is 5-10, 10-15, 15-20, 20-25, 25-30, 5-15, 5-20, 5-25, 5-30, 10-20, 10-25, 10-30, 15-25, or 15-30 nucleotides in length. In some embodiments, an RNA or DNA priming oligonucleotide is 5, 6, 7, 8, 9, 10, 11, 12, 13, 14, 15, 16, 17, 18, 19, 20, 21, 22, 23, 24, 25, 26, 27, 28, 29, or 30 nucleotides in length. In some embodiments, the RNA or DNA priming oligonucleotides may be 30-50 or 50-80 or 80-100, 100-150, or up to about 200 nucleotides. In some embodiments, the RNA or DNA priming oligonucleotides may be about 70-80 nucleotides. In some embodiments, the RNA or DNA priming oligonucleotides may be about 70, 71, 72, 73, 74, 75, 76, 77, 78, 79, or 80 nucleotides. In some embodiments, the RNA or DNA priming oligonucleotides may be about 76 nucleotides. In some embodiments, the priming oligonucleotide is an engineered oligonucleotide that is complementary to the RT priming element. In some embodiments, the priming oligonucleotide is GUCCCUGUUCGGGCGCCA (SEQ ID NO: 18) or GTCCCTGTTCGGGCGCCA (SEQ ID NO: 19).

Expression of the one or more transgenes may be controlled using one or more control sequences operably linked to the one or more transgenes, wherein the control sequences include promoters, enhancers, and other regulatory sequences. In some embodiments, the transfer nucleic acid comprises a single transgene linked to a promoter. In some embodiments, the transfer nucleic acid comprises two or more transgenes. In some embodiments, each transgene is operably linked to its own promoter. In some embodiments, a single promoter is operably linked to two or more transgenes. In some embodiments, some transgenes of the two or more transgenes are operably linked to their own promoters, and some transgenes of the two or more transgenes are operably linked to a common promoter.

The two or more transgenes may be separated by one or more polycistronic elements. The one or more polycistronic elements may be one or more IRESes and/or one or more 2A peptide-encoding sequences, and/or other polycistronic elements. An IRES is a nucleotide sequence that allows for the initiation of protein translation in the middle of a messenger RNA (mRNA) sequence. A 2A peptide is a small (18-22 amino acids) sequence that allows for efficient, stoichiometric production of discrete protein products within a single reading frame through a ribosomal skipping event within the 2A peptide sequence. Any other polycistronic element that will facilitate translation could also be used.

Any promoters functional in eukaryotic cells may be used in the present invention. In some embodiments, a promoter may be one that is naturally associated with the transgene, and may be obtained by isolating the 5' non-coding sequence upstream of the coding segment and/or exon of a given gene. Such a promoter may be referred to as an endogenous promoter or a native promoter. In other embodiments, a transgene may be positioned under the control of a recombinant or heterologous promoter, which refers to a promoter that is not normally associated with the encoded nucleic acid sequence in its natural environment. In some embodiments, the promoter is tissue-specific or cell-specific (e.g., specific for bone marrow, hematopoietic stem cells (HSCs), T cells, liver, ocular tissue, or muscle, etc.). In some embodiments, the promoter is a constitutively active promoter. In some embodiments, the promoter is an inducible promoter. In some embodiments, the promoter may be a chimeric promoter comprising sequence elements from two or more different promoters. Suitable promoters include promoters derived from the genomes of viruses, such as polyoma virus, adenovirus, fowlpox virus, bovine papilloma virus, avian sarcoma virus, cytomegalovirus (CMV) (e.g., hCMV, mCMV), Rous sarcoma virus (RSV), and simian Virus 40 (SV40), or from heterologous mammalian promoters, such as the actin promoter, human elongation factor-1 alpha (EF1a) promoter, CAG promoter, thymidine kinase (TK) promoter, ubiquitin promoter, human phosphoglycerate kinase (PGK) promoter, human glyceraldehyde-3-phosphate dehydrogenase (GAPDH) promoter, or ribosomal protein promoter. Alternatively, tissue-specific promoters, such as rhodopsin (Rho) promoter, rhodopsin kinase (RhoK) promoter, cone-rod homeobox containing gene (CRX) promoter, neural retina-specific leucine zipper protein (NRL) promoter, Vitelliform Macular Dystrophy 2 (VMD2) promoter, tyrosine hydroxylase promoter, neuronal-specific enolase (NSE) promoter, astrocyte-specific glial fibrillary acidic protein (GFAP) promoter, human al-antitrypsin (hAAT) promoter, phosphoenolpyruvate carboxykinase (PEPCK) promoter, liver fatty acid binding protein promoter, Flt-1 promoter, IFN-β promoter (e.g., mIFN-β promoter). Mb promoter, SP-B promoter, SYN1 promoter, WASP promoter, SV40/hAlb promoter, SV40/CD43, SV40/CD45, NSE/RU5' promoter, ICAM-2 promoter, GPIIb promoter, GFAP promoter, fibronectin promoter, endoglin promoter, elastase-1 promoter, desmin promoter, B29 promoter, CD14 promoter, CD43 promoter, CD45 promoter, CD68 promoter, NphsI promoter, OG-2 promoter, and mNUS promoter may be used to drive transcription. In some embodiments, the promoter is a hCMV promoter.

Transcription of the one or more transgenes may be increased or modulated further by inserting one or more enhancer sequences into the transgene-encoding nucleic acid molecule. The enhancer may be positioned 5' or 3' to the promoter. Suitable enhancers may include an enhancer from a eukaryotic cell virus, such as the SV40 enhancer, the CMV early promoter enhancer, or the woodchuck hepatitis virus posttranscriptional regulatory element (WPRE). In some embodiments, the enhancer is a WPRE.

In some embodiments, a transgene-encoding nucleic acid molecule comprises a 5' LTR, one or more reverse transcriptase priming elements, one or more promoters operably linked to one or more transgenes, and a 3' LTR. In some embodiments, the promoter is a hCMV promoter. In some embodiments, the transgene-encoding nucleic acid molecule further comprises one or more enhancers operably linked to the promoters and/or transgenes. In some embodiments, the enhancer is a WPRE element. In some embodiments, a transgene encoding nucleic acid molecule comprises a 5' LTR, one or more reverse transcriptase priming elements, a promoter operably linked to a transgene, an enhancer, and a 3' LTR. In some embodiments, a transgene-encoding nucleic acid molecule comprises a 5' LTR, one or more reverse transcriptase priming elements, a hCMV promoter operably linked to a transgene, a WPRE enhancer, and a 3' LTR.

The transgene-encoding nucleic acid molecule may comprise one or more chemical or biological modifications relative to a naturally occurring nucleic acid molecule. The modifications may enhance stability and/or transcriptional/translational efficiency and/or reduce immunogenicity. The modifications may include, but are not limited to, modified nucleobases, modified backbones (e.g., phosphoramide, phosphorothioate, phosphorodithioate, O-methylphosphoramidite linkages and/or peptide nucleic acids).

In some embodiments, the transgene-encoding nucleic acid molecule is an RNA molecule (e.g., ssRNA molecule). In some embodiments, a transgene-encoding RNA molecule comprises a 5' LTR, one or more reverse transcriptase priming elements, one or more promoters operably linked to one or more transgenes, and a 3' LTR. In some embodiments, the promoter is a hCMV promoter. In some embodiments, the transgene-encoding RNA further comprises one or more enhancers operably linked to the promoters and/or transgenes. In some embodiments, the enhancer is a WPRE element. In some embodiments, a transgene-encoding RNA molecule comprises a 5' LTR, one or more reverse transcriptase priming elements, a promoter operably linked to a transgene, an enhancer, and a 3' LTR. In some embodiments, a transgene-encoding RNA molecule comprises a 5' LTR, one or more reverse transcriptase priming elements, a hCMV promoter operably linked to a transgene, a WPRE enhancer, and a 3' LTR.

In some embodiments, the transgene-encoding RNA molecule comprises one or more chemical or biological modifications relative to a naturally occurring RNA. In some embodiments, the transgene-encoding RNA molecule does not comprise any modified ribonucleosides. In some embodiments, the transgene-encoding RNA molecule comprises one or more modified ribonucleosides. Examples of suitable modified ribonucleosides are provided elsewhere in the description. In some embodiments, the RNA molecule comprises one or more modifications including but not limited to: modified ribonucleosides, a 5' terminal cap (e.g., a 5'-7mG cap structure); inclusion of a poly(rA) tail; complexing the mRNA with an agent (e.g., a protein or a complementary nucleic acid molecule); inclusion of elements which change the structure of an RNA molecule (e.g., which form secondary structures); and reduction of the number of C and/or U residues. In some embodiments, the poly(rA) sequence is from about 10-500 nucleotides. In some embodiments, the poly(rA) sequence is at least 10, at least 20, at least 30, at least 40, at least 50, at least 60, at least 70, at least 80, at least 90, at least 100, at least 200, at least 300, at least 400, or at least 500 nucleotides. In some embodiments, the transgene-encoding RNA molecule is not capped. Other chemical and biological modifications to RNA molecules are known in the art.

Transgene-Encoding Nucleic Acid Templates

Figure 3:
FIG. 3 is a schematic which outlines an exemplary embodiment of the transgene-encoding transfer nucleic acid design. RNA production elements include an RNA polymerase promoter (e.g., the T7 RNA polymerase promoter) and a restriction digestion site, for template linearization.

In one aspect, the disclosure also provides nucleic acid templates (e.g., a recombinant DNA construct) for the production of the transgene-encoding nucleic acid molecule. In some embodiments, the nucleic acid template is used to produce a transgene-encoding RNA molecule. In some embodiments, the transgene-encoding RNA molecule is produced using cell-free methods (e.g., in vitro transcription or cell-free RNA synthesis). See, e.g., US Patent Publications No. 20170292138, 20180087045 20190144489, incorporated by reference herein in their entireties. In some embodiments, the nucleic acid template comprises a 5' LTR, one or more reverse transcriptase priming elements, one or more promoters operably linked to one or more transgenes, and a 3' LTR, in addition to RNA production elements (e.g., a T7 promoter, digestion sites, etc.). In some embodiments, a nucleic acid template comprises a 17 promoter, a 5' LTR, one or more reverse transcriptase priming elements, one or more promoters operably linked to one or more transgenes, and a 3' LTR, and optionally, one or more restriction digestion sites for template linearization. In some embodiments, the promoter is a hCMV promoter. In some embodiments, the nucleic acid template further comprises one or more enhancers operably linked to the promoters and/or transgenes. In some embodiments, the enhancer is a WPRE element. In some embodiments, a nucleic acid template comprises a T7 promoter, a 5' LTR, one or more reverse transcriptase priming elements, a promoter operably linked to a transgene, an enhancer, a 3' LTR and optionally, one or more restriction digestion sites for template linearization. In some embodiments, a transgene-encoding nucleic acid template comprises a 5' LTR, one or more reverse transcriptase priming elements, a hCMV promoter operably linked to a transgene, a WPRE enhancer, a 3' LTR and optionally, one or more restriction digestion sites for template linearization. An exemplary nucleic acid template encoding a transgene-encoding nucleic acid molecule is shown in FIG. 3.

Transgenes

In some embodiments, the transgene-encoding nucleic acid molecule encodes one or more transgenes. In some embodiments, the transgene-encoding nucleic acid molecule encodes two or more transgenes (e.g., 2, 3, 4, 5, 6, 7, 8, 9, or 10 or more). In certain embodiments, the transgene-encoding nucleic acid molecule encodes only one transgene.

In some embodiments, a transgene encodes a therapeutic molecule, a diagnostic molecule, or reporter molecule.

In some embodiments, a transgene encodes a therapeutic molecule. The therapeutic molecule may be a nucleic acid or a polypeptide. Therapeutic molecules of the present disclosure may be used to, for example, replace a protein that is deficient or abnormal, augment an existing biological pathway, provide a novel function or activity, in a cell, tissue, organ, or subject. The therapeutic molecule may also be used to elicit an immune response. Exemplary types of transgenes include, but are not limited to, sequences encoding enzymes, co-factors, carrier proteins, transport proteins, cytokines, signaling proteins, suicide gene products, drug resistance proteins, tumor suppressor protein hormones, peptides with immunomodulatory properties, tolerogenic peptides, immunogenic peptides, antibodies and antigen-binding fragments thereof, anti-oxidant molecules, engineered immunoglobulin-like molecules, fusion proteins, immune co-stimulatory molecules, immunomodulatory molecules, chimeric antigen receptors, toxins, tumor suppressor proteins, growth factors, membrane proteins, receptors, vasoactive proteins, ligand proteins, antiviral proteins, ribozymes, RNAs, riboswitches, mRNA, RNA interference (e.g., shRNA, siRNA, microRNA) molecules, and derivatives thereof.

In some embodiments, therapeutic proteins encoded by the transgene include, but are not limited to, a cytokine, cystic fibrosis transmembrane conductance regulator protein (CFTR), dystrophin, utrophin, blood coagulation (clotting) factor (e.g., Factor XIII, Factor IX, Factor X, Factor VIII, Factor VIIa, protein C, Factor VII, B domain-deleted Factor VIII, or a high-activity or longer half-life variant of coagulation factor, or an active or inactive form of a coagulation factor), retinal pigment epithelium-specific 65 kDa protein (RPE65), erythropoietin, LDL receptor, lipoprotein lipase, ornithine transcarbamylase, beta-globin, alpha-globin, spectrin, alpha-antitrypsin, adenosine deaminase (ADA), a metal transporter (ATP7A or ATP7), sulfamidase, an enzyme involved in lysosomal storage disease, hypoxanthine guanine phosphoribosyl transferase, beta-25 glucocerebrosidase, sphingomyelinase, lysosomal hexosaminidase, branched-chain keto acid dehydrogenase, insulin-like growth factor 1 or 2, platelet derived growth factor, epidermal growth factor, nerve growth factor, neurotrophic factor-3 and -4, brain-derived neurotrophic factor, glial derived growth factor, transforming growth factor alpha and beta, alpha-interferon, beta-interferon, interferon-gamma, interleukin-2, interleukin-4, interleukin-12, granulocyte-macrophage colony stimulating factor, lymphotoxin, herpes simplex virus thymidine kinase, cytosine deaminase, diphtheria toxin, cytochrome P450, deoxycytidine kinase, tumor necrosis factor, p53, Rb, Wt-1, NFL, Von Hippel-Lindau (VHL), SERCA2a, adenomatous polyposis coli (APC), VEGF, microdystrophin, minidystrophin, lysosomal acid lipase, arylsulfatase A and B, ATP7A and B, insulin, glucokinase, guanylate cyclase 2D (GUCY2D), Rab escort protein 1, LCA 5, omithine ketoacid aminotransferase, Retinoschisis 1, USHIC, RP GTPase regulator (RPGR), MERTK, DFNB1, ACHM 2, 3 and 4, PKD-1 or PKD-2, TPP1, CLN2, a gene product implicated in lysosomal storage diseases (e.g., sulfatases, N-acetylglucosamine-1-phosphate transferase, cathepsin A, GM2-AP, NPC1, VPC2, a sphingolipid activator protein), and any other peptide or protein, or derivatives thereof that may have a therapeutic effect in a subject in need thereof.

It will be understood that the term "derivative thereof" includes any therapeutically or functionally active fragment, or modification of a base polypeptide. A derivative of a polypeptide may comprise one or more modifications (e.g., a deletion of one or more nucleotides, an addition of one or more nucleotides, a substitution of one or more nucleotides, or a combination thereof) relative to the corresponding wild-type polypeptide sequence. In some embodiments, a derivative is a homolog. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity. e.g., 30%, 40%, 50%, 60%, 70%, 80%, 90%, 95% or 99% or more can also be used to establish homology. In some embodiments, a derivative is a polypeptide that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to a base polypeptide. Methods for determining sequence similarity percentages are well known to those having ordinary skill in the art. In some embodiments, similarity can be determined using algorithms such as those described herein, including, for example, BLASTP and BLASTN algorithms, for example, using default parameters. In some aspects, the wild-type HIV-1 strain is NL4-3.

In some embodiments, the transgene encodes beta-globin or a derivative thereof. The beta-globin gene may be used for gene therapy to treat beta-thalassemia or sickle cell disease. In some embodiments, the beta-globin gene is a human beta-globin gene. In some embodiments, the transgene encoding beta-globin or a derivative thereof is operably linked to a hCMV promoter. In some embodiments, the transgene encoding beta-globin or a derivative thereof is operably linked to a tissue-specific or cell-specific promoter. In some embodiments, the promoter is specific for bone marrow or HSCs. In some embodiments, the transgene encoding beta-globin or a derivative thereof is operably linked to the native beta-globin promoter. In some embodiments, the transgene encoding beta-globin or a derivative thereof is further operably linked to a WPRE enhancer. In some embodiments, the transgene encodes a beta-globin polypeptide having the amino acid sequence corresponding to NCBI Reference Sequence No. NP_000509.1 or a fragment thereof. In some embodiments, the transgene encodes a beta-globin polypeptide having an amino acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94% 95%, 96%, 97%, 98%, 99%, or 100% identical) to NCBI Reference Sequence No. NP_000509.1 or a fragment thereof. In some embodiments, the transgene comprises a beta-globin gene having the nucleic acid sequence corresponding to NCBI Reference Sequence No. NM_000518.5 or a fragment thereof. In some embodiments, the transgene comprises a beta-globin gene having a nucleic acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NM_000518.5 or a fragment thereof.

In some embodiments, the transgene encodes CFTR or a derivative thereof. The CFTR gene may be used for gene therapy to treat cystic fibrosis. In some embodiments, the transgene encoding CFTR or a derivative thereof is operably linked to a hCMV promoter. In some embodiments, the transgene encoding CFTR or a derivative thereof is operably linked to a tissue-specific or cell-specific promoter. In some embodiments, the promoter is specific for epithelial cells. In some embodiments, the transgene encoding CFTR or a derivative thereof is operably linked to the native CFTR promoter. In some embodiments, the transgene encoding CFTR or a derivative thereof is further operably linked to a WPRE enhancer. In some embodiments, the transgene encodes a CFTR polypeptide having the amino acid sequence corresponding to NCBI Reference Sequence No. NP_000483.3 or a fragment thereof. In some embodiments, the transgene encodes a CFTR polypeptide having an amino acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NP_000483.3 or a fragment thereof. In some embodiments, the transgene comprises a CFTR gene having the nucleic acid sequence corresponding to NCBI Reference Sequence No. NM_000492.4 or a fragment thereof. In some embodiments, the transgene comprises a CFTR gene having a nucleic acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NM_000492.4 or a fragment thereof.

In some embodiments, the transgene encodes Factor VIII or a derivative thereof. The Factor VIII gene may be used for gene therapy to treat hemophilia B. In some embodiments, the Factor VIII gene is a human Factor VIII gene. In some embodiments, the transgene encoding Factor VIII or a derivative thereof is operably linked to a hCMV promoter. In some embodiments, the transgene encoding Factor VIII or a derivative thereof is operably linked to a tissue-specific or cell-specific promoter. In some embodiments, the promoter is specific for liver. In some embodiments, the promoter is specific for bone marrow or HSCs. In some embodiments, the transgene encoding Factor VIII or a derivative thereof is operably linked to the native Factor VIII promoter. In some embodiments, the transgene encoding Factor VIII or a derivative thereof is further operably linked to a WPRE enhancer. In some embodiments, the transgene encodes a Factor VIII polypeptide having the amino acid sequence corresponding to NCBI Reference Sequence No. NP_000123.1 or a fragment thereof. In some embodiments, the transgene encodes a Factor VIII polypeptide having the amino acid sequence corresponding to NCBI Reference Sequence No. NP_063916.1 or a fragment thereof. In some embodiments, the transgene encodes a Factor VIII polypeptide having an amino acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NP_000123.1 or NCBI Reference Sequence No. NP_063916.1 or a fragment thereof. In some embodiments, the transgene comprises a Factor VIII gene having the nucleic acid sequence corresponding to NCBI Reference Sequence No. NM_000132.4 or a fragment thereof. In some embodiments, the transgene comprises a Factor VIII gene having the nucleic acid sequence corresponding to NCBI Reference Sequence No. NM_019863.2 or a fragment thereof. In some embodiments, the transgene comprises a Factor VIII gene having a nucleic acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NM_000132.4 or NCBI Reference Sequence No. NM_019863.2, or a fragment thereof.

In some embodiments, the transgene encodes dystrophin or a derivative thereof. The dystrophin gene may be used for gene therapy to treat Duchenne Muscular Dystrophy (DMD). In some embodiments, the dystrophin gene is a micro-dystrophin or mini-dystrophin gene (Vincent et al., Nature Genetics 5:130 (1993); Wang et al., *Proc Natl Acad Sci USA* 97:13714-9 (2000) [mini-dystrophin]; Harper et al., Nat Med 8:253-61 (2002) [micro-dystrophin]). In some embodiments, the dystrophin gene is the human dystrophin gene. In some embodiments, the transgene encoding dystrophin or a derivative thereof is operably linked to a hCMV promoter. In some embodiments, the transgene encoding dystrophin or a derivative thereof is operably linked to a tissue-specific or cell-specific promoter. In some embodiments, the promoter is specific for muscle cells. In some embodiments, the transgene encoding dystrophin or a derivative thereof is operably linked to the native dystrophin promoter. In some embodiments, the transgene encoding dystrophin or a derivative thereof is further operably linked to a WPRE enhancer. In some embodiments, the transgene encodes a dystrophin polypeptide having the amino acid sequence corresponding to NCBI Reference Sequence No. NP_000100.3 or a fragment thereof. In some embodiments, the transgene encodes a dystrophin polypeptide having an amino acid sequence that is at least 60% identical (e.g., 70%, 80%, 90% to 100%, 95% to 100% f, 98% to 100% r, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NP_000100.3 or a fragment thereof. In some embodiments, the transgene comprises a dystrophin gene having the nucleic acid sequence corresponding to NCBI Reference Sequence No. NM_000109.4 or a fragment thereof. In some embodiments, the transgene comprises a dystrophin gene having a nucleic acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NM_000109.4 or a fragment thereof.

In some embodiments, the transgene encodes RP GTPase regulator (RPGR) or a derivative thereof. The RPGR gene may be used for gene therapy to retinitis pigmentosa. In some embodiments, the RPGR gene is the human RPGR gene. In some embodiments, the transgene encoding RPGR or a derivative thereof is operably linked to a hCMV promoter. In some embodiments, the transgene encoding RPGR or a derivative thereof is operably linked to a tissue-specific or cell-specific promoter. In some embodiments, the promoter is specific for ocular tissue. In some embodiments, the transgene encoding RPGR or a derivative thereof is operably linked to the native RPGR promoter. In some embodiments, the transgene encoding RPGR or a derivative thereof is further operably linked to a WPRE enhancer. In some embodiments, the transgene encodes a RPGR polypeptide having the amino acid sequence corresponding to NCBI Reference Sequence No. NP_000319.1 or a fragment thereof. In some embodiments, the transgene encodes a RPGR polypeptide having an amino acid sequence that is at least 60% identical (e.g., 70%, 80%, 90% to 100%, 95% to 100%, 98% to 100%, or 81%. 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NP_000319.1 or a fragment thereof. In some embodiments, the transgene comprises a RPGR gene having the nucleic acid sequence corresponding to NCBI Reference Sequence No. NM_000328.3 or a fragment thereof. In some embodiments, the transgene comprises a RPGR gene having a nucleic acid sequence that is at least 60% identical (e.g., 70%, 80%, 90% to 100%, 95% to 100%, 98% to 100%, or 81%, 82%, 83%, 84%, 85%, 86%, 87%, 88%, 89%, 90%, 91%, 92%, 93%, 94%, 95%, 96%, 97%, 98%, 99%, or 100% identical) to NCBI Reference Sequence No. NM_000328.3 or a fragment thereof.

In some embodiments, the transgene encodes a chimeric antigen receptor (CAR). The CAR may be used to treat cancer. In some embodiments, the transgene encoding the CAR is operably linked to a hCMV promoter. In some embodiments, the transgene encoding a CAR is operably linked to a tissue-specific or cell-specific promoter. In some embodiments, the promoter is specific for HSCs or T cells (e.g., cytotoxic T cells). In some embodiments, the transgene encoding the CAR is further operably linked to a WPRE enhancer.

In some embodiments, the transgene encodes a reporter molecule. The reporter molecule may be a nucleic acid or a polypeptide. A reporter molecule refers to a molecule that can be used to measure gene expression and generally produce a measurable signal such as fluorescence, luminescence, or color. In some embodiments, the polypeptide is luciferase. In some embodiments, the polypeptide is a fluorescent protein. Fluorescent proteins are known in the art, and are a subclass of fluorophores, which are fluorescent chemical compounds with the ability to re-emit light upon excitation. The fluorophore will absorb excitation light energy of a first specific wavelength, and then will re-emit light energy at a second, longer specific wavelength. Each type of fluorophore responds to and emits differing wavelengths of light, depending on the nature of its chemical structure and environment. In some embodiments, the fluorescent protein useful in the invention includes, but is not limited to, green fluorescent protein (e.g., wt-GFP, EGFP, Emerald, Superfolder GFP, Azami Green, mWasabi, TagGFP, TurboGFP, AcGFP, ZsGreen, T-Sapphire, etc.), blue fluorescent protein, (e.g., EBFP, EBFP2, Azurite, mTagBFP, etc.), cyan fluorescent protein (e.g., ECFP, mECFP, Cerulean, mTurquoise, CyPet, AmCyan1, Midori-Ishi Cyan, TagCFP, mTFP1 (Teal), etc.), yellow fluorescent protein (e.g., EYFP, Topaz, Venus, mCitrine, YPet, TagYFP, PhiYFP, ZsYellow1, mBanana, etc.), orange fluorescent protein (e.g., Kusabira Orange, Kusabira Orange2, mOrange, mOrange2, dTomato, dTomato-Tandem, TagRFP, TagRFP-T, DsRed, DsRed2, DsRed-Express (TI), DsRed-Monomer, mTangerine, etc.), or red fluorescent protein (e.g., mRuby, mApple, mStrawberry, AsRed2, mRFP1, JRed, mCherry, HcRed1, mRaspberry, dKeima-Tandem, HcRed-Tandem, mPlum, AQ143, etc.). In some embodiments, the transgene encodes GFP. In some embodiments, reporter molecules can be fused in-frame to other protein coding sequences to identify where a protein is located in a cell, tissue, organ, or organism. Reporters for use in accordance with the present disclosure include any reporter described herein or known to one of ordinary skill in the art.

Methods of Use

The nucleic acids and compositions of the disclosure may be used to deliver any transgene with a biological effect to treat and/or ameliorate the symptoms associated with any disorder related to gene expression. Methods of the present disclosure may be used to, for example, replace a protein that is deficient or abnormal, augment an existing biological pathway, provide a novel function or activity, by integrating and stably expressing transgenes. Methods of the present disclosure may also be used to transiently express transgenes and elicit an immune response.

In one aspect, the disclosure provides a method for expressing a transgene in a subject in need thereof, the method comprising administering to the subject an effective amount of a composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences, thereby expressing the one or more transgenes in the subject. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some aspects, the disclosed transgene can be expressed in a subject in need thereof. The composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences can be used to express the one or more transgenes in the subject.

In one aspect, the disclosure provides a method for expressing a transgene in a cell, the method comprising delivering to the cell a composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences, thereby expressing the one or more transgenes in the cell. In some embodiments, the one or more nucleic acid molecules encoding the retroviral Pol polyprotein components further encode one or more accessory retroviral proteins. In some embodiments, the composition comprises one or more additional nucleic acid molecules encoding one or more accessory retroviral proteins. Suitable cell types include, but are not limited to, HSCs, liver cells, ocular cells (e.g., retinal cells), muscle cells, epithelial cells, T cells (e.g., cytotoxic T cells), etc. In some aspects, the disclosed transgene can be expressed in a cell. The composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences can be used to express one or more transgenes in the cell.

In one aspect, the disclosure provides a method for expressing a transgene in a tissue, the method comprising delivering to the tissue a composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences, thereby expressing the one or more transgenes in the tissue. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. Suitable tissues include, but are not limited to, bone marrow, muscle, ocular tissue, cardiac tissue, liver tissue, epithelial tissue, connective tissue, nervous tissue, gastrointestinal tissue, etc. In some aspects, the disclosed transgene can be expressed in a tissue. The composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences can be used to express one or more transgenes in the tissue.

In one aspect, the disclosure provides a method for expressing a transgene in an organ, the method comprising delivering to the organ a composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences, thereby expressing the one or more transgenes in the organ. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. Suitable organs include, but are not limited to, eyes, heart, lungs, liver, stomach, spleen, pancreas, small intestine, large intestine, kidneys, bone marrow, brain, etc. In some aspects, the disclosed transgene can be expressed in an organ. The composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences can be used to express one or more transgenes in the organ.

In one aspect, the disclosure provides a method of treating a condition using a composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences, the method comprising administering the composition to a subject in need of treatment, thereby expressing the transgene in the subject. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some aspects, the disclosed transgene can be used to treat a condition. The composition comprising one or more nucleic acid molecules encoding retroviral Pol polyprotein components for reverse transcription and integration of a transgene-encoding nucleic acid and a transgene-encoding nucleic acid comprising one or more transgene sequences flanked by LTR sequences can be used to treat the condition.

In some embodiments, the one or more transgenes are integrated into the genome of a target cell (e.g., in a subject). In some embodiments, the one or more transgenes are stably expressed for at least a week, at least two weeks, at least a month, at least 6 months, at least a year, at least 2 years, at least 3 years, at least 4 years, or at least 5 years. In some embodiments, the one or more transgenes are stably expressed for 1-2 weeks, 2-4 weeks, 1-3 months, 3-6 months, 6-9 months, 9-12 months, 1-2 years, 2-3 years, 3-4 years, or 4-5 years, or longer. In some embodiments, the one or more transgenes are stably expressed for the lifetime of a subject. In some embodiments, the compositions of the disclosure are used to integrate one or more transgenes into the genome of a target cell (e.g., in a subject).

Any disease, disorder, or condition related to gene expression (e.g., where integration and stable expression of a transgene may be desired) may be treated. In some embodiments, the disease, disorder, or condition to be treated is a genetic condition. The genetic disease, disorder, or condition may be hereditary or non-hereditary. In some embodiments, the disease, disorder, or condition is a neurodegenerative, proliferative, inflammatory, or autoimmune disease, disorder, or condition. In some embodiments, the condition to be treated includes, but is not limited to, cystic fibrosis (and other diseases of the lung), hemophilia A, hemophilia B, beta-thalassemia, sickle cell disease, anemia and other blood coagulation disorders, Alzheimer's disease, Parkinson's disease, Huntington's disease, amyotrophic lateral sclerosis, epilepsy and other neurological disorders, cancer, diabetes mellitus, muscular dystrophies (e.g., Duchenne, Becker), Leber congenital amaurosis, lysosomal storage disease, Usher's syndrome 1C, gyrate atrophy, connexin 26 deafness, achromatopsia, X-linked retinoschisis, polycystic kidney disease, Gaucher's disease, Hurler's disease, adenosine deaminase deficiency, glycogen storage diseases and other metabolic defects, Pompe's disease, congestive heart failure, retinitis pigmentosa, diseases of solid organs (e.g., brain, liver, kidney, heart), and the like. In some embodiments, the condition to be treated is a cancer. In some embodiments, the cancer is a blood cancer (e.g., lymphoma, leukemia, multiple myeloma, etc.), breast cancer, prostate cancer, cancer of the digestive system (e.g., esophageal cancer, stomach cancer, colorectal cancer), liver cancer, cervical cancer, ovarian or uterine cancer, pancreatic cancer, lung cancer, brain cancer (e.g., glioblastoma), skin cancer (e.g., melanoma), or sarcomas of muscle or nerve, etc.

In some embodiments, the disclosure provides a method of treating beta-thalassemia or sickle cell disease in a subject in need thereof comprising administering a composition comprising one or more nucleic acid molecules encoding retroviral Pol polyprotein components for reverse transcription and integration of a transgene-encoding nucleic acid, and a nucleic acid molecule comprising a transgene encoding beta-globin, or a derivative thereof, flanked by LTR sequences. In some embodiments, the disclosure provides a method of treating sickle cell disease in a subject in need thereof comprising administering a composition comprising one or more nucleic acid molecules encoding retroviral Pol polyprotein components for reverse transcription and integration of a transgene-encoding nucleic acid, and a nucleic acid molecule comprising a transgene encoding beta-globin, or a derivative thereof, flanked by LTR sequences. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some aspects, the compositions of the disclosure can be used in the treatment of beta-thalassemia or sickle cell disease.

In some embodiments, the disclosure provides a method of treating cystic fibrosis in a subject in need thereof, comprising administering a composition comprising one or more nucleic acid molecules encoding retroviral Pol polyprotein components for reverse transcription and integration of a transgene-encoding nucleic acid, and a nucleic acid molecule comprising a transgene encoding CFTR, or a derivative thereof, flanked by LTR sequences. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some aspects, the compositions of the disclosure can be used in the treatment of cystic fibrosis.

In some embodiments, the disclosure provides a method of treating hemophilia B in a subject in need thereof comprising administering a composition one or more nucleic acid molecules encoding retroviral Pol polyprotein components for reverse transcription and integration of a transgene-encoding nucleic acid, and a nucleic acid molecule comprising a transgene encoding Factor VIII, or a derivative thereof, flanked by LTR sequences. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some aspects, the compositions of the disclosure can be used in the treatment of hemophilia B.

In some embodiments, the disclosure provides a method of treating DMD in a subject in need thereof comprising administering a composition comprising one or more nucleic acid molecules encoding retroviral Pol polyprotein components for reverse transcription and integration of a transgene-encoding nucleic acid, and a nucleic acid molecule comprising a transgene encoding dystrophin, or a derivative thereof, flanked by LTR sequences. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some aspects, the compositions of the disclosure can be used in the treatment of DMD.

In some embodiments, the disclosure provides a method of treating retinitis pigmentosa in a subject in need thereof comprising administering a composition comprising one or more nucleic acid molecules encoding retroviral Pol polyprotein components for reverse transcription/integration of a transgene-encoding nucleic acid, and a nucleic acid comprising a transgene encoding RPGR, or a derivative thereof, flanked by LTR sequences. In some embodiments, the nucleic acid molecules encoding the retroviral Pol poly protein components further encode one or more accessory retroviral proteins. In some embodiments, the composition comprises one or more additional nucleic acid molecules encoding one or more accessory retroviral proteins. In some aspects, the compositions of the disclosure can be used in the treatment of retinitis pigmentosa.

In some embodiments, the disclosure provides a method of treating cancer in a subject in need thereof comprising administering a composition comprising one or more nucleic acid molecules encoding retroviral Pol polyprotein components for reverse transcription and integration of a transgene-encoding nucleic acid, and a nucleic acid molecule comprising a transgene encoding a chimeric antigen receptor (CAR) flanked by LTR sequences. In some embodiments, the condition to be treated is a cancer. In some embodiments, the cancer is a blood cancer (e.g., lymphoma, leukemia, multiple myeloma, etc.), breast cancer, prostate cancer, cancer of the digestive system (e.g., esophageal cancer, stomach cancer, colorectal cancer), liver cancer, cervical cancer, ovarian or uterine cancer, pancreatic cancer, lung cancer, brain cancer (e.g., glioblastoma), skin cancer (e.g., melanoma), sarcomas of muscle or nerve, etc. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some aspects, the compositions of the disclosure can be used in the treatment of cancer.

In some embodiments, the one or more transgenes are transiently expressed once integrated into the genome of a target cell (e.g., in a subject). The transient expression is sufficient to elicit an immune response. Any disease, disorder or condition which will benefit from an immune response can be treated. Thus, in some embodiments, the disclosure provides a method of eliciting an immune response in a subject in need thereof by transiently expressing one or more transgenes, the method comprising administering to the subject an effective amount of a composition comprising one or more nucleic acid molecules encoding retroviral Pol polyprotein components and a nucleic acid molecule comprising a transgene flanked by long terminal repeat sequences, thereby expressing the transgene in the subject. In some embodiments, the disease, disorder or condition is cancer and the transgene may encode a tumor antigen. In some embodiments, the disease, disorder or condition is an infectious disease (e.g., a disease caused by an infectious agent such as a pathogenic organism) and the transgene may encode an antigen associated with the infectious disease. The subject may be at risk for contracting an infectious disease and the composition may be administered prophylactically. In some aspects, the compositions of the disclosure can be used to elicit an immune response.

Non-Viral Delivery Systems

The nucleic acid molecules of the disclosure are delivered to a cell, tissue, or subject via a non-viral delivery system. Any suitable non-viral delivery system known in the art may be employed to deliver the nucleic acid molecules of the disclosure to the target tissues and/or cells ex vivo or in vivo.

In some embodiments, the nucleic acid molecules (e.g., RNA, ssDNA, linear dsDNA) are packaged in lipid nanoparticles (LNPs). Suitable LNPs for packaging DNA molecules and RNA molecules (e.g., mRNA molecules) are known in the art. In some embodiments, the LNPs comprise one or more ionizable or cationic lipids (e.g., N-[1-(2,3-dioleoyloxy)propyl]-N,N,N-trimethylammonium chloride (DOTMA); 1,2-dioleoyl-3-trimethylammonium-propane (DOTAP); 1,2-dioleoyl-3-dimethylammonium propane (DODAP); DODMA; Dlin-MC3-DMA (MC3); LP-01; diketopiperazine-based ionizable lipid, cKK-E12); one or more neutral phospholipids (e.g., cholesterol), one or more zwitterionic lipid molecules (e.g., 1,2-dioleoyl-sn-glycero-3-phosphoethanolamine (DOPE)), and/or one or PEG-modified lipids. In some embodiments, the LNPs comprise a polylactic acid (PLA) or poly(lactic-co-glycolic acid) (PGLA) polymers within a lipid monolayer. In some embodiments, ionizable lipids are pH-dependent ionizable materials.

In some embodiments, the non-viral delivery systems, including but not limited to, LNPs, are conjugated with polypeptides that specifically bind receptors on a target cell or tissue (e.g., viral envelope or capsid proteins, antibodies or antigen-binding fragments thereof, or other targeting moieties). In some embodiments, the LNPs are conjugated to a small molecule that facilitates targeting to a specific cell, tissue, or organ. Suitable cell types include, but are not limited to, HSCs, liver cells (e.g., hepatocytes), ocular cells (e.g., retinal cells), muscle cells, epithelial cells, T cells (e.g., cytotoxic T cells), etc. Suitable tissues include, but are not limited to, bone marrow, muscle, ocular tissue, cardiac tissue, liver tissue, epithelial tissue, connective tissue, nervous tissue, gastrointestinal tissue, etc. Suitable organs include, but are not limited to, eyes, heart, lungs, liver, stomach, spleen, pancreas, small intestine, large intestine, kidneys, etc. In some embodiments, the target cell or tissue include, but are not limited to, bone marrow, HSCs, epithelial cells, liver cells (e.g., hepatocytes), ocular cells (e.g., retinal cells), muscle cells, T cells (e.g., cytotoxic T cells).

In some embodiments, the nucleic acid molecules of the disclosure may be delivered naked, in an aqueous solution (such as a buffer, e.g., a sucrose citrate buffer), or in combination with lipids, polymers, peptides, or other compounds that facilitate entry into the cells. The nucleic acid molecules may be introduced into target cells or subjects using any suitable technique, e.g., by direct injection, microinjection, transfection, nucleofection, electroporation, lipofection, high pressure spraying, biolystics, and the like. In some embodiments, the nucleic acid molecules are complexed with a cationic amphiphile. In some embodiments, the nucleic acid molecules are complexed with a transfection agent (e.g., Lipofectamine™, Lipofectin™, jetPEI, RNAiMAX, and Invivofectamine, MegaFectin™, TransIT™). In some embodiments, the nucleic acid molecules are complexed with a cell-penetrating peptide (e.g., a polycationic or an amphipathic peptide).

In some embodiments, the nucleic acid molecules of the disclosure are packaged in liposomes, lipid nanoparticles, polypeptide nanoparticles, inorganic materials (e.g., silica nanoparticles, gold nanoparticles, and inorganic-based carriers such as CaP), synthetic polymers, dendrimers, cationic nanoemulsions, polymeric nanoparticles, polymer and lipid hybrid carriers, or combinations thereof. In some embodiments, the nucleic acid molecules of the disclosure are packaged in viral capsids.

In some embodiments, the nucleic acid molecules of the disclosure are packaged in polymeric nanoparticles including, but not limited to, nanoparticles based on polyethyleneimine (PEI), polyacrylates, poly(β-amino esters) (PBAEs), and poly(aspartamides) (PAsp).

In some embodiments, the nucleic acid molecules of the disclosure are packaged in liposomes. Liposomes are artificially prepared vesicles which may primarily be composed of a lipid bilayer. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the nucleic acid molecules. In some embodiments, the nucleic acid molecules of the disclosure are packaged in liposomes, such as those formed from 1,2-dioleyloxy-N,N-dimethylaminopropane (DODMA) liposomes, DiLa2 liposomes from Marina Biotech (Bothell, Wash.). 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120, the contents of which are herein incorporated by reference in its entirety). In some embodiments, the liposomes are PEGylated.

The nucleic acid molecules of the disclosure (e.g., packaged in liposomes, lipid nanoparticles, cationic nanoemulsions, polymeric nanoparticles, etc.) can be administered systemically or locally, intravenously, intradermally, intraarterially, intralesionally, intratumorally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, locally, by inhalation (e.g., aerosol inhalation), by injection, by infusion, by continuous infusion, by localized perfusion bathing target cells directly, via a catheter, via a lavage, in creams, or by any other method or any combination of the foregoing as would be known to one of ordinary skill in the art (see, for example, *Remington's Pharmaceutical Sciences* (1990), incorporated herein by reference).

In some embodiments, the nucleic acid molecules of the disclosure (e.g., packaged in liposomes, lipid nanoparticles, cationic nanoemulsions, polymeric nanoparticles) are administered in the form of a pharmaceutical composition comprising a pharmaceutically-acceptable carrier. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences* (1990), incorporated herein by reference). Except insofar as any conventional carrier is incompatible with the active ingredient, its use in the therapeutic or pharmaceutical compositions is contemplated. Compositions for lipid nanoparticles with biological active molecules and suitable carriers are disclosed in, for example, U.S. Pat. No. 7,404,969, which is incorporated herein by reference.

The nucleic acid molecules of the of the disclosure can be administered once, or alternatively they may be administered in a plurality of administrations. If administered multiple times, the compounds may be administered via different routes. For example, the first (or the first few) administrations may be made directly into the affected tissue while later administrations may be systemic.

Kits

In one aspect, the present disclosure provides kits for delivery of one or more transgenes. In some embodiments, the kit comprises a composition comprising an effective amount of one or more nucleic acid molecules encoding retroviral Pol polyprotein components, and a nucleic acid molecule encoding one or more transgenes flanked by LTR sequences according to the disclosure. In some embodiments, the kit comprises a composition comprising an effective amount of one or more nucleic acid molecules encoding retroviral Pol polyprotein components, and a nucleic acid molecule encoding one or more transgenes flanked by LTR sequences according to the disclosure, in unit dosage form. In some embodiments, the nucleic acid molecules encoding the retroviral Pol polyprotein components further encode one or more accessory retroviral proteins. In some embodiments, the composition comprises one or more additional nucleic acid molecules encoding one or more accessory retroviral proteins. In some embodiments, the kit comprises a composition comprising two nucleic acid molecules. In some embodiments, the kit comprises a composition comprising two or more nucleic acid molecules (e.g., 2, 3, 4, or 5). In some embodiments, the nucleic acid molecules are packaged or formulated for delivery in lipid nanoparticles. In some embodiments, the kit comprises a sterile container which comprises the composition. Such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. If desired, the composition is provided together with instructions for administering the cell to a subject in need thereof.

EXAMPLES

In order that the invention described herein may be more fully understood, the following examples are set forth. The Examples described in this Application are offered to illustrate the methods, compositions, and systems provided herein and are not to be construed in any way as limiting their scope.

Example 1: mRNA-Encoded Minimal Lentiviral Machinery for In Vivo Gene Therapy

A transgene-encoding template was designed as shown in FIG. 3. The transgene-encoding nucleic acid template comprises, from 5' to 3', a 5' LTR, a reverse transcriptase priming element, a promoter operably linked to a transgene, an enhancer, and a 3' LTR. Additional RNA production elements include a 5' T7 RNA polymerase promoter and a 3' digest site. The RNA molecule produced from the transgene-encoding nucleic acid template comprises unmodified nucleosides since retroviral reverse transcriptases cannot copy modified ribonucleases (Swanstrom et al., *J. Biol. Chem.* 256:1115-1121(1981)). Additionally, the RNA has a 5'-7mG cap structure and a poly(rA) tail to enhance RNA stability.

Two minimal nucleic acid templates encoding Pol poly proteins (for reverse transcription/integration) were designed as shown in FIG. 4. The canonical gene construction provides for the gag and pol to be expressed inline, which requires translation slippage for Pol polyprotein expression. The novel design increases pol expression by processing pol from a separate construct as a polyprotein unit (or even potentially separate units as explained below). These novel designs encode different UTRs for increased mRNA stability and translation. This novel design optionally encodes accessory protein units essential for reverse transcription and integration with pol, which can be in cis with 2A. The first nucleic acid template comprises from 5' to 3', a 5' UTR, a nucleic acid sequence encoding retroviral Pol polyprotein components in the form of a Pol polyprotein, and a 3' UTR. Additional RNA production elements include a 5' T7 RNA polymerase promoter and a 3' digest site. The second nucleic acid template comprises from 5' to 3', a 5' UTR, a nucleic acid sequence encoding one or more retroviral accessory proteins, a nucleic acid sequence encoding retroviral Pol polyprotein components in the form of a Pol polyprotein, and a 3' UTR. The accessory protein units include retroviral elements not encoded by the pol polyprotein gene, and examples include, but are not limited, gag poly protein (p55), MA (p17), CA (p24), NC (p9), p6, tat, nef, vpr, vif, and vpu. Additional RNA production elements include a 5' T7 RNA polymerase promoter and a 3' digest site. The mRNA molecules produced from these nucleic acid templates comprise both modified (e.g., pseudouridine) and unmodified nucleosides. The use of modified nucleosides reduces the immunogenicity of the final mRNA molecule. Additionally, the mRNA has a 5'-7mG cap structure and a poly(rA) tail to ensure efficient translation and stability. For example, the 3' UTR could encode poly A tail.

Figure 5A:
FIGS. 5A-5C illustrate an exemplary embodiment of a reverse transcription and integration machinery design, wherein the Pol polyprotein components are encoded as separate proteins on one or more nucleic acid molecule. RNA production elements include an RNA polymerase promoter (e.g., the T7 RNA polymerase promoter) and optionally, one or more restriction digestion sites for template linearization.
Figure 5B:
Figure 5C:

At least three different constructs for expressing the multiple-functional units of the Pol polyprotein were designed as shown in FIG. 5. In the first, as shown in FIG. 5A, the construct provides the protease (PR), reverse transcriptase/RNase H (RT), and integrase (IN) as a canonical unit, where each component is separated by autoprocessing by PR In the second, as shown in FIG. 5B, the Pol polyprotein component individual units RT and IN are encoded on a bicistronic construct. In the third, as shown in FIG. 5C, the Pol polyprotein component individual units are encoded on separate constructs. There are various scenarios in which these constructs could be used. First, all of the Pol polyprotein components can be encoded as a polyprotein on one mRNA with a 5' and 3' UTR (represented by FIG. 5A), wherein the PR protease is required when encoding the components as polyprotein (pol). Second, the Pol polyprotein components RT and IN units can be encoded on one or more constructs each with a 5' and 3' UTR with intervening IRES or 2A sequences (represented by FIG. 5B), wherein the PR protease is not required when encoding the elements as "non-polyprotein" individual units. Third, the Pol polyprotein components RT and IN units can be encoded on two or more constructs each with a 5' and 3' UTR (represented by FIG. 5C). Fourth, the Pol polyprotein components RT and IN units and accessory protein units can be encoded on one construct each with a 5' and 3' UTR with intervening IRES or 2A sequences. In this scenario, when the accessory elements are encoded as a polyprotein, for example the Gag polyprotein, the PR protease will be required. And as a fifth, non-limiting scenario, the Pol polyprotein components RT and IN units and accessory protein units can be encoded on two or more constructs each with a 5' and 3' UTR.

Example 2: In Vivo Delivery of Beta-Globin to Treat Sickle Cell Disease

A transgene-encoding nucleic acid templates as described in Example 1 comprising a beta-globin transgene is used to produce an RNA molecule comprising the beta-globin gene flanked by LTRs for integration into a host cell genome. A nucleic acid template comprising, from 5' to 3', a 5' UTR, a nucleic acid sequence encoding retroviral Pol polyprotein components in the form of a Pol polyprotein, and a 3' UTR, as described in Example 1 is used to produce an RNA molecule encoding retroviral Pol proteins.

An effective amount of a lipid nanoparticle composition comprising the two RNA molecules is administered to a patient suffering from sickle cell disease to treat sickle cell disease.

Example 3: Improving RNA Stability and Translation in Human Cells

The lentivirus-derived genes forming the basis of the RNA-mediated transgene integration systems described herein can pose challenges for synthetic gene expression in cells. Lentiviral replication steps undergo tightly-controlled spatiotemporal processes that are orchestrated by a full complement of viral genes and regulatory elements, structural proteins, replicative enzymes, and interaction with host factors critical for replication. This example describes several modifications to increase stability and efficiency of the RNA-based integration system.

Increased Stability of Functional Unit RNAs

The one or more nucleic acid molecules encoding one or more Pol polyprotein components and/or accessory proteins are also referred to as "functional unit nucleic acids." The generation of a minimal, integration-competent RNA system generally entails the removal of viral genes that do not directly influence reverse transcription and proviral integration. However, expression of wild-type individual viral RNAs (i.e., Reverse Transcriptase (RT) and integrase (IN)) in the absence of the full-length viral genome is challenging without accessory proteins, such as for example Rev. In addition, wild-type HIV-1 RNAs are inherently unstable due to the presence of intrinsic instability elements (INS), short, 5-nucleotide repeats present throughout transcripts (Wolff et al. *Nucleic Acids Res.* 31(11):2839-51 (2003)). During HIV-1 infection, Rev can counteract the effect of INS because it can bind to and stabilize the RNA transcripts. To increase RNA stability in the absence of Rev, five major INS sequences were identified, removed, and replaced throughout functional unit mRNAs: TAGAT, ATAGA, AAAAG, ATAAA, TTATA or other INS elements (e.g., such as those described for example in Wolff et al. *Nucleic Acids Res.* 31(11):2839-51 (2003)). INS removal can be partial or complete. The INS sequences can be replaced with alternate codons, preserving the protein sequence while increasing the stability of the RNA.

Furthermore, human codon optimization (hCO) results in increased gene expression in human cells. Previous studies using full-length gag-pol genes demonstrated Rev-independence following human codon optimization (Kotsopoulou et al. *J Virol.* 74(10): 4839-52 (2000)). hCO functional unit mRNAs were generated for increased translation and stability in target cells. In another iteration, remaining INS elements were removed and replaced from hCO sequences.

These improvements have been applied to all Pol polyprotein components and accessory proteins, including RT, IN, Matrix (MA), Capsid (CA), Nucleocapsid (NC) and Vpr RNAs.

Increased Stability of Functional Unit Proteins

Due to their cytoplasmic translation from input mRNAs, the functional units (e.g., Pol polyprotein components and accessory proteins) in this system can lack the spatiotemporal coordination observed in incoming virus particles. Unlike incoming virus particles, in which active IN and RT are packaged in close proximity to viral genomes, this RNA-based system first necessitates translation of incoming functional unit mRNAs and subsequent interaction of newly-translated functional units with the transgene-encoding RNA. Thus, protein lifetime of the functional units is important.

Wild-type IN protein is short-lived in cells, as the N-terminal residues of the wild-type IN are substrates for proteolytic degradation (Mulder et al. *J Biol Chem.* 275(38): 29749-53 (2000)). Previous studies using expression plasmids demonstrated that this degradation is counteracted by the addition of an N-terminal Methionine-Glycine dipeptide (Cherepanov et al. *FASEB J.* 14(10):1389-99 (2000)). Several N-terminal Met-Gly IN constructs were generated. These mRNAs are derived from WT HIV genes, are hCO, and/or have undergone removal and replacement of INS constructs.

Cytoplasmic Redirection of Pol-Derived Functional Units in Target Cells

In some embodiments, RNAs encoding singular gag or pol genes were generated, which comprise critical structural proteins necessary for nuclear pore crossing during the pre-integration replication step, or RT and IN, respectively. This strategy is advantageous in that the functional unit RNA sequences are translated as natural Gag or Pol polyproteins, while separation of the gag and pol genes enables stoichiometric optimization that favors intracellular activity. Expression of gag and pol genes in wild-type ratios results in assembly, budding, and release of new viruses from the producer cell into the extracellular space (Sundquist et al. *Cold Spring Harb Perspect Med.* 2(7):a006924 (2012)). While there is some evidence for functional RT and IN activity in the producer cell (Al Mosabbir et al. *Biotechnol. Lett.* 38(10):1715-21 (2016)), expression of new viral gene products in the producer cell is primarily understood to favor new virion formation. Several studies of expression plasmids encoding gag and pol have indicated redirection of viral gene expression away from particle formation toward intracellular activity of pol products (Al Mosabbir et al. *Biotechnol. Lett.* 38(10):1715-21 (2016), Karacostas V et al. *Virology* 193(2):661-71 (1993)). To this end, several mechanisms involving DNA plasmid transfection have been established: (1) deletion of the gag sequence encoding matrix protein, which anchors the Gag polyprotein to the plasma membrane during viral budding (Al Mosabbir et al. *Biotechnol. Lett.* 38(10):1715-21 (2016)), and (2) a single-nucleotide insertion disrupting the gag-pol frameshift mechanism (Karacostas V et al. *Virology* 193(2):661-71 (1993)). While these modifications have been described in the context of full-length viral genomes, they have not been explored for (1) extra-genomic singular gene expression and (2) synthetic, functional RNA. To facilitate intracellular activity of functional units expressed as gag- and pol-derived polyproteins, several novel full-length gag and pol RNAs were engineered: (1) Matrix-deleted gag-pol RNAs for prevention of particle budding, (2) Matrix-deleted singular gag RNAs (3) hCO matrix-deleted gag-pol RNAs for prevention of particle budding (4) RNAs containing mutations that result in gag and pol in a singular reading frame, (5) hCO gag-pol frameshifted RNAs for intracellular pol activity, (6) transfection of singular gag or pol RNAs in optimized ratios that result in intracellular Pol product accumulation.

Primed RNA Genomes for Facilitation of the Reverse Transcription Reaction

HIV-1 RT depends on cytoplasmic tRNAs for priming of the viral genome prior to the reverse transcription reaction. Increased efficiency of the reverse transcription reaction in vitro through priming the viral genome with short RNA or DNA oligos has been observed (Iwatani et al. *J Biol Chem.* 278(16):14185-95 (2003)). As a strategy for increasing the efficiency of the reverse transcription reaction in our integration-competent system, transgene-encoding RNAs are primed with short RNA or DNA oligos prior to their co-delivery into target cells with functional unit mRNA(s).

Uncapped Transgene-Encoding RNA

HIV-1 RNA genomes are capped following transcription in producer cells. Following viral entry, viral genomes are decapped by cellular host factors, such as RNA debranching enzyme 1 (DBR1), prior to reverse transcription (Galvis et al. *J Virol.* 2017 November 14; 91(23): e01377-17 (2017)). To increase efficiency of the reverse transcription step, uncapped transgene-encoding RNAs were produced and cotransfected with functional unit mRNA(s).

Example 4: Materials and Methods

The materials and methods used in the studies described in Examples 5 and 6 are described.

IVT Template Design

DNA template sequences for IVT of functional unit RNA, including UTRs and 5' T7 promoters, were cloned into the pTWIST Amp cloning vector (Twist Bioscience). IVT template sequences for the transgene-encoding RNA, including LTRs and 5' T7 promoters, were cloned into the pMK backbone from GeneArt (ThermoFisher).

RNA Manufacturing and Purification

Plasmids containing IVT templates were linearized by digestion with BsmBI, or Bsu36I and SfiI (New England Biolabs). Digested DNA was isopropanol precipitated. Digested DNA template (30 ng/μL) was incubated for 4 h at 37° C. in the presence of NTPs (transgene-encoding RNA: 7.5 mM CTP, 1.5 mM GTP, 7.5 mM UTP; functional unit RNA: 4 mM ATP, 4 mM CTP, 4 mM GTP, 4 mM UTP), CleanCap (transgene-encoding RNA: CleanCap GG, 6 mM: functional unit RNA: CleanCap AG, 5 mM), 0.1M $MgSO_4$, 0.1M Spermidine, T7 RNA Polymerase (transgene-encoding RNA: 0.2 mg/mL; Functional Unit RNA: 0.1 mg/mL), and 40 U/mL TIPP (New England Biolabs). Reactions were treated with DNase (Thermo Fisher) and incubated for 15 minutes at 37° C. RNA was LiCl precipitated and resuspended in THE RNA storage solution (Thermo Fisher). In vitro transcribed RNA was enzymatically polyadenylated using *E. coli* Poly(A) polymerase (New England Biolabs). RNA (0.25 μg/μL) was incubated at 37° C. for 20 min in the presence of *E. coli* poly(A) polymerase (0.1 U/μL), 1× PolyA polymerase reaction buffer, and 10 mM ATP. RNA was LiCl precipitated and resuspended in THE RNA storage solution (Functional Unit RNA) or purified by HPLC (transgene-encoding RNA). Polyadenylation was confirmed using a BioAnalyzer (Agilent Technologies).

RNA Transfection

293FT cells (Thermo Fisher) were transfected with RNA using Lipofectamine 2000 (Thermo Fisher). For transgene expression experiments, cells seeded in 48-well plates were transfected with 500 ng of total RNA in the indicated ratios, complexed with 0.5 µL of Lipofectamine 2000 per well. For Western blotting, 293FT cells seeded in 12-well plates were transfected with 1 µg of integrase RNA and 2 µL Lipofectamine 2000 per well. For confocal microscopy, 293FT cells were seeded on Poly-D-Lysine-coated #1 coverslips (Electron Microscopy Sciences) in 24-well plates. Cells were transfected with 1 µg of the integrase RNA per well of a 24-well plate.

Western Blotting 48 h post-transfection, transfected cells were resuspended in RIPA buffer (Pierce, Thermo Fisher) containing Halt protease inhibitor (Pierce, Thermo Fisher). Following two freeze-thaw cycles at –80° C., cell suspensions were lysed in the presence of Benzoase nuclease at 4° C. (Sigma Aldrich). Lysates were incubated at 37° C. for 5 minutes, treated with EDTA, and clarified via centrifugation at 21,000×g for 20 minutes at 4° C. Lysates were electrophoresed on NuPage 4-12% Bis-Tris gels (Thermo Fisher) and transferred to 0.2 µg PVDF membranes (Trans-Blot Turbo Mini, Bio-Rad). Membranes were probed with primary antibodies to integrase (Abcam, [In-2], ab66645) and β-Actin (Abcam, ab8227). Integrase and β-Actin were detected with fluorescent secondary goat anti-mouse and goat anti-rabbit antibodies (Abcam), respectively. Blots were imaged on a Li-Cor imager.

Immunocytochemistry and Confocal Microscopy 24 h following transfection, transfected 293FT cells were washed with PBS and fixed for 7 min at room temperature in 4% paraformaldehyde (Electron Microscopy Sciences). After fixation, cells were washed with PBS. Fixed cells were stained overnight with 300 nM DAPI (Biotium), ViaFluor-647 (Biotium), and 1:100 anti-integrase antibody (Abcam, [In-2], ab66645) conjugated with CF-568 dye (Mix-and-Stain, Biotium) in blocking buffer (5% FBS, 1% BSA, and 1×TBS Tween (Thermo Fisher) in PBS) overnight at room temperature. Stained coverslips were washed with PBS and mounted onto Superfrost Plus microscope slides (Fisher) using ProLong Glass (ThermoFisher). Samples were visualized using a Nikon/Yokogawa CSU-W1 spinning disk confocal microscope.

Nanoluciferase Assays

Cells were lysed for 10 minutes at 37° C. in Nano-Glo Buffer (Promega) without furimazine. Nanoluciferase assays were conducted in 96-well opaque plates (Costar) via the addition of 25 µL of Nano-Glo buffer with 1:50 furimazine (Promega) to 20 µL of cell lysate per well. Luminescence was read on a BioTek HTX plate reader immediately after furimazine addition.

Figure 7A:
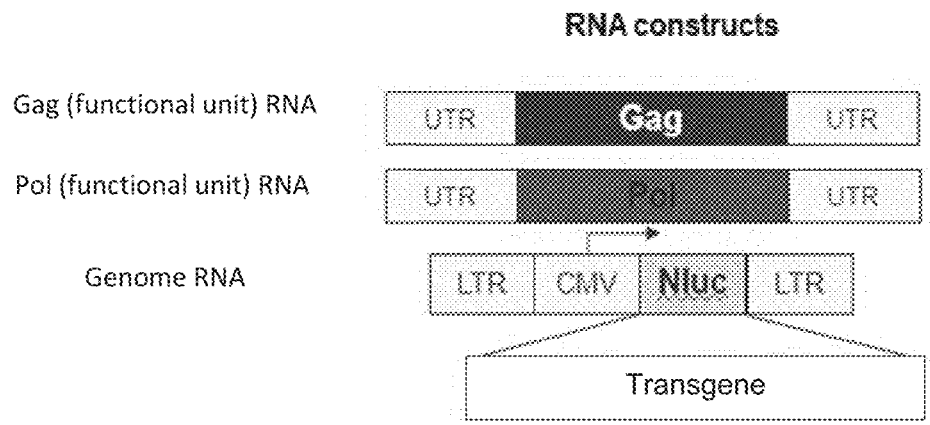
FIGS. 7A and 7B show that RNA-derived functional units drive reporter gene expression from transgene-encoding RNAs.
Figure 7B:
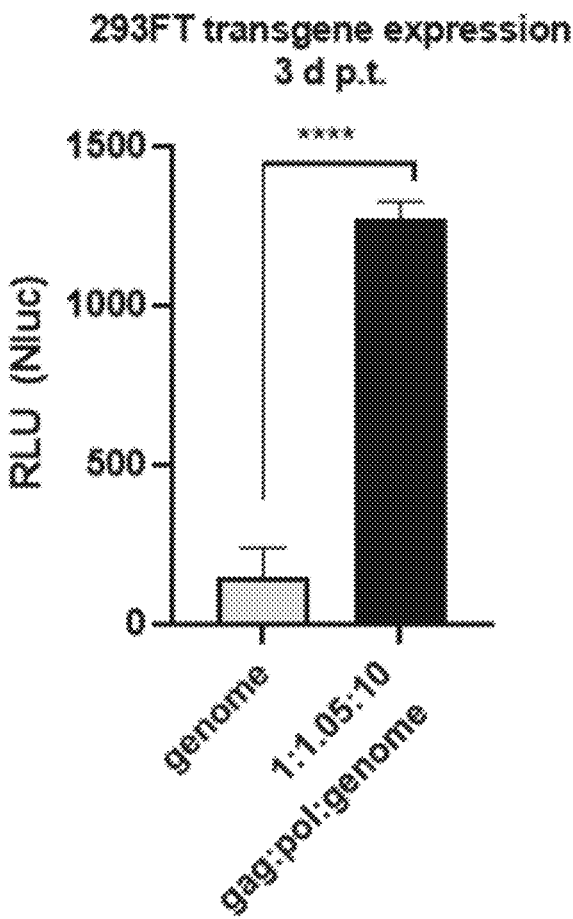

Example 5: RNA-Derived Functional Units Drive Reporter Gene Expression from Transgene-Encoding RNAs 293 FT cells were transfected with an RNA encoding the Gag polyprotein, an RNA encoding the Pol polyprotein, and a transgene-encoding RNA encoding nanoluciferase (Nluc), or with the transgene-encoding RNA alone. The RNA constructs are shown in FIG. 7A. Cells were harvested for Nluc assay at 3 days post-transfection. Nluc activity was assessed via a luminometer. Nluc activity is displayed as light units relative to background (RLU) (FIG. 7B). The ratio of RNA species in 500 ng RNA transfection per well of a 48-well plate is indicated. Statistical significance was determined and confirmed by Student's t-test; n=3. These results demonstrate that lentiviral RNA-derived functional units are able to drive reporter gene expression from a transgene-encoding RNA flanked by LTRs. The results further guide stoichiometries for individual mRNA functional unit plus transgene-encoding RNA transfections.

Example 6: Stabilized Functional Unit Expression

Figure 8A:
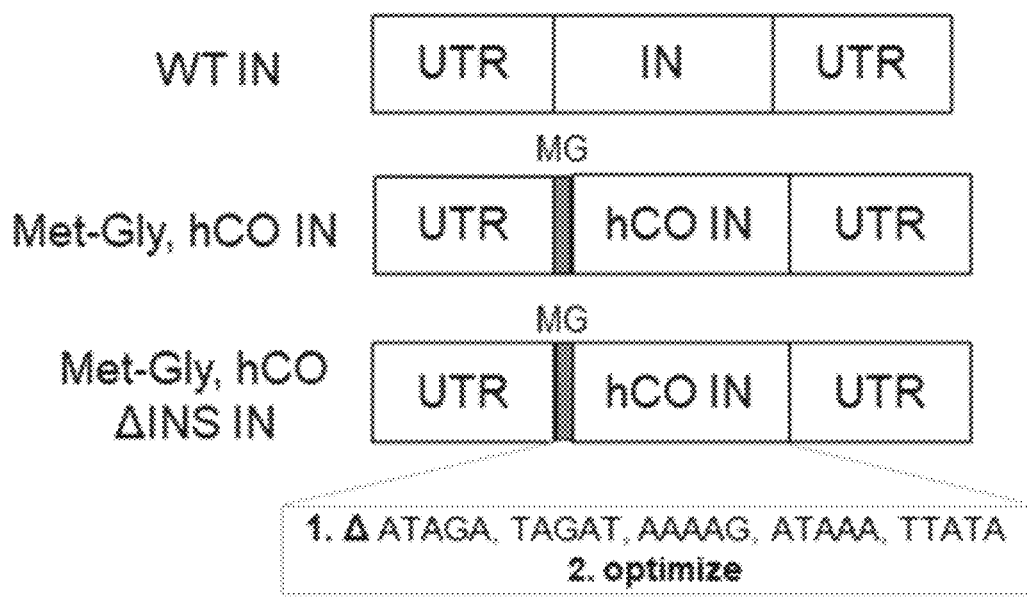
FIGS. 8A-8D show that optimized functional unit RNAs demonstrate enhanced expression and localize to target organelles.
Figure 8B:
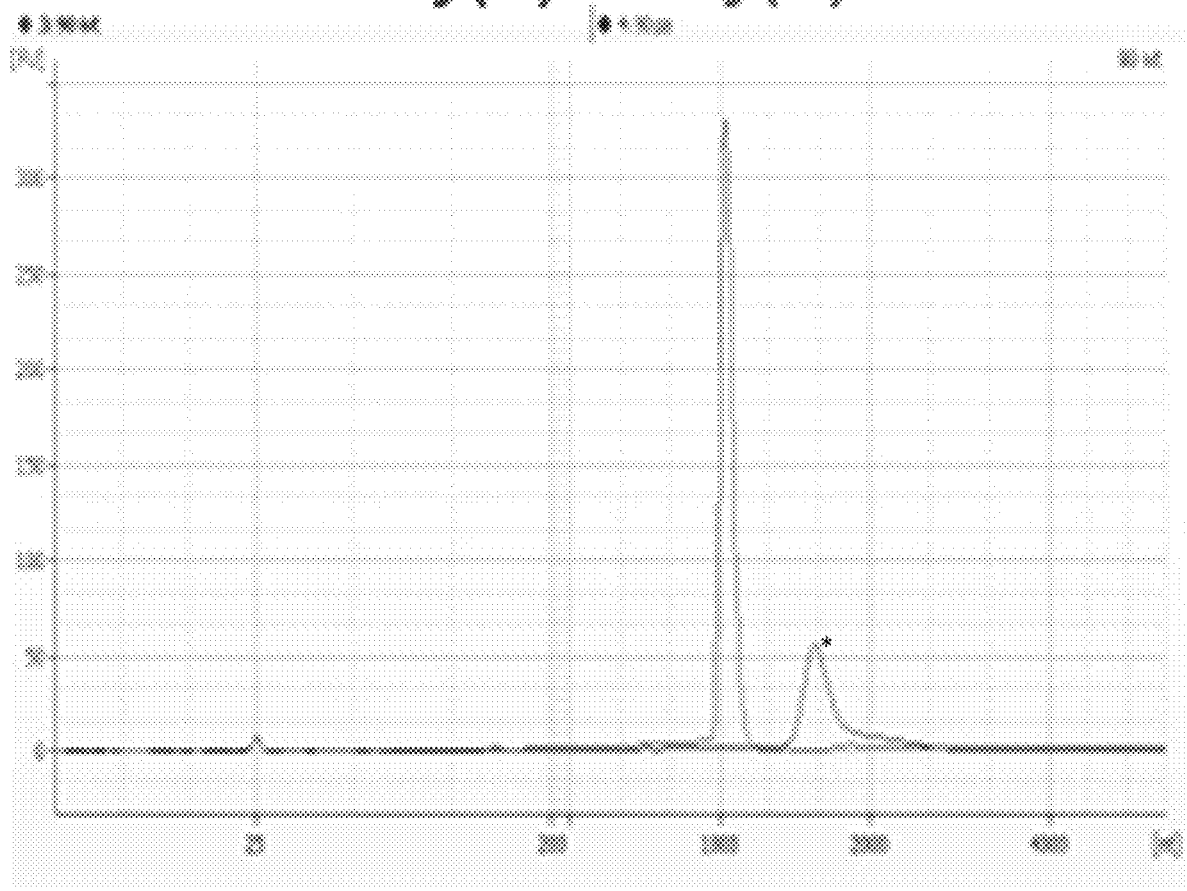

Optimized integrase (IN)-encoding functional unit mRNAs with one or more of the modifications described in Example 3, to increase RNA and/or protein stability, are more stably expressed than wild-type integrase and localize to the nucleus in human cells. RNA construct design elements of RNAs encoding wild-type IN, stabilized Met-Gly, hCO IN, and stabilized Met-Gly hCO ΔINS IN are shown in FIG. 8A. In ΔINS IN, instability sequences (INS) were identified and codon-optimized to increase RNA stability.

Figure 8C:
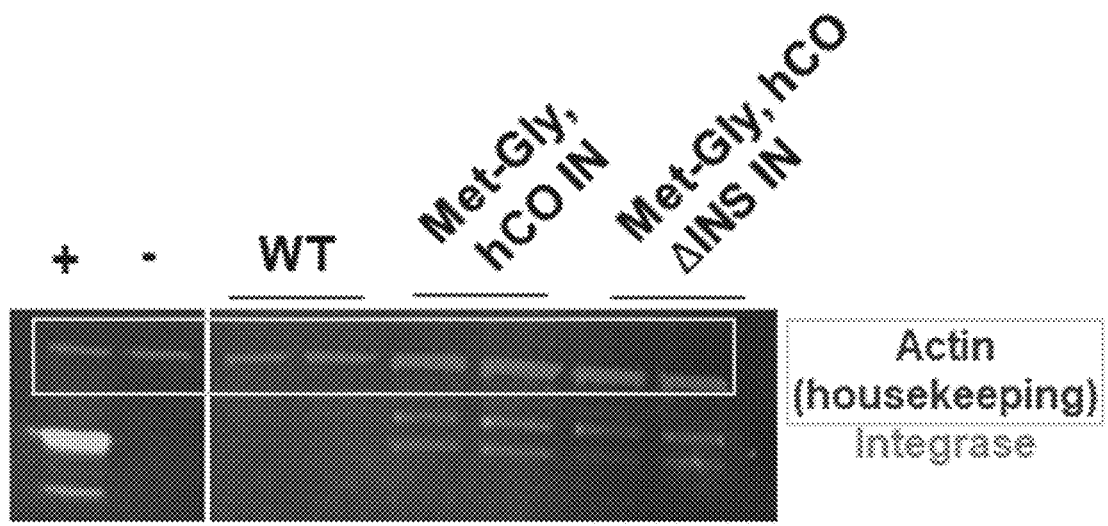
Figure 8D:
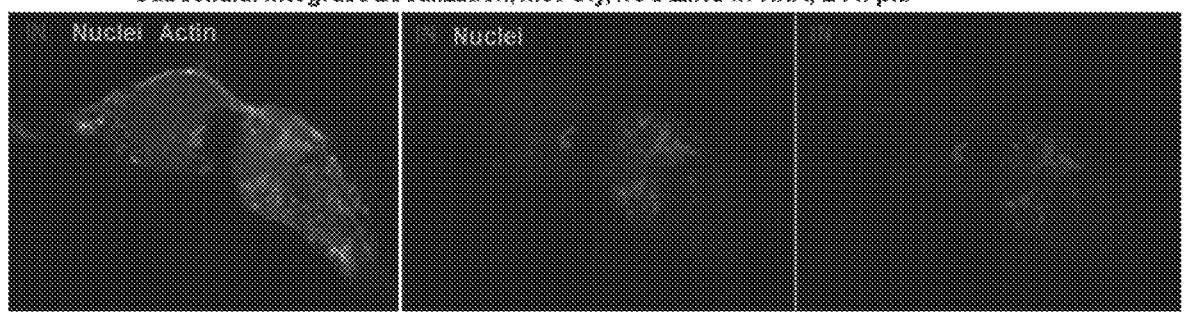

293FT cells were transfected with each indicated RNA and harvested for western blot lysis at 48 h post-transfection (p.t.). Integrase was expressed at higher levels from the optimized constructs compared to the construct encoding the wild-type IN. Wild-type IN protein bands were undetectable at 48 h p.t., in contrast to those from optimized constructs (FIG. 8C). Subcellular localization of optimized IN (Met-Gly hCO ΔINS IN) following RNA transfection into 293FT cells was also determined (FIG. 8D). Cells were transfected with optimized IN RNA fixed 24 h post-transfection, and processed for immunofluorescence. Fixed cells were stained with conjugated anti-N antibody. DAPI (nuclei), and phalloidin-647 (actin). Integrase was strongly expressed and localized to the nucleus. These results demonstrate that optimized integrase-encoding functional unit mRNAs demonstrated enhanced expression and localization to target organelles.

A summary of exemplary nucleotide sequences described in the examples is provided below in Table 1.

TABLE 1

Exemplary nucleotide sequences

| Description | Relevant FIG. | SEQ ID NO. |
|---|---|---|
| Transgene-encoding nucleic acid molecule with GFP transgene | 3 | 1 |
| Transgene-encoding nucleic acid molecule with mEYFP transgene | 3 | 2 |
| Transgene-encoding nucleic acid molecule with smURFP transgene | 3 | 3 |
| Transgene-encoding nucleic acid molecule with CyRFP transgene | 3 | 4 |
| Transgene-encoding nucleic acid molecule with firefly luciferase transgene | 3 | 5 |
| Canonical gag-pol | 4 | 6 |

TABLE 1-continued

Exemplary nucleotide sequences

| Description | Relevant FIG. | SEQ ID NO. |
|---|---|---|
| HIV-1 gag | 7 | 7 |
| Human codon optimized Met-Gly, IMS-deleted IN-I-PpoI N119A | 10 | 8 |
| Human codon optimized Pol-I-PpoI N119A | 10 | 9 |
| Transgene-encoding nucleic acid molecule with nanoluciferase transgene | 3, 7 | 10 |
| Human codon optimized pol RNA construct derived from pSYNGP plasmid with methionine-glycine dipeptide | 4, 5 | 11 |
| HIV-1 pol | 4, 5, 7 | 12 |
| Human codon optimized IN with Met-Gly dipeptide | 5, 7 | 13 |
| Human codon optimized IN with instability sequences replaced, methionine glycine dipeptide | 5, 7 | 14 |
| HIV-1 IN | 5, 8 | 15 |
| Human codon optimized RTp51 | 5, 8 | 16 |
| Human codon optimized RTp66 | 5, 8 | 17 |

EMBODIMENTS

The following embodiments are within the scope of the present disclosure. Furthermore, the disclosure encompasses all variations, combinations, and permutations of these embodiments in which one or more limitations, elements, clauses, and descriptive terms from one or more of the listed embodiments is introduced into another listed embodiment in this section. For example, any listed embodiment that is dependent on another embodiment can be modified to include one or more limitations found in any other listed embodiment in this section that is dependent on the same base embodiment. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the invention or aspects of the invention consist, or consist essentially of, such elements and/or features. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

1. A composition comprising:
   (i) one or more nucleic acid molecules encoding one or more Pol polyprotein components flanked by 5' and 3' untranslated regions (UTRs); and
   (ii) a nucleic acid molecule comprising one or more reverse transcriptase priming elements and one or more promoter sequences operably linked to one or more transgenes, between a 5' long terminal repeat (LTR) and a 3' LTR,
   wherein the composition does not contain nucleic acid sequences that express proteins encoded by retroviral rev and env genes.

2. The composition of embodiment 1, wherein the expression of the Pol polyprotein components do not require translational slippage from an inline gag gene.

3. The compositions of embodiments 1-2, wherein the one or more nucleic acid molecules of (i) do not encode the Gag polyprotein.

4. The compositions of embodiments 1-3, wherein the one or more nucleic acid molecules of (i) is a nucleic acid molecule comprising a 5' UTR, a nucleic acid sequence encoding a Pol polyprotein, and a 3' UTR.

5. The compositions of embodiments 1-3, wherein the one or more nucleic acid molecules of (i) is a nucleic acid molecule comprising a 5' UTR, a nucleic acid sequence encoding at least the Pol polyprotein components reverse transcriptase and integrase, and a 3' UTR.

6. The compositions of embodiment 5, wherein the Pol polyprotein components reverse transcriptase and integrase are expressed on a bicistronic construct.

7. The compositions of embodiments 5-6, wherein the Pol polyprotein components reverse transcriptase and integrase are expressed with an intervening internal ribosome entry sites (IRESes) or 2A peptide-encoding sequence.

8. The compositions of embodiments 1-3, wherein the one or more nucleic acid molecules of (i) is two nucleic acid molecules, wherein one of the two nucleic acid molecules comprises a 5' UTR, a nucleic acid sequence encoding at least the Pol polyprotein component reverse transcriptase, and a 3' UTR, and wherein the second of the two nucleic acid molecules comprises a 5' UTR, a nucleic acid sequence encoding at least the Pol polyprotein component integrase, and a 3'UTR.

9. The compositions of embodiments 1-8, wherein the one or more nucleic acid molecules of (i) also comprises a nucleic acid encoding one or more Gag polyprotein accessory proteins.

10. The composition of embodiment 9, wherein the one or more Gag polyprotein accessory proteins are encoded on the same nucleic acid molecule as the Pol polyprotein components.

11. The composition of embodiment 10, wherein the one or more Gag polyprotein accessory proteins are expressed with an intervening internal ribosome entry sites (IRESes) or 2A peptide-encoding sequence.

12. The composition of embodiment 9, wherein the one or more Gag polyprotein accessory proteins are encoded by one or more different nucleic acid molecules as the Pol polyprotein components, wherein each nucleic acid molecule comprises a 5' UTR and a 3' UTR.

13. The composition of any one of embodiments 9-12, wherein the Gag polyprotein accessory proteins are selected from nucleocapsid (NC), capsid protein (CA), matrix protein (MA), p6, viral infectivity factor (Vif), transactivator-of transcription (Tat), negative regulatory factor (Nef), viral protein R (Vpr), and viral protein u (Vpu).

14. The composition of embodiment 13, wherein the Gag polyprotein accessory proteins comprise nucleocapsid (NC), capsid protein (CA), matrix protein (MA), p6, viral infectivity factor (Vif), transactivator-of transcription (Tat), negative regulatory factor (Nef), viral protein R (Vpr), and viral protein u (Vpu).

15. The composition of embodiment 14, wherein the Gag polyprotein accessory proteins are encoded by the Gag polyprotein.

16. The composition of any one of embodiments 1-15, wherein the nucleic acid molecules of (i) and (ii) are RNA molecules or DNA molecules.

17. The composition of embodiment 16, wherein the nucleic acid molecules of (i) and (ii) are ssDNA molecules or dsDNA molecules.

18. The composition of embodiment 16, wherein the nucleic acid molecules of (i) and (ii) are ssRNA molecules.

19. The composition of any one of embodiments 1-18, wherein the nucleic acid molecule of (ii) comprises two or more transgenes, and the transgenes are separated by one or more internal ribosome entry sites (IRESes) and/or one or more 2A peptide-encoding sequences.

20. The composition of any one of embodiments 1-19, wherein the nucleic acid molecule of (ii) further comprises one or more enhancers.

21. The composition of embodiment 20, wherein the one or more enhancers comprise a woodchuck hepatitis virus posttranscriptional regulatory element.

22. The composition of any one of embodiments 1-21, wherein the one or more nucleic acid molecules of (i) and/or (ii) are RNA molecules and comprise one or more modifications selected from modified ribonucleosides, a 5'-7mG cap structure, and a poly (rA) tail.

23. The composition of embodiment 22, wherein the modified ribonucleoside is pseudouridine or a derivative of pseudouridine.

24. The composition of any one of embodiments 1-23, wherein the nucleic acid molecule of (ii) is an RNA molecule and further comprises one or more modifications selected from a 5'-7mG cap structure and a poly (rA) tail.

25. The composition of any one of embodiments 1-24, wherein the Pol proteins and/or LTRs are based on Pol proteins and/or LTRs are from human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), bovine immunodeficiency virus (BIV), human foamy virus (HFV), murine leukemia virus (MLV), Moloney murine leukemia virus (MoLV), Friend virus (FV), Abelson murine leukemia virus (A-MLV), murine stem cell virus (MSCV), mouse mammary tumor virus (MMTV), Moloney murine sarcoma virus (MoMSV). Rous sarcoma virus (RSV). Fujinami sarcoma virus (FuSV), FBR murine osteosarcoma virus (FBR MSV), Avian myelocytomatosis virus-29 (MC29), Avian erythroblastosis virus (AEV), human T-cell leukemia virus (HTLV).

26. The composition of any one of embodiments 1-25, wherein the composition is packaged in a non-viral delivery system.

27. The composition of embodiment 26, wherein the composition is packaged in lipid nanoparticles.

28. A composition comprising:
(i) a first RNA molecule comprising: a 5' untranslated region (UTR), a nucleic acid sequence encoding a retroviral Pol polyprotein, and a 3' UTR; and
(ii) a second RNA molecule comprising one or more reverse transcriptase priming elements and one or more promoter sequences operably linked to one or more transgenes, between a 5' long terminal repeat (LTR) and a 3' LTR;
wherein the composition does not contain nucleic acid sequences that express proteins encoded by retroviral rev and env genes, and wherein the composition is packaged in a non-viral delivery system.

29. The composition of embodiment 28, wherein the RNA molecules of (i) and (ii) are ssRNA molecules.

30. The composition of any one of embodiments 28-29, further comprising a third RNA molecule encoding one or more accessory proteins selected from nucleocapsid (NC), capsid protein (CA), viral infectivity factor (Vif), transactivator-of transcription (Tat), negative regulatory factor (Nef), viral protein R (Vpr), and viral protein u (Vpu).

31. The composition of embodiment 28, wherein the first RNA molecule further comprises a nucleic acid sequence encoding one or more accessory proteins selected from NC. CA, Vif, Tat, Nef, Vpr, and Vpu.

32. The composition of any one of embodiments 28-31, wherein the second RNA molecule comprises two or more transgenes, and the transgenes are separated by one or more internal ribosome entry sites (IRESes) and/or one or more sequences encoding a 2A peptide-encoding sequence.

33. The composition of any one of embodiments 28-32, wherein the second RNA molecule further comprises one or more enhancers.

34. The composition of embodiment 33, wherein the one or more enhancers comprise a woodchuck hepatitis virus posttranscriptional regulatory element.

35. The composition of any one of embodiments 28-34, wherein the first RNA molecule comprises one or more modifications selected from modified nucleosides, a 5'-7mG cap structure, and a poly (rA) tail.

36. The composition of any one of embodiments 28-35, wherein the second RNA molecule comprises one or more modification selected from a 5'-7mG cap structure and a poly (rA) tail.

37. The composition of any one of embodiments 1-36, wherein the one or more promoters comprise one or more tissue-specific or cell-specific promoters.

38. The composition of embodiment 37, wherein the one or more tissue-specific or cell-specific promoters are specific to bone marrow, hematopoietic stem cells (HSCs), epithelial cells, liver cells, ocular cells, muscle cells, or T cells.

39. The composition of any one of embodiments 1-36, wherein the one or more promoters comprise an hCMV promoter.

40. The composition of any one of embodiments 1-39, wherein the one or more transgenes encode one or more therapeutic molecules, diagnostic molecules, or reporter molecules, or fragments thereof.

41. The composition of embodiment 40, wherein the one or more transgenes encode one or more therapeutic proteins, diagnostic proteins, or reporter proteins, or fragments thereof.

42. The composition of embodiment 41, wherein the therapeutic protein is beta-globin, cystic fibrosis transmembrane conductance regulator (CFTR), Factor VIII, dystrophin, or RP GTPase regulator (RPGR).

43. The composition of embodiment 41, wherein the reporter protein is a fluorescent protein or luciferase.

44. The composition of any one of embodiments 38-43, wherein the Pol proteins, accessory proteins, and/or LTRs are based on Pol proteins, accessory proteins, and/or LTRs from human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), bovine immunodeficiency virus (BIV), human foamy virus (HFV), murine leukemia virus (MLV), Moloney murine leukemia virus (MoLV), Friend virus (FV), Abelson murine leukemia virus (A-MLV), murine stem cell virus (MSCV), mouse mammary tumor virus (MMTV), Moloney murine sarcoma virus (MoMSV), Rous sarcoma virus (RSV), Fujinami sarcoma virus (FuSV), FBR murine osteosarcoma virus (FBR MSV), Avian myelocytomatosis virus-29 (MC29), Avian erythroblastosis virus (AEV), human T-cell leukemia virus (HTLV).

45. The composition of any one of embodiment 26 or 28-44, wherein the non-viral delivery system is targeted to a specific tissue or cell type.

46. The composition of embodiment 45, wherein the specific tissue or cell type is bone marrow, HSCs, epithelial cells, liver cells, ocular cells, muscle cells, or T cells.

47. The composition of any one of embodiments 28-46, wherein the non-viral delivery system is a lipid nanoparticle, a liposome, a polypeptide nanoparticle, a silica nanoparticle, a gold nanoparticle, a polymeric nanoparticle, a dendrimer, or a cationic nanoemulsion.

48. A method for expressing a gene in a subject in need thereof, the method comprising administering to the subject an effective amount of the composition of any one of embodiments 147, thereby expressing the one or more transgenes in the subject.

49. A method for expressing a gene in a cell, the method comprising delivering the composition of any one of embodiments 1-47 to the cell, thereby expressing the one or more transgenes in the cell.

50. A method of using the composition of any one of embodiments 1-47, the method comprising delivering the composition to a subject, thereby expressing the one or more transgenes in the subject.

51. A method of treating a disease or condition in a subject in need thereof, the method comprising delivering the composition of any one of embodiments 1-47 to the subject, thereby expressing the one or more transgenes in the subject.

52. The method of embodiment 51, wherein the disease or condition is a genetic disease or condition.

53. The method of embodiment 51, wherein the disease or condition is a hereditary genetic disease or condition.

54. The method of embodiment 51, wherein the disease or condition is sickle cell disease, beta-thalassemia, haemophilia B, retinitis pigmentosa. Duchenne muscular dystrophy, cystic fibrosis, or cancer.

55. The method of any one of embodiments 48-54, wherein the one or more transgenes are integrated into the genome of a target cell.

56. The method of embodiment 55, wherein the one or more transgenes are stably expressed for at least a week, at least two weeks, at least a month, at least 6 months, at least a year, or for the lifetime of the subject.

57. A method of eliciting an immune response in a subject in need thereof, the method comprising administering to the subject an effective amount of the composition of any one of embodiments 1-47, thereby expressing the one or more transgenes in the subject.

58. The method of embodiment 57, wherein the subject has cancer, and the one or more transgenes encode a tumor antigen.

59. The method of embodiment 57, wherein the subject has or is at risk of contracting an infectious disease, and the one or more transgenes encode an antigen associated with the infectious disease.

60. The method of any one of embodiments 48-59, wherein the composition is delivered locally or systemically.

61. The method of embodiment 60, wherein the composition is delivered by injection, by inhalation, intravenously, intraperitoneally, subcutaneously, intramuscularly, orally, intranasally, by pulmonary administration, transdermally, transmucosally, or intratumorally.

62. One or more nucleic acid expression cassettes comprising a 5' UTR, a nucleic acid sequence encoding one or more retroviral Pol polyprotein components, and a 3' UTR, wherein the expression of Pol polyprotein components do not require translational slippage from an inline gag gene for use in the composition of any one of embodiments 1-47.

63. The nucleic acid expression cassette of embodiment 62, further comprising a nucleic acid sequence encoding one or more accessory proteins selected from nucleocapsid (NC), capsid protein (CA), viral infectivity factor (Vif), transactivator-of transcription (Tat), negative regulatory factor (Nef), viral protein R (Vpr), and viral protein u (Vpu).

64. The nucleic acid expression cassette of embodiment 62 or 63, wherein the Pol proteins and/or accessory proteins are based on Pol proteins and accessory proteins from: human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), bovine immunodeficiency virus (BIV), human foamy virus (HFV), murine leukemia virus (MLV), Moloney murine leukemia virus (MoLV), Friend virus (FV), Abelson murine leukemia virus (A-MLV), murine stem cell virus (MSCV), mouse mammary tumor virus (MMTV). Moloney murine sarcoma virus (MoMSV), Rous sarcoma virus (RSV), Fujinami sarcoma virus (FuSV), FBR murine osteosarcoma virus (FBR MSV), Avian myelocytomatosis virus-29 (MC29), Avian erythroblastosis virus (AEV), human T-cell leukemia virus (HTLV).

65. A method of producing an RNA molecule, comprising in vitro transcribing the nucleic acid expression cassette of any one of embodiments 62-64.

66. A kit comprising one or more containers, the one or more containers comprising the composition of any one of embodiments 1-47, or the nucleic acid expression cassette of any one of embodiments 62-65.

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents, and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion. i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B" when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently. "at least one of A or B," or, equivalently "at least one of A and/or B") can refer, in one embodiment, to at least one, optionally including more than one, A, with no B present (and optionally including elements other than B); in another embodiment, to at least one, optionally including more than one. B, with no A present (and optionally including elements other than A); in yet another embodiment, to at least one, optionally including more than one, A. and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

What is claimed is:

1. A composition comprising:
   (i) one or more nucleic acid molecules encoding two or more Pol polyprotein components flanked by 5' and 3' untranslated regions (UTRs), wherein the two or more Pol polyprotein components encoded by the one or more nucleic acid molecules comprise a reverse transcriptase and an integrase; and
   (ii) a ribonucleic acid (RNA) molecule comprising one or more reverse transcriptase priming elements and one or more promoter sequences operably linked to one or more transgenes, between a 5' long terminal repeat (LTR) and a 3' LTR,
   wherein the composition does not contain nucleic acid sequences that express proteins encoded by either the retroviral rev gene or the retroviral env gene, or both.

2. The composition of claim 1, wherein the composition is capable of integrating the one or more transgenes into a host genome in the absence of functional retroviral Rev and/or Env proteins.

3. The composition of claim 1, wherein the expression of the one or more Pol polyprotein components does not require translational slippage from an inline gag gene.

4. The composition of claim 1, wherein the one or more nucleic acid molecules of (i) is one nucleic acid molecule comprising a 5' UTR, a nucleic acid sequence encoding at least the Pol polyprotein components reverse transcriptase and integrase, and a 3' UTR.

5. The composition of claim 1, wherein the Pol polyprotein components reverse transcriptase and integrase are expressed on one nucleic acid molecule with one or more polycistronic elements.

6. The composition of claim 5, wherein the one or more polycistronic elements comprise an intervening internal ribosome entry site (IRES), a 2A peptide-encoding sequence, or both.

7. The composition of claim 1, wherein the one or more nucleic acid molecules of (i) comprise nucleic acid sequences encoding one or more accessory proteins.

8. The composition of claim 1, wherein the composition does not comprise a nucleic acid sequence encoding the matrix protein.

9. The composition of claim 1, wherein the one or more nucleic acid molecules of (i) comprise at least one mutation in one or more intrinsic instability (INS) elements.

10. The composition of claim 1, wherein the one or more nucleic acid molecules of (i) encode an integrase polypeptide comprising an N-terminal methionine-glycine dipeptide.

11. The composition of claim 1, wherein the one or more Pol polyprotein components are fused to a homing protein.

12. The composition of claim 1, wherein the one or more nucleic acid molecules of (i) and/or the RNA molecule of (ii) are codon optimized for expression in a host cell.

13. The composition of claim 1, wherein the composition further comprises a priming oligonucleotide.

14. The composition of claim 1, wherein the composition is packaged in a non-viral delivery system.

15. The composition of claim 1, wherein the one or more promoters comprise one or more tissue-specific or cell-specific promoters.

16. A method for expressing a gene in a subject, the method comprising administering to the subject an effective amount of the composition of claim 1, thereby expressing the one or more transgenes in the subject.

17. A method for expressing a gene in a cell, the method comprising delivering an effective amount of the composition of claim 1 to the cell, thereby expressing the one or more transgenes in the cell.

18. A method of eliciting an immune response in a subject, the method comprising administering to the subject an effective amount of the composition of claim 1, thereby expressing the one or more transgenes in the subject that are capable of eliciting an immune response.

19. A kit comprising one or more containers, wherein the one or more containers comprises the composition of claim 1.

20. The composition of claim 1, wherein the one or more nucleic acid molecules of (i) is one or more RNA molecules.

21. The composition of claim 20, wherein the one or more RNA molecules comprise one or more modifications selected from modified ribonucleosides, a 5'-7 mG cap structure, and a poly (rA) tail; and/or the RNA molecule of (ii) further comprises one or more modifications selected from modified ribonucleosides, a 5'-7 mG cap structure, and a poly (rA) tail.

22. A composition comprising:
   (i) a first RNA molecule comprising: a 5' untranslated region (UTR), a nucleic acid sequence encoding two or more Pol polyprotein components, and a 3' UTR, wherein the two or more Pol polyprotein components comprise a reverse transcriptase and an integrase; and
   (ii) a second RNA molecule comprising one or more reverse transcriptase priming elements and one or more promoter sequences operably linked to one or more transgenes, between a 5' long terminal repeat (LTR) and a 3' LTR;
   wherein the composition is packaged in a non-viral delivery system.

23. One or more nucleic acid templates comprising a 5' UTR, a nucleic acid sequence encoding two or more retroviral Pol polyprotein components, and a 3' UTR, wherein the two or more retroviral Pol polyprotein components encoded by the one or more nucleic acid templates comprise a reverse transcriptase and an integrase, and wherein the expression of Pol polyprotein components does not require translational slippage from an inline gag-pol gene.

24. A method of producing an RNA molecule, the method comprising transcribing in vitro the nucleic acid template of claim 23.

* * * * *

SEQUENCE LISTING

```
<160> NUMBER OF SEQ ID NOS: 19

<210> SEQ ID NO 1
<211> LENGTH: 4664
<212> TYPE: DNA
<213> ORGANISM: Artificial Sequence
<220> FEATURE:
<223> OTHER INFORMATION: Synthetic

<400> SEQUENCE: 1
agaccagatc tgagcctggg agctctctgg ctaactaggg aacccactgc ttaagcctca      60
```

```
ataaagcttg ccttgagtgc ttcaagtagt gtgtgcccgt ctgttgtgtg actctggtaa    120
ctagagatcc ctcagaccct tttagtcagt gtggaaaatc tctagcagtg gcgcccgaac    180
agggacttga aagcgaaagg gaaaccagag gagctctctc gacgcaggac tcggcttgct    240
gaagcgcgca cggcaagagg cgaggggcgg cgactggtga gtacgccaaa aattttgact    300
agcggaggct agaaggagag agatgggtgc gagagcgtca gtattaagcg ggggagaatt    360
agatcgcgat gggaaaaaat tcggttaagg ccagggggaa agaaaaaata taaattaaaa    420
catatagtat gggcaagcag ggagctagaa cgattcgcag ttaatcctgg cctgttagaa    480
acatcagaag gctgtagaca aatactggga cagctacaac catcccttca gacaggatca    540
gaagaactta gatcattata taatacagta gcaaccctct attgtgtgca tcaaaggata    600
gagataaaag acaccaagga agctttagac aagatagagg aagagcaaaa caaaagtaag    660
accaccgcac agcaagcggc cgctgatctt cagacctgga ggaggagata tgagggacaa    720
ttggagaagt gaattatata aatataaagt agtaaaaatt gaaccattag gagtagcacc    780
caccaaggca aagagaagag tggtgcagag agaaaaaaga gcagtgggaa taggagcttt    840
gttccttggg ttcttgggag cagcaggaag cactatgggc gcagcgtcaa tgacgctgac    900
ggtacaggcc agacaattat tgtctggtat agtgcagcag cagaacaatt tgctgagggc    960
tattgaggcg caacagcatc tgttgcaact cacagtctgg ggcatcaagc agctccaggc    1020
aagaatcctg gctgtggaaa gatacctaaa ggatcaacag ctcctgggga tttgggggtg    1080
ctctggaaaa ctcatttgca ccactgctgt gccttggaat gctagttgga gtaataaatc    1140 tctgaacag atttggaatc acacgacctg gatggagtgg gacagagaaa ttaacaatta    1200
cacaagctta atacactcct taattgaaga atcgcaaaac cagcaagaaa agaatgaaca    1260
agaattattg gaattagata aatgggcaag tttgtggaat tggtttaaca taacaaattg    1320
gctgtggtat ataaaattat tcataatgat agtaggaggc ttggtaggtt taagaatagt    1380
ttttgctgta ctttctatag tgaatagagt taggcaggga tattcaccat tatcgtttca    1440
gacccacctc ccaaccccga ggggacccga caggcccgaa ggaatagaag aagaaggtgg    1500
agagagagac agagacagat ccattcgatt agtgaacgga tctcgacggt atcggttaac    1560
ttttaaaaga aaagggggga ttggggggta cagtgcaggg gaaagaatag tagacataat    1620
agcaacagac atacaaacta agaaattaca aaaacaaatt acaaaaattc aaaatttat    1680 cgataagctt gggagttccg cgttacataa cttacggtaa atggcccgcc tggctgaccg    1740
cccaacgacc cccgcccatt gacgtcaata atgacgtatg ttcccatagt aacgccaata    1800
gggactttcc attgacgtca atgggtggag tatttacggt aaactgccca cttggcagta    1860
catcaagtgt atcatatgcc aagtacgccc cctattgacg tcaatgacgg taaatggccc    1920
gcctggcatt atgcccagta catgacctta tgggactttc ctacttggca gtacatctac    1980
gtattagtca tcgctattac catggtgatg cggttttggc agtacatcaa tgggcgtgga    2040
tagcggtttg actcacgggg atttccaagt ctccacccca ttgacgtcaa tgggagtttg    2100
ttttggcacc aaaatcaacg ggactttcca aaatgtcgta caactccgcc ccattgacg    2160 caaatgggcg gtaggcgtgt acggtggag gtctatataa gcagagctcg tttagtgaac    2220
cgtcagatcg cctggagacg ccatccacgc tgttttgacc tccatagaag acaccgactc    2280
tagaggatcc actagtccag tgtggtggaa ttctgcagat atcaacaagt ttgtacaaaa    2340
aagcaggctc caccatggtg agcaagggcg aggagctgtt caccggggtg gtgcccatcc    2400
tggtcgagct ggacggcgac gtaaacggcc acaagttcag cgtgtccggc gagggcgagg    2460
```

```
gcgatgccac ctacggcaag ctgaccctga agttcatctg caccaccggc aagctgcccg    2520
tgccctggcc caccctcgtg accaccttca cctacgcgt gcagtgcttc gcccgctacc     2580
ccgaccacat gaagcagcac gacttcttca gtccgccat gcccgaaggc tacgtccagg     2640
agcgcaccat cttcttcaag gacgacggca actacaagac ccgcgccgag gtgaagttcg    2700
agggcgacac cctggtgaac cgcatcgagc tgaagggcat cgacttcaag gaggacggca    2760
acatcctggg gcacaagctg gagtacaact acaacagcca caggtctat atcaccgccg     2820 acaagcagaa gaacggcatc aaggtgaact tcaagacccg ccacaacatc gaggacggca    2880
gcgtgcagct cgccgaccac taccagcaga caccccat cggcgacggc cccgtgctgc      2940
tgcccgacaa ccactacctg agcacccagt ccgccctgag caaagacccc aacgagaagc    3000
gcgatcacat ggtcctgctg gagttcgtga ccgccgccgg gatcactctc ggcatggacg    3060
agctgtacaa gtaaacccag ctttcttgta caaagtggtt gatatccagc acagtggcgg    3120
ccgctcgagt ctagagggcc cgcggttcga aggtaagcct atccctaacc ctctcctcgg    3180
tctcgattct acgcgtaccg gttagtaatg atcgacaatc aacctctgga ttacaaaatt    3240
tgtgaaagat tgactggtat tcttaactat gttgctcctt ttacgctatg tggatacgct    3300
gctttaatgc ctttgtatca tgctattgct tcccgtatgg ctttcatttt ctcctccttg    3360
tataaatcct ggttgctgtc tctttatgag gagttgtggc ccgttgtcag gcaacgtggc    3420
gtggtgtgca ctgtgtttgc tgacgcaacc cccactggtt ggggcattgc caccacctgt    3480
cagctccttt ccgggacttt cgctttcccc ctccctattg ccacggcgga actcatcgcc    3540
gcctgccttg cccgctgctg acagggggct cggctgttgg gcactgacaa ttccgtggtg    3600
ttgtcgggga gctgacgtc cttcccatgg ctgctcgcct gtgttgccac ctggattctg    3660
cgcgggacgt ccttctgcta cgtcccttcg gccctcaatc cagcggacct tccttcccgc    3720
ggcctgctgc cggctctgcg gcctcttccg cgtcttcgcc ttcgccctca gacgagtcgg    3780
atctcccttt gggccgcctc cccgcctggc gatggtaccg gtgtggaaag tccccaggct    3840
ccccagcagg cagaagtatg caaagcatgc atctcaatta gtcagcaacc aggtgtggaa    3900
agtccccagg ctccccagca ggcagaagta tgcaaagcat gcatctcaat tagtcagcaa    3960
ccatagtccc gcccctaact ccgcccatcc cgccccctaac tccgcccagt tccgcccatt    4020
ctccgcccca tggctgacta attttttttta tttatgcaga ggccgaggcc gcctctgcct    4080
ctgagctatt ccagaagtag tgaggaggct ttttggagg cctaggcttt tgcaaaaagc     4140
tcccgggagc ttgtatatcc attttcggat ctgatcagca cgtgcacaat tcgagctcgg    4200
tacctttaag accaatgact tacaaggcag ctgtagatct tagccacttt ttaaaagaaa    4260
aggggggact ggaagggcta attcactccc aacgaagaca agatctgctt tttgcttgta    4320
ctgggtctct ctggttagac cagatctgag cctgggagct ctctggctaa ctagggaacc    4380
cactgcttaa gcctcaataa agcttgcctt gagtgcttca agtagtgtgt gcccgtctgt    4440
tgtgtgactc tggtaactag agatccctca gaccctttta gtcagtgtgg aaaatctcta    4500
gcagtagtag ttcatgtcat cttattattc agtatttata acttgcaaag aaatgaatat    4560
cagagagtga gaggaacttg tttattgcag cttataatgg ttacaaataa agcaatagca    4620
tcacaaattt cacaaataaa gcatttttttt cactgcacct aagg                   4664

<210> SEQ ID NO 2
<211> LENGTH: 4664
<212> TYPE: DNA
```

<213> ORGANISM: Artificial Sequence
<220> FEATURE:
<223> OTHER INFORMATION: Synthetic

<400> SEQUENCE: 2

```
agaccagatc tgagcctggg agctctctgg ctaactaggg aacccactgc ttaagcctca      60
ataaagcttg ccttgagtgc ttcaagtagt gtgtgcccgt ctgttgtgtg actctggtaa     120
ctagagatcc ctcagaccct tttagtcagt gtggaaaatc tctagcagtg gcgcccgaac     180
agggacttga aagcgaaagg gaaaccagag gagctctctc gacgcaggac tcggcttgct     240
gaagcgcgca cggcaagagg cgaggggcgg cgactggtga gtacgccaaa aattttgact     300
agcggaggct agaaggagag agatgggtgc gagagcgtca gtattaagcg ggggagaatt     360
agatcgcgat gggaaaaaat tcggttaagg ccagggggaa agaaaaaata taaattaaaa     420
catatagtat gggcaagcag ggagctagaa cgattcgcag ttaatcctgg cctgttagaa     480
acatcagaag gctgtagaca atactgggac agctacaacc atcccttcag acaggatcag    540
aagaactta gatcattata taatacagta gcaaccctct attgtgtgca tcaaaggata     600
gagataaaag acaccaagga agctttagac aagatagagg aagagcaaaa caaaagtaag     660
accaccgcac agcaagcggc cgctgatctt cagacctgga ggaggagata tgagggacaa     720
ttggagaagt gaattatata aatataaagt agtaaaaatt gaaccattag gagtagcacc     780
caccaaggca aagagaagag tggtgcagag agaaaaaaga gcagtgggaa taggagcttt     840
gttccttggg ttcttgggag cagcaggaag cactatgggc gcagcgtcaa tgacgctgac     900
ggtacaggcc agacaattat tgtctggtat agtgcagcag cagaacaatt tgctgagggc     960
tattgaggcg caacagcatc tgttgcaact cacagtctgg ggcatcaagc agctccaggc    1020
aagaatcctg gctgtggaaa gatacctaaa ggatcaacag ctcctgggga tttgggttg     1080
ctctggaaaa ctcatttgca ccactgctgt gccttggaat gctagttgga gtaataaatc    1140
tctggaacag atttggaatc acacgacctg gatggagtgg gacagagaaa ttaacaatta    1200
cacaagctta atacactcct taattgaaga atcgcaaaac cagcaagaaa agaatgaaca    1260
agaattattg gaattagata atgggcaagt ttgtggaat tggtttaaca taacaaattg    1320
gctgtggtat ataaaattat tcataatgat agtaggaggc ttggtaggtt taagaatagt    1380
ttttgctgta ctttctatag tgaatagagt taggcaggga tattcaccat tatcgtttca    1440
gacccacctc ccaaccccga ggggacccga caggcccgaa ggaatagaag aagaaggtgg    1500
agagagagac agagacagat ccattcgatt agtgaacgga tctcgacggt atcggttaac    1560
ttttaaaaga aaagggggga ttggggggta cagtgcaggg gaaagaatag tagacataat    1620
agcaacagac atacaaacta agaattacaa aaacaaatt acaaaaattc aaaattttat    1680
cgataagctt gggagttccg cgttacataa cttacggtaa atggcccgcc tggctgaccg    1740
cccaacgacc cccgcccatt gacgtcaata atgacgtatg ttcccatagt aacgccaata    1800
gggactttcc attgacgtca atgggtggag tatttacggt aaactgccca cttggcagta    1860
catcaagtgt atcatatgcc aagtacgccc cctattgacg tcaatgacgg taaatggccc    1920
gcctggcatt atgcccagta catgacctta tgggactttc ctacttggca gtacatctac    1980
gtattagtca tcgctattac catggtgatg cggttttggc agtacatcaa tgggcgtgga    2040
tagcggtttg actcacgggg atttccaagt ctccacccca ttgacgtcaa tgggagtttg    2100
ttttggcacc aaaatcaacg ggactttcca aatgtcgta acaactccgc cccattgacg    2160
caaatgggcg gtaggcgtgt acggtggag gtctatataa gcagagctcg tttagtgaac    2220
```

```
cgtcagatcg cctggagacg ccatccacgc tgttttgacc tccatagaag acaccgactc   2280
tagaggatcc actagtccag tgtggtggaa ttctgcagat atcaacaagt ttgtacaaaa   2340
aagcaggctc caccatggtg agcaagggcg aggagctgtt caccggggtg gtgcccatcc   2400
tggtcgagct ggacggcgac gtaaacggcc acaagttcag cgtgtccggc gagggcgagg   2460
gcgatgccac ctacggcaag ctgaccctga agttcatctg caccaccggc aagctgcccg   2520
tgcccctggc caccctcgtg accaccttcg gctacggcct gatgtgcttc gcccgctacc   2580
ccgaccacat gaagcagcac gacttcttca gtccgccat gcccgaaggc tacgtccagg   2640
agcgcaccat cttcttcaag gacgacggca actacaagac ccgcgccgag gtgaagttcg   2700
agggcgacac cctggtgaac cgcatcgagc tgaagggcat cgacttcaag gaggacggca   2760
acatcctggg gcacaagctg gagtacaact acaacagcca caacgtctat atcatggccg   2820
acaagcagaa gaacggcatc aaggtgaact tcaagatccg ccacaacatc gaggacggca   2880
gcgtgcagct cgccgaccac taccagcaga cacccccat cggcgacggc cccgtgctgc   2940
tgcccgacaa ccactacctg agctaccagt ccaaactgag caaagacccc aacgagaagc   3000
gcgatcacat ggtcctgctg gagttcgtga ccgccgccgg gatcactctc ggcatggacg   3060
agctgtacaa gtaaacccag cttttcttgta caaagtggtt gatatccagc acagtggcgg   3120
ccgctcgagt ctagagggcc cgcggttcga aggtaagcct atccctaacc ctctcctcgg   3180
tctcgattct acgcgtaccg gttagtaatg atcgacaatc aacctctgga ttacaaaatt   3240
tgtgaaagat tgactggtat tcttaactat gttgctcctt ttacgctatg tggatacgct   3300
gctttaatgc ctttgtatca tgctattgct tcccgtatgg ctttcatttt ctcctccttg   3360
tataaatcct ggttgctgtc tctttatgag gagttgtggc ccgttgtcag gcaacgtggc   3420
gtggtgtgca ctgtgtttgc tgacgcaacc cccactggtt ggggcattgc caccacctgt   3480
cagctccttt ccgggacttt cgctttcccc ctccctattg ccacggcgga actcatcgcc   3540
gcctgccttg cccgctgctg gacaggggct cggctgttgg gcactgacaa ttccgtggtg   3600
ttgtcgggga agctgacgtc ctttccatgg ctgctcgcct gtgttgccac ctggattctg   3660
cgcgggacgt ccttctgcta cgtcccttcg gccctcaatc cagcggacct tccttcccgc   3720
ggcctgctgc cggctctgcg gcctcttccg cgtcttcgcc ttcgccctca gacgagtcgg   3780
atctcccttt gggccgcctc cccgcctggc gatggtaccg gtgtggaaag tccccaggct   3840
ccccagcagg cagaagtatg caaagcatgc atctcaatta gtcagcaacc aggtgtggaa   3900
agtccccagg ctccccagca ggcagaagta tgcaaagcat gcatctcaat tagtcagcaa   3960
ccatagtccc gcccctaact ccgcccatcc cgcccctaac tccgcccagt tccgcccatt   4020
ctccgcccca tggctgacta atttttttta tttatgcaga ggccgaggcc gcctctgcct   4080
ctgagctatt ccagaagtag tgaggaggct ttttggaggg cctaggcttt tgcaaaaagc   4140
tcccgggagc ttgtatatcc attttcggat ctgatcagca cgtgcacaat tcgagctcgg   4200
tacctttaag accaatgact tacaaggcag ctgtagatct tagccacttt ttaaaagaaa   4260 agggggact ggaagggcta attcactccc aacgaagaca agatctgctt tttgcttgta   4320
ctgggtctct ctggttagac cagatctgag cctgggagct ctctggctaa ctagggaacc   4380
cactgcttaa gcctcaataa agcttgcctt gagtgcttca agtagtgtgt gcccgtctgt   4440
tgtgtgactc tggtaactag agatccctca gacccttttta gtcagtgtgg aaaatctcta   4500
gcagtagtag ttcatgtcat cttattattc agtatttata acttgcaaag aaatgaatat   4560
```

```
cagagagtga gaggaacttg tttattgcag cttataatgg ttacaaataa agcaatagca    4620
tcacaaattt cacaaataaa gcattttttt cactgcacct aagg                    4664

<210> SEQ ID NO 3
<211> LENGTH: 4346
<212> TYPE: DNA
<213> ORGANISM: Artificial Sequence
<220> FEATURE:
<223> OTHER INFORMATION: Synthetic

<400> SEQUENCE: 3
agaccagatc tgagcctggg agctctctgg ctaactaggg aacccactgc ttaagcctca      60
ataaagcttg ccttgagtgc ttcaagtagt gtgtgcccgt ctgttgtgtg actctggtaa     120
ctagagatcc ctcagaccct tttagtcagt gtggaaaatc tctagcagtg gcgcccgaac     180
agggacttga aagcgaaagg gaaaccagag gagctctctc gacgcaggac tcggcttgct     240
gaagcgcgca cggcaagagg cgaggggcgg cgactggtga gtacgccaaa aattttgact     300
agcggaggct agaaggagag agatgggtgc gagagcgtca gtattaagcg gggagaatt     360 agatcgcgat gggaaaaaat tcggttaagg ccaggggga agaaaaaata taaattaaaa     420
catatagtat gggcaagcag ggagctagaa cgattcgcag ttaatcctgg cctgttagaa     480
acatcagaag gctgtagaca atactggga cagctacaac catcccttca gacaggatca     540
gaagaactta gatcattata taatacagta gcaaccctct attgtgtgca tcaaggata    600 gagataaaag acaccaagga agctttagac aagatagagg aagagcaaaa caaaagtaag     660
accaccgcac agcaagcggc cgctgatctt cagacctgga ggaggagata tgagggacaa     720
ttggagaagt gaattatata aatataaagt agtaaaaatt gaaccattag gagtagcacc     780
caccaaggca agagaagag tggtgcagag agaaaaaaga gcagtgggaa taggagcttt     840
gttccttggg ttcttgggag cagcaggaag cactatgggc gcagcgtcaa tgacgctgac     900
ggtacaggcc agacaattat tgtctggtat agtgcagcag cagaacaatt tgctgagggc     960
tattgaggcg caacagcatc tgttgcaact cacagtctgg gcatcaagc agctccaggc    1020 aagaatcctg gctgtggaaa gatacctaaa ggatcaacag ctcctgggga tttgggttg    1080 ctctggaaaa ctcatttgca ccactgctgt gccttggaat gctagttgga gtaataaatc    1140
tctggaacag atttggaatc acacgacctg gatggagtgg gacagagaaa ttaacaatta    1200
cacaagctta atacactcct taattgaaga atcgcaaaac cagcaagaaa agaatgaaca    1260
agaattattg gaattagata atgggcaag tttgtggaat tggtttaaca taacaaattg    1320
gctgtggtat ataaaattat tcataatgat agtaggaggc ttggtaggtt taagaatagt    1380 tttgctgta ctttctatag tgaatagagt taggcaggga tattcaccat tatcgtttca    1440
gacccacctc ccaaccccga ggggacccga caggcccgaa ggaatagaag aagaaggtgg    1500
agagagagac agagacagat ccattcgatt agtgaacgga tctcgacggt atcggttaac    1560
ttttaaaaga aaaggggga ttgggggta cagtgcaggg gaaagaatag tagacataat    1620
agcaacagac atacaaacta agaattaca aaacaaatt acaaaaatc aaaatttat    1680 cgataagctt gggagttccg cgttacataa cttacggtaa atggcccgcc tggctgaccg    1740
cccaacgacc cccgcccatt gacgtcaata atgacgtatg ttcccatagt aacgccaata    1800
gggactttcc attgacgtca atgggtggag tatttacggt aaactgccca cttggcagta    1860
catcaagtgt atcatatgcc aagtacgccc cctattgacg tcaatgacgg taaatggccc    1920
gcctggcatt atgcccagta catgacctta tgggactttc ctacttggca gtacatctac    1980
```

```
gtattagtca tcgctattac catggtgatg cggttttggc agtacatcaa tgggcgtgga    2040
tagcggtttg actcacgggg atttccaagt ctccacccca ttgacgtcaa tgggagtttg    2100
ttttggcacc aaaatcaacg ggactttcca aaatgtcgta caactccgcc cccattgacg    2160
caaatgggcg gtaggcgtgt acggtgggag gtctatataa gcagagctcg tttagtgaac    2220
cgtcagatcg cctggagacg ccatccacgc tgttttgacc tccatagaag acaccgactc    2280
tagaggatcc actagtccag tgtggtggaa ttctgcagat atcaacaagt ttgtacaaaa    2340
aagcaggctc caccatggct aagacttccg aacagagggt gaacattgct acactgctga    2400
cagaaaataa gaagaaaatc gtggataagg cttcccagga tctgtggcgg agacacccag    2460
acctgatcgc accaggagga attgctttct ctcagaggga ccgcgctctg tgcctgcgag    2520 attacgctg gttcctgcat ctgatcacct tttgtctgct ggccggagat aagggcccca    2580
tcgagtctat tgggctgatc agtattcgag aaatgtataa ctcactggga gtgcccgtcc    2640
ctgcaatgat ggagagcatt agatgcctga agaagccag cctgtccctg ctggacgaag    2700
aggacgccaa cgagaccgca ccctactttg attacattat taaggctatg agctaaaccc    2760
agcttttctt gtacaaagtgg ttgatatcca gcacagtggc ggccgctcga gtctagaggg    2820
cccgcggttc gaaggtaagc ctatccctaa ccctctcctc ggtctcgatt ctacgcgtac    2880
cggttagtaa tgatcgacaa tcaacctctg gattacaaaa tttgtgaaag attgactggt    2940
attcttaact atgttgctcc ttttacgcta tgtggatacg ctgctttaat gcctttgtat    3000
catgctattg cttcccgtat ggctttcatt ttctcctcct tgtataaatc ctggttgctg    3060
tctctttatg aggagttgtg gcccgttgtc aggcaacgtg gcgtggtgtg cactgtgttt    3120
gctgacgcaa ccccccactgg ttggggcatt gccaccacct gtcagctcct ttccgggact    3180
ttcgctttcc ccctccctat tgccacggcg gaactcatcg ccgcctgcct tgcccgctgc    3240
tggacagggg ctcggctgtt gggcactgac aattccgtgg tgttgtcggg gaagctgacg    3300 tccttttccat ggctgctcgc ctgtgttgcc acctggattc tgcgcgggac gtccttctgc    3360
tacgtccctt cggccctcaa tccagcggac cttccttccc gcggcctgct gccggctctg    3420
cggcctcttc cgcgtcttcg ccttcgccct cagacgagtc ggatctccct ttgggccgcc    3480
tccccgcctg gcgatggtac cggtgtggaa agtccccagg ctccccagca ggcagaagta    3540
tgcaaagcat gcatctcaat tagtcagcaa ccaggtgtgg aaagtcccca ggctccccag    3600
caggcagaag tatgcaaagc atgcatctca attagtcagc aaccatagtc cgcccctaa    3660 ctccgcccat cccgccccta actccgccca gttccgccca ttctccgccc catggctgac    3720 taatttttttt tatttatgca gaggccgagg ccgcctctgc ctctgagcta ttccagaagt    3780
agtgaggagg ctttttttgga ggcctaggct tttgcaaaaa gctcccggga gcttgtatat    3840 ccatttttcgg atctgatcag cacgtgcaca attcgagctc ggtaccttta agaccaatga    3900
cttacaaggc agctgtagat cttagccact ttttaaaaga aaaggggggga ctggaagggc    3960 taattcactc ccaacgaaga caagatctgc tttttgcttg tactgggtct ctctggttag    4020
accagatctg agcctgggag ctctctggct aactagggaa cccactgctt aagcctcaat    4080
aaagcttgcc ttgagtgctt caagtagtgt gtgcccgtct gttgtgtgac tctggtaact    4140
agagatccct cagacccttt tagtcagtgt ggaaaatctc tagcagtagt agttcatgtc    4200
atcttattat tcagtatttta taacttgcaa agaaatgaat atcagagagt gagaggaact    4260
tgtttattgc agcttataat ggttacaaat aaagcaatag catcacaaat ttcacaaata    4320
``` aagcatttttt ttcactgcac ctaagg                                        4346

<210> SEQ ID NO 4
<211> LENGTH: 4663
<212> TYPE: DNA
<213> ORGANISM: Artificial Sequence
<220> FEATURE:
<223> OTHER INFORMATION: Synthetic

<400> SEQUENCE: 4
gggtctctct ggttagacca gatctgagcc tgggagctct ctggctaact agggaaccca     60
ctgcttaagc ctcaataaag cttgccttga gtgcttcaag tagtgtgtgc ccgtctgttg    120
tgtgactctg gtaactagag atccctcaga cccttttagt cagtgtggaa aatctctagc    180
agtggcgccc gaacagggac ttgaaagcga aagggaaacc agaggagctc tctcgacgca    240
ggactcggct tgctgaagcg cgcacggcaa gaggcgaggg gcggcgactg gtgagtacgc    300
caaaaatttt gactagcgga ggctagaagg agagagatgg gtgcgagagc gtcagtatta    360
agcgggggag aattagatcg cgatgggaaa aaattcggtt aaggccaggg ggaaagaaaa    420
aatataaatt aaaacatata gtatgggcaa gcagggagct agaacgattc gcagttaatc    480
ctggcctgtt agaaacatca gaaggctgta gacaaatact gggacagcta caaccatccc    540
ttcagacagg atcagaagaa cttagatcat tatataatac agtagcaacc ctctattgtg    600
tgcatcaaag gatagagata aaagacacca aggaagcttt agacaagata gaggaagagc    660
aaaacaaaag taagaccacc gcacagcaag cggccgctga tcttcagacc tggaggagga    720
gatatgaggg acaattggag aagtgaatta tataaatata agtagtaaa aattgaacca     780
ttaggagtag cacccaccaa ggcaaagaga agagtggtgc agagagaaaa aagagcagtg    840
ggaataggag ctttgttcct tgggttcttg ggagcagcag gaagcactat gggcgcagcg    900
tcaatgacgc tgacggtaca ggccagacaa ttattgtctg gtatagtgca gcagcagaac    960
aatttgctga gggctattga ggcgcaacag catctgttgc aactcacagt ctggggcatc   1020
aagcagctcc aggcaagaat cctggctgtg gaaagatacc taaaggatca acagctcctg   1080
gggatttggg gttgctctgg aaaactcatt tgcaccactg ctgtgccttg gaatgctagt   1140
tggagtaata aatctctgga acagatttgg aatcacacga cctggatgga gtgggacaga   1200
gaaattaaca attacacaag cttaatacac tccttaattg aagaatcgca aaaccagcaa   1260
gaaaagaatg aacaagaatt attggaatta gataaatggg caagtttgtg gaattggttt   1320
aacataacaa attggctgtg gtatataaaa ttattcataa tgatagtagg aggcttggta   1380
ggtttaagaa tagttttttgc tgtactttct atagtgaata gagttaggca gggatattca   1440
ccattatcgt ttcagaccca cctcccaacc ccgaggggac ccgacaggcc cgaaggaata   1500
gaagaagaag gtggagagag agacagagac agatccattc gattagtgaa cggatctcga   1560
cggtatcggt taactttaa agaaaagggg ggattggggg ggtacagtgc agggaaaga    1620
atagtagaca taatagcaac agacatacaa actaaagaat tacaaaaaca aattacaaaa   1680
attcaaaatt ttatcgataa gcttgggagt tccgcgttac ataacttacg gtaaatggcc   1740
cgcctggctg accgcccaac gacccccgcc cattgacgtc aataatgacg tatgttccca   1800
tagtaacgcc aatagggact ttccattgac gtcaatgggt ggagtattta cggtaaactg   1860
cccacttggc agtacatcaa gtgtatcata tgccaagtac gccccctatt gacgtcaatg   1920
acggtaaatg gcccgcctgg cattatgccc agtacatgac cttatgggac tttcctactt   1980
ggcagtacat ctacgtatta gtcatcgcta ttaccatggt gatgcggttt tggcagtaca   2040

```
tcaatgggcg tggatagcgg tttgactcac ggggatttcc aagtctccac cccattgacg    2100
tcaatgggag tttgttttgg caccaaaatc aacgggactt tccaaaatgt cgtaacaact    2160
ccgccccatt gacgcaaatg ggcggtaggc gtgtacggtg ggaggtctat ataagcagag    2220
ctcgtttagt gaaccgtcag atcgcctgga gacgccatcc acgctgtttt gacctccata    2280
gaagacaccg actctagagg atccactagt ccagtgtggt ggaattctgc agatatcaac    2340
aagtttgtac aaaaaagcag gctccaccat ggtgagcaag ggcgaggagc tgatcaagga    2400
gaacatgaga agcaagctgt acctggaagg cagcgtgaac ggccaccagt tcaagtgcac    2460
ccacgaaggg gagggcaagc cctacgaggg caagcagacc gcgaggatca aggtggtgga    2520
gggaggcccc ctgccgttcg cattcgacat cctggccacc atgtttatgt acgggagcaa    2580
ggtgttcatc aagtaccccg ccgacctccc cgattatttt aagcagtcct tccctgaggg    2640
cttcacatgg gagagagtca tggtgttcga agacggggc gtgctgaccg ccacccagga    2700
caccagcctc caggacggcg agctcatcta caacgtcaag ctcagagggg tgaacttccc    2760
agccaacggc cccgtgatgc agaagaaaac actgggctgg gagcccagca ccgagaccat    2820 gtacccccgct gacggcggcc tggaaggcag atgcgacaag aagctgaagc tcgtgggcgg    2880
gggccacctg cacgtcaact tcaagaccac atacaagtcc aagaaacccg tgaagatgcc    2940
cggcgtccac tacgtggacc gcagactgga aagaatcaag gaggccgaca acgagaccta    3000
cgtcgagcag tacgagcacg ctgtggccag atactccaac ctgggcggag catggacga    3060 gctgtacaag taaacccagc tttcttgtac aaagtggttg atatccagca cagtggcggc    3120
cgctcgagtc tagagggccc gcggttcgaa ggtaagccta tccctaaccc tctcctcggt    3180
ctcgattcta cgcgtaccgg ttagtaatga tcgacaatca acctctggat tacaaaattt    3240
gtgaaagatt gactggtatt cttaactatg ttgctccttt tacgctatgt ggatacgctg    3300
ctttaatgcc tttgtatcat gctattgctt cccgtatggc tttcattttc tcctccttgt    3360
ataaatcctg gttgctgtct ctttatgagg agttgtggcc cgttgtcagg caacgtggcg    3420
tggtgtgcac tgtgtttgct gacgcaaccc ccactggttg gggcattgcc accacctgtc    3480
agctcctttc cgggactttc gctttccccc tccctattgc cacggcggaa ctcatcgccg    3540
cctgccttgc ccgctgctgg acaggggctc ggctgttggg cactgacaat tccgtggtgt    3600
tgtcggggaa gctgacgtcc tttccatggc tgctcgcctg tgttgccacc tggattctgc    3660
gcgggacgtc cttctgctac gtcccttcgg ccctcaatcc agcggacctt ccttcccgcg    3720
gcctgctgcc ggctctgcgg cctcttccgc gtcttcgcct tcgccctcag acgagtcgga    3780
tctccctttg ggccgcctcc ccgcctggcg atggtaccgg tgtggaaagt ccccaggctc    3840
cccagcagga gaagtatgc aaagcatgca tctcaattag tcagcaacca ggtgtggaaa    3900
gtccccaggc tccccagcag gcagaagtat gcaaagcatg catctcaatt agtcagcaac    3960
catagtcccg cccctaactc cgcccatccc gcccctaact ccgcccagtt ccgcccattc    4020
tccgccccat ggctgactaa ttttttttat ttatgcagag gccgaggccg cctctgcctc    4080
tgagctattc cagaagtagt gaggaggctt ttttggaggc ctaggctttt gcaaaaagct    4140
cccgggagct tgtatatcca ttttcggatc tgatcagcac gtgcacaatt cgagctcggt    4200
acctttaaga ccaatgactt acaaggcagc tgtagatctt agccacttt taaaagaaaa    4260 gggggggactg aagggctaa ttcactccca acgaagacaa gatctgcttt ttgcttgtac    4320
tgggtctctc tggttagacc agatctgagc ctgggagctc tctggctaac tagggaaccc    4380
```

| actg cttaag cctcaataaa gcttgccttg agtgcttcaa gtagtgtgtg cccgtctgtt | 4440 |
| gtgtgactct ggtaactaga gatccctcag acccttttag tcagtgtgga aaatctctag | 4500 |
| cagtagtagt tcatgtcatc ttattattca gtatttataa cttgcaaaga aatgaatatc | 4560 |
| agagagtgag aggaacttgt ttattgcagc ttataatggt tacaaataaa gcaatagcat | 4620 |
| cacaaatttc acaaataaag cattttttc actgcaccta agg | 4663 |

<210> SEQ ID NO 5
<211> LENGTH: 5611
<212> TYPE: DNA
<213> ORGANISM: Artificial Sequence
<220> FEATURE:
<223> OTHER INFORMATION: Synthetic

<400> SEQUENCE: 5

| gggtctctct ggttagacca gatctgagcc tgggagctct ctggctaact agggaaccca | 60 |
| ctgcttaagc ctcaataaag cttgccttga gtgcttcaag tagtgtgtgc ccgtctgttg | 120 |
| tgtgactctg gtaactagag atccctcaga ccctttagt cagtgtggaa aatctctagc | 180 |
| agtggcgccc gaacagggac ttgaaagcga aagggaaacc agaggagctc tctcgacgca | 240 |
| ggactcggct tgctgaagcg cgcacggcaa gaggcgaggg gcggcgactg gtgagtacgc | 300 |
| caaaaatttt gactagcgga ggctagaagg agagagatgg gtgcgagagc gtcagtatta | 360 |
| agcgggggag aattagatcg cgatgggaaa aaattcggtt aaggccaggg ggaaagaaaa | 420 |
| aatataaatt aaaacatata gtatgggcaa gcagggagct agaacgattc gcagttaatc | 480 |
| ctggcctgtt agaaacatca gaaggctgta gacaaatact gggacagcta caaccatccc | 540 |
| ttcagacagg atcagaagaa cttagatcat tatataatac agtagcaacc ctctattgtg | 600 |
| tgcatcaaag gatagagata aaagacacca aggaagcttt agacaagata gaggaagagc | 660 |
| aaaacaaaag taagaccacc gcacagcaag cggccgctga tcttcagacc tggaggagga | 720 |
| gatatgaggg acaattggag aagtgaatta tataaatata agtagtaaaa aattgaacca | 780 |
| ttaggagtag cacccaccaa ggcaaagaga agagtggtgc agagagaaaa aagagcagtg | 840 |
| ggaataggag ctttgttcct tgggttcttg ggagcagcag gaagcactat gggcgcagcg | 900 |
| tcaatgacgc tgacggtaca ggccagacaa ttattgtctg gtatagtgca gcagcagaac | 960 |
| aatttgctga gggctattga ggcgcaacag catctgttgc aactcacagt ctggggcatc | 1020 |
| aagcagctcc aggcaagaat cctggctgtg gaaagatacc taaaggatca acagctcctg | 1080 |
| gggatttggg gttgctctgg aaaactcatt tgcaccactg ctgtgccttg gaatgctagt | 1140 |
| tggagtaata aatctctgga acagatttgg aatcacacga cctggatgga gtgggacaga | 1200 |
| gaaattaaca attacacaag cttaatacac tccttaattg aagaatcgca aaaccagcaa | 1260 |
| gaaaagaatg aacaagaatt attggaatta gataaatggg caagtttgtg gaattggttt | 1320 |
| aacataacaa attggctgtg gtatataaaa ttattcataa tgatagtagg aggcttggta | 1380 |
| ggtttaagaa tagttttgc tgtactttct atagtgaata gagttaggca gggatattca | 1440 |
| ccattatcgt ttcagaccca cctcccaacc ccgaggggac ccgacaggcc cgaaggaata | 1500 |
| gaagaagaag gtggagagag agacagagac agatccattc gattagtgaa cggatctcga | 1560 |
| cggtatcggt taacttttaa agaaaaggg gggattgggg ggtacagtgc aggggaaaga | 1620 |
| atagtagaca taatagcaac agacatacaa actaaagaat tacaaaaaca aattacaaaa | 1680 |
| attcaaaatt ttatcgataa gcttgggagt tccgcgttac ataacttacg gtaaatggcc | 1740 |
| cgcctggctg accgcccaac gacccccgcc cattgacgtc aataatgacg tatgttccca | 1800 |

```
tagtaacgcc aatagggact ttccattgac gtcaatgggt ggagtattta cggtaaactg    1860
cccacttggc agtacatcaa gtgtatcata tgccaagtac gccccctatt gacgtcaatg    1920
acggtaaatg gcccgcctgg cattatgccc agtacatgac cttatgggac tttcctactt    1980
ggcagtacat ctacgtatta gtcatcgcta ttaccatggt gatgcggttt tggcagtaca    2040
tcaatgggcg tggatagcgg tttgactcac ggggatttcc aagtctccac cccattgacg    2100
tcaatgggag tttgttttgg caccaaaatc aacgggactt tccaaaatgt cgtaacaact    2160
ccgccccatt gacgcaaatg ggcggtaggc gtgtacggtg ggaggtctat ataagcagag    2220
ctcgtttagt gaaccgtcag atcgcctgga cgccatcc acgctgtttt gacctccata    2280
gaagacaccg actctagagg atccactagt ccagtgtggt ggaattctgc agatatcaac    2340
aagtttgtac aaaaaagcag gctccaccat ggaagacgcc aaaaacataa agaaaggccc    2400
ggcgccattc tatcctctag aggatggaac cgctggagag caactgcata aggctatgaa    2460
gagatacgcc ctggttcctg gaacaattgc ttttacagat gcacatatcg aggtgaacat    2520
cacgtacgcg gaatacttcg aaatgtccgt tcggttggca aagctatga acgatatgg    2580 gctgaataca aatcacagaa tcgtcgtatg cagtgaaaac tctcttcaat tctttatgcc    2640
ggtgttgggc gcgttattta tcggagttgc agttgcgccc gcgaacgaca tttataatga    2700
acgtgaattg ctcaacagta tgaacatttc gcagcctacc gtagtgtttg tttccaaaaa    2760
ggggttgcaa aaatttttga acgtgcaaaa aaattacca ataattcaga aaattattat    2820
catggattct aaaacggatt accagggatt tcagtcgatg tacacgttcg tcacatctca    2880
tctacctccc ggttttaatg agtacgattt tgtaccagag tcctttgatc gtgacaaaac    2940
aattgcactg ataatgaatt cctctggatc tactgggtta cctaagggtg tggcccttcc    3000
gcatagaact gcctgcgtca gattctcgca tgccagagat cctattttg gcaatcaaat    3060 cattccggat actgcgattt taagtgttgt tccattccat cacggttttg gaatgtttac    3120
tacactcgga tatttgatat gtggatttcg agtcgtctta atgtatagat ttgaagaaga    3180 gctgtttta cgatcccttc aggattacaa aattcaaagt gcgttgctag taccaaccct    3240
attttcattc ttcgccaaaa gcactctgat tgacaaatac gatttatcta atttacacga    3300
aattgcttct gggggcgcac ctctttcgaa agaagtcggg gaagcggttg caaaacgctt    3360
ccatcttcca gggatacgac aaggatatgg gctcactgag actacatcag ctattctgat    3420
tacacccgag ggggatgata aaccgggcgc ggtcggtaaa gttgttccat tttttgaagc    3480
gaaggttgtg gatctggata ccgggaaaac gctgggcgtt aatcagagag gcgaattatg    3540
tgtcagagga cctatgatta tgtccggtta tgtaaacaat ccggaagcga ccaacgcctt    3600
gattgacaag gatggatggc tacattctgg agacatagct tactgggacg aagacgaaca    3660
cttcttcata gttgaccgct tgaagtcttt aattaaatac aaaggatatc aggtggcccc    3720
cgctgaattg gaatcgatat tgttacaaca ccccaacatc ttcgacgcgg gcgtggcagg    3780
tcttcccgac gatgacgccg gtgaacttcc cgccgccgtt gttgttttgg agcacggaaa    3840
gacgatgacg gaaaaagaga tcgtggatta cgtcgccagt caagtaacaa ccgcgaaaaa    3900
gttgcgcgga ggagttgtgt tgtggacga agtaccgaaa ggtcttaccg gaaaactcga    3960
cgcaagaaaa atcagagaga tcctcataaa ggccaagaag ggcggaaagt ccaaattgta    4020
aacccagctt tcttgtacaa agtggttgat atccagcaca gtggcggccg ctcgagtcta    4080
gagggcccgc ggttcgaagg taagcctatc cctaacccTc tcctcggtct cgattctacg    4140
```

```
cgtaccggtt agtaatgatc gacaatcaac ctctggatta caaaatttgt gaaagattga      4200
ctggtattct taactatgtt gctcctttta cgctatgtgg atacgctgct ttaatgcctt      4260
tgtatcatgc tattgcttcc cgtatggctt tcattttctc ctccttgtat aaatcctggt      4320
tgctgtctct ttatgaggag ttgtggcccg ttgtcaggca acgtggcgtg gtgtgcactg      4380
tgtttgctga cgcaaccccc actggttggg gcattgccac cacctgtcag ctcctttccg      4440
ggactttcgc tttccccctc cctattgcca cggcggaact catcgccgcc tgccttgccc      4500
gctgctggac aggggctcgg ctgttgggca ctgacaattc cgtggtgttg tcggggaagc      4560
tgacgtcctt tccatggctg ctcgcctgtg ttgccacctg gattctgcgc gggacgtcct      4620
tctgctacgt cccttcggcc ctcaatccag cggaccttcc ttcccgcggc ctgctgccgg      4680
ctctgcggcc tcttccgcgt cttcgccttc gccctcagac gagtcggatc tccctttggg      4740
ccgcctcccc gcctggcgat ggtaccggtg tggaaagtcc ccaggctccc cagcaggcag      4800
aagtatgcaa agcatgcatc tcaattagtc agcaaccagg tgtggaaagt ccccaggctc      4860
cccagcaggc agaagtatgc aaagcatgca tctcaattag tcagcaacca tagtcccgcc      4920
cctaactccg cccatcccgc ccctaactcc gcccagttcc gcccattctc cgccccatgg      4980
ctgactaatt ttttttattt atgcagaggc cgaggccgcc tctgcctctg agctattcca      5040
gaagtagtga ggaggctttt ttggaggcct aggcttttgc aaaaagctcc cgggagcttg      5100
tatatccatt ttcggatctg atcagcacgt gcacaattcg agctcggtac ctttaagacc      5160
aatgacttac aaggcagctg tagatcttag ccacttttta aaagaaaagg ggggactgga      5220
agggctaatt cactcccaac gaagacaaga tctgcttttt gcttgtactg ggtctctctg      5280
gttagaccag atctgagcct gggagctctc tggctaacta gggaacccac tgcttaagcc      5340
tcaataaagc ttgccttgag tgcttcaagt agtgtgtgcc cgtctgttgt gtgactctgg      5400
taactagaga tccctcagac cctttagtc agtgtggaaa atctctagca gtagtagttc       5460
atgtcatctt attattcagt atttataact tgcaaagaaa tgaatatcag agagtgagag      5520
gaacttgttt attgcagctt ataatggtta caaataaagc aatagcatca caaatttcac      5580
aaataaagca tttttttcac tgcacctaag g                                     5611

<210> SEQ ID NO 6
<211> LENGTH: 6770
<212> TYPE: DNA
<213> ORGANISM: Artificial Sequence
<220> FEATURE:
<223> OTHER INFORMATION: Synthetic

<400> SEQUENCE: 6
agaccaggaa ttacatttgc ttctgacaca actgtgttca ctagcaacct caaacagagc        60
cgccatgggt gcgagagcgt cagtattaag cgggggagaa ttagatcgat gggaaaaaat       120
tcggttaagg ccaggggaa agaaaaaata taaattaaaa catatagtat gggcaagcag       180
ggagctagaa cgattcgcag ttaatcctgg cctgttagaa acatcagaag gctgtagaca       240
aatactggga cagctacaac catcccttca gacaggatca aagaacttaa gatcattata       300
taatacagta gcaaccctct attgtgtgca tcaaaggata gagataaaag acaccaagga       360
agctttagac aagatagagg aagagcaaaa caaaagtaag aaaaaagcac agcaagcagc       420
agctgacaca ggacacagca atcaggtcag ccaaaattac cctatagtgc agaacatcca       480
ggggcaaatg gtacatcagg ccatatcacc tagaacttta aatgcatggg taaaagtagt       540
agaagagaag gctttcagcc cagaagtgat acccatgttt tcagcattat cagaaggagc       600
```

```
caccccacaa gatttaaaca ccatgctaaa cacagtgggg ggacatcaag cagccatgca      660
aatgttaaaa gagaccatca atgaggaagc tgcagaatgg gatagagtgc atccagtgca      720
tgcagggcct attgcaccag gccagatgag agaaccaagg ggaagtgaca tagcaggaac      780
tactagtacc cttcaggaac aaataggatg gatgacacat aatccaccta tcccagtagg      840
agaaatctat aaaagatgga taatcctggg attaaataaa atagtaagaa tgtatagccc      900
taccagcatt ctggacataa gacaaggacc aaaggaaccc tttagagact atgtagaccg      960
attctataaa actctaagag ccgagcaagc ttcacaagag gtaaaaaatt ggatgacaga     1020
aaccttgttg gtccaaaatg cgaacccaga ttgtaagact attttaaaag cattgggacc     1080
aggagcgaca ctagaagaaa tgatgacagc atgtcaggga gtgggggggac ccggccataa   1140 agcaagagtt ttggctgaag caatgagcca agtaacaaat ccagctacca taatgataca     1200
gaaaggcaat tttaggaacc aaagaaagac tgttaagtgt ttcaattgtg gcaaagaagg     1260
gcacatagcc aaaaattgca gggcccctag gaaaaagggc tgttggaaat gtggaaagga     1320
aggacaccaa atgaaagatt gtactgagag acaggctaat ttttaggga agatctggcc      1380 ttcccacaag ggaaggccag ggaattttct tcagagcaga ccagagccaa cagccccacc     1440
agaagagagc ttcaggtttg gggaagagac aacaactccc tctcagaagc aggagccgat     1500
agacaaggaa ctgtatcctt tagcttccct cagatcactc tttggcagcg acccctcgtc     1560
acaataaaga taggggggca attaaaggaa gctctattag atacaggagc agatgataca     1620
gtattagaag aaatgaattt gccaggaaga tggaaaccaa aaatgatagg gggaattgga     1680
ggttttatca aagtaagaca gtatgatcag atactcatag aaatctgcgg acataaagct     1740
ataggtacag tattagtagg acctacacct gtcaacataa ttggaagaaa tctgttgact     1800
cagattggct gcactttaaa ttttcccatt agtcctattg agactgtacc agtaaaatta     1860
aagccaggaa tggatggccc aaaagttaaa caatggccat tgacagaaga aaaaataaaa     1920
gcattagtag aaatttgtac agaaatggaa aaggaaggaa aaatttcaaa aattgggcct     1980
gaaaatccat acaatactcc agtatttgcc ataaagaaaa aagacagtac taaatggaga     2040
aaattagtag atttcagaga acttaataag agaactcaag atttctggga agttcaatta     2100
ggaataccac atcctgcagg gttaaaacag aaaaaatcag taacagtact ggatgtgggc     2160
gatgcatatt tttcagttcc cttagataaa gacttcagga agtatactgc atttaccata     2220
cctagtataa acaatgagac accagggatt agatatcagt acaatgtgct tccacaggga     2280
tggaaaggat caccagcaat attccagtgt agcatgacaa aaatcttaga gccttttaga     2340
aaacaaaatc cagacatagt catctatcaa tacatggatg atttgtatgt aggatctgac     2400
ttagaaatag ggcagcatag aacaaaaata gaggaactga gacaacatct gttgaggtgg     2460
ggatttacca caccagacaa aaaacatcag aaagaacctc cattcctttg gatgggttat     2520
gaactccatc ctgataaatg gacagtacag cctatagtgc tgccagaaaa ggacagctgg     2580
actgtcaatg acatacagaa attagtggga aaattgaatt gggcaagtca gatttatgca     2640
gggattaaag taaggcaatt atgtaaactt cttaggggaa ccaaagcact aacagaagta     2700
gtaccactaa cagaagaagc agagctagaa ctggcagaaa acagggagat tctaaaagaa     2760
ccggtacatg gagtgtatta tgacccatca aaagacttaa tagcagaaat acagaagcag     2820
gggcaaggcc aatggacata tcaaatttat caagagccat ttaaaaatct gaaaacagga     2880
aagtatgcaa gaatgaaggg tgcccacact aatgatgtga acaattaac agaggcagta     2940
```

```
caaaaaatag ccacagaaag catagtaata tggggaaaga ctcctaaatt taaattaccc    3000
atacaaaagg aaacatggga agcatggtgg acagagtatt ggcaagccac ctggattcct    3060
gagtgggagt ttgtcaatac ccctccctta gtgaagttat ggtaccagtt agagaaagaa    3120
cccataatag gagcagaaac tttctatgta gatggggcag ccaataggga aactaaatta    3180
ggaaaagcag gatatgtaac tgacagagga agacaaaaag ttgtccccct aacggacaca    3240
acaaatcaga agactgagtt acaagcaatt catctagctt tgcaggattc gggattagaa    3300
gtaaacatag tgacagactc acaatatgca ttgggaatca ttcaagcaca accagataag    3360
agtgaatcag agttagtcag tcaaataata gagcagttaa taaaaaagga aaaagtctac    3420
ctggcatggg taccagcaca caaaggaatt ggaggaaatg aacaagtaga taaattggtc    3480
agtgctggaa tcaggaaagt actattttta gatggaatag ataaggccca agaagaacat    3540
gagaaatatc acagtaattg gagagcaatg gctagtgatt ttaacctacc acctgtagta    3600
gcaaagaaaa tagtagccag ctgtgataaa tgtcagctaa aaggggaagc catgcatgga    3660
caagtagact gtagcccagg aatatggcag ctagattgta cacatttaga aggaaaagtt    3720
atcttggtag cagttcatgt agccagtgga tatatagaag cagaagtaat tccagcagag    3780
acagggcaag aaacagcata cttcctctta aaattagcag gaagatggcc agtaaaaaca    3840
gtacatacag acaatggcag caatttcacc agtactacag ttaaggccgc ctgttggtgg    3900
gcggggatca gcaggaatt tggcattccc tacaatcccc aaagtcaagg agtaatagaa    3960
tctatgaata aagaattaaa gaaaattata ggacaggtaa gagatcaggc tgaacatctt    4020
aagacagcag tacaaatggc agtattcatc cacaatttta aaagaaaagg ggggattggg    4080
gggtacagtg caggggaaag aatagtagac ataatagcaa cagacataca aactaaagaa    4140
ttacaaaaac aaattacaaa aattcaaaat tttcgggttt attacaggga cagcagagat    4200
ccagtttgga aaggaccagc aaagctcctc tggaaaggtg aaggggcagt agtaatacaa    4260
gataatagtg acataaaagt agtgccaaga agaaaagcaa agatcatcag ggattatgga    4320
aaacagatgg caggtgatga ttgtgtggca agtagacagg atgaggatta agctcgctt    4380 tcttgctgtc caatttctat taaaggttcc tttgttccct aagtccaact actaaactgg    4440
gggatattat gaagggcctt gagcatctgg attctgccta ataagaaaca tttattgtca    4500
ttgcagagac gcggccgcgc gtctcaatga agagcgtcga cgcatgcgga ggctaggtgg    4560
aggctcagtg atgataagtc tgcgatggtg gatgcatgtg tcatggtcat agctgtttcc    4620
tgtgtgaaat tgttatccgc tcagagggca caatcctatt ccgcgctatc cgacaatctc    4680
caagacatta ggtggagttc agttcggcgt atggcatatg tcgctggaaa gaacatgtga    4740
gcaaaaggcc agcaaaaggc caggaaccgt aaaaaggccg cgttgctggc gtttttccat    4800
aggctccgcc cccctgacga gcatcacaaa aatcgacgct caagtcagag gtggcgaaac    4860
ccgacaggac tataaagata ccaggcgttt ccccctggaa gctccctcgt gcgctctcct    4920
gttccgaccc tgccgcttac cggatacctg tccgcctttc tcccttcggg aagcgtggcg    4980
ctttctcata gctcacgctg taggtatctc agttcggtgt aggtcgttcg ctccaagctg    5040
ggctgtgtgc acgaaccccc cgttcagccc gaccgctgcg ccttatccgg taactatcgt    5100
cttgagtcca acccggtaag acacgactta tcgccactgg cagcagccac tggtaacagg    5160
attagcagag cgaggtatgt aggcggtgct acagagttct tgaagtggtg gcctaactac    5220
ggctacacta gaagaacagt atttggtatc tgcgctctgc tgaagccagt taccttcgga    5280
aaaagagttg gtagctcttg atccggcaaa caaaccaccg ctggtagcgg tggtttttt    5340
```

```
gtttgcaagc agcagattac gcgcagaaaa aaaggatctc aagaagatcc tttgatcttt    5400
tctacggggt ctgacgctct attcaacaaa gccgccgtcc cgtcaagtca gcgtaaatgg    5460 gtaggggggct tcaaatcgtc ctcgtgatac caattcggag cctgcttttt tgtacaaact    5520
tgttgataat ggcaattcaa ggatcttcac ctagatcctt ttaaattaaa aatgaagttt    5580
taaatcaatc taaagtatat atgagtaaac ttggtctgac agttaccaat gcttaatcag    5640
tgaggcacct atctcagcga tctgtctatt tcgttcatcc atagttgcct gactcccgt     5700 cgtgtagata actacgatac gggagggctt accatctggc cccagtgctg caatgatacc    5760
gcgagagcca cgctcaccgg ctccagattt atcagcaata accagccag ccggaagggc     5820 cgagcgcaga gtggtcctg caactttatc cgcctccatc cagtctatta attgttgccg     5880
ggaagctaga gtaagtagtt cgccagttaa tagtttgcgc aacgttgttg ccattgctac    5940
aggcatcgtg gtgtcacgct cgtcgtttgg tatggcttca ttcagctccg gttcccaacg    6000
atcaaggcga gttacatgat cccccatgtt gtgcaaaaaa gcggttagct ccttcggtcc    6060
tccgatcgtt gtcagaagta agttggccgc agtgttatca ctcatggtta tggcagcact    6120
gcataattct cttactgtca tgccatccgt aagatgcttt tctgtgactg gtgagtactc    6180
aaccaagtca ttctgagaat agtgtatgcg gcgaccgagt tgctcttgcc cggcgtcaat    6240
acgggataat accgcgccac atagcagaac tttaaaagtg ctcatcattg gaaaacgttc    6300
ttcggggcga aaactctcaa ggatcttacc gctgttgaga tccagttcga tgtaacccac    6360
tcgtgcaccc aactgatctt cagcatcttt tactttcacc agcgtttctg gtgagcaaa    6420 aacaggaagg caaaatgccg caaaaaaggg aataagggcg acacggaaat gttgaatact    6480
catactcttc cttttcaat attattgaag catttatcag ggttattgtc tcatgagcgg     6540
atacatattt gaatgtattt agaaaaataa acaaataggg gttccgcgca catttccccg    6600
aaaagtgcca gatacctgaa acaaaaccca tcgtacggcc aaggaagtct ccaataactg    6660
tgatccacca caagcgccag ggttttccca gtcacgacgt tgtaaaacga cggccagtca    6720
tgcataatcc gcacgcatct ggaataagga agtgccattc cgcctgacct                6770
```

<210> SEQ ID NO 7
<211> LENGTH: 1700
<212> TYPE: DNA
<213> ORGANISM: Artificial Sequence
<220> FEATURE:
<223> OTHER INFORMATION: Synthetic

<400> SEQUENCE: 7

```
agaccaggaa ttacatttgc ttctgacaca actgtgttca ctagcaacct caaacagagc      60
cgccatgggt gcgagagcgt cagtattaag cgggggagaa ttagatcgat gggaaaaaat     120
tcggttaagg ccaggggaa agaaaaaata taattaaaa catatagtat gggcaagcag       180
ggagctagaa cgattcgcag ttaatcctgg cctgttagaa acatcagaag gctgtagaca     240
aatactggga cagctacaac catcccttca gacaggatca gaagaactta gatcattata     300
taatacagta gcaaccctct attgtgtgca tcaaaggata gagataaaag acaccaagga     360
agctttagac aagatagagg aagagcaaaa caaagtaag aaaaaagcac agcaagcagc      420
agctgacaca ggacacagca atcaggtcag ccaaaattac cctatagtgc agaacatcca     480
ggggcaaatg gtacatcagg ccatatcacc tagaacttta aatgcatggg taaaagtagt     540
agaagagaag gctttcagcc cagaagtgat acccatgttt tcagcattat cagaaggagc     600
```

```
caccccacaa gatttaaaca ccatgctaaa cacagtgggg ggacatcaag cagccatgca      660
aatgttaaaa gagaccatca atgaggaagc tgcagaatgg gatagagtgc atccagtgca      720
tgcagggcct attgcaccag gccagatgag agaaccaagg ggaagtgaca tagcaggaac      780
tactagtacc cttcaggaac aaataggatg gatgacacat aatccaccta tcccagtagg      840
agaaatctat aaaagatgga taatcctggg attaaataaa atagtaagaa tgtatagccc      900
taccagcatt ctggacataa gacaaggacc aaaggaaccc tttagagact atgtagaccg      960
attctataaa actctaagag ccgagcaagc ttcacaagag gtaaaaaatt ggatgacaga     1020
aaccttgttg gtccaaaatg cgaacccaga ttgtaagact attttaaaag cattgggacc     1080
aggagcgaca ctagaagaaa tgatgacagc atgtcaggga gtggggggac ccggccataa     1140
agcaagagtt ttggctgaag caatgagcca agtaacaaat ccagctacca taatgataca     1200
gaaaggcaat tttaggaacc aaagaaagac tgttaagtgt ttcaattgtg gcaaagaagg     1260
gcacatagcc aaaaattgca gggcccctag gaaaaagggc tgttggaaat gtggaaagga     1320
aggacaccaa atgaaagatt gtactgagag acaggctaat tttttaggga agatctggcc     1380
ttcccacaag ggaaggccag ggaattttct tcagagcaga ccagagccaa cagccccacc     1440
agaagagagc ttcaggtttg gggaagagac aacaactccc tctcagaagc aggagccgat     1500
agacaaggaa ctgtatcctt tagcttccct cagatcactc tttggcagcg acccctcgtc     1560
acaataaagc tcgctttctt gctgtccaat ttctattaaa ggttcctttg ttccctaagt     1620
ccaactacta aactggggga tattatgaag ggccttgagc atctggattc tgcctaataa     1680
gaaacattta ttgtcattgc                                                 1700
```

<210> SEQ ID NO 8
<211> LENGTH: 1619
<212> TYPE: DNA
<213> ORGANISM: Artificial Sequence
<220> FEATURE:
<223> OTHER INFORMATION: Synthetic

<400> SEQUENCE: 8

```
agaccaggaa ttacatttgc ttctgacaca actgtgttca ctagcaacct caaacagagc       60
cgccatggga ttccttgacg gcatcgacaa ggcgcaagag gagcacgaga aatatcatag      120
caactggagg gcgatggcat cagacttcaa cttgccgcca gtcgtggcta agagatagt       180 agcaagctgc gataagtgtc aactgaaggg tgaagcgatg cacggtcaag tggactgttc      240
ccctggtata tggcaactgg actgtaccca tctcgaaggt aaagtcattt tggttgctgt      300
acatgttgcc tctgggtata tcgaggctga ggtgattcca gcagaaacgg gacaggaaac      360
agcttatttc ttgctcaagc ttgccggag atggcctgtg aaaactgttc atacagataa      420
tggtagcaat tttactagta cgaccgtgaa agcagcttgt tggtgggcag ggattaagca      480
agaattcgga atcccgtata acccgcagag tcagggcgtt attgagagca tgaacaagga      540
actgaaaaaa ataattgggc aagtgagaga tcaggctgag catcttaaaa ctgctgtaca      600
aatggcggtg ttcatacata attttaagcg gaagggagga attggaggat actctgcggg      660
agagaggata gtggatataa tagcgaccga tattcagaca aaggagctgc aaaaacagat      720
aacgaaaata caaaattttc gagtttacta tcgggactcc cgcgatcccg tgtggaaagg      780
tccagcgaaa ttgctttgga agggcgaagg cgcggtagtg atccaggaca attctgatat      840
caaagtggtc ccaaggcgga aagcaaagat aatccgcgac tacggcaagc aaatggcagg      900
agatgattgc gtcgcatcac gacaggacga agatggcggc ggcggctcca tggccctgac      960
```

```
caacgcccag atcctggccg tgatcgacag ctgggaggaa accgtgggcc agttccccgt    1020
gatcacccac catgtgcctc tgggcggagg cctccaggga accctgcact gttacgagat    1080
ccccctggcc gctccttacg gcgtgggctt tgccaagaac ggccccacca gatggcagta    1140
caagcggacc atcaaccagg tggtgcacag atggggcagc cacaccgtgc cctttctgct    1200
ggaacccgac aacatcaacg gcaagacctg caccgccagc cacctgtgcc acaacaccag    1260
atgccacaac cccctgcacc tgtgctggga gagcctggac gacgccaagg gccggaattg    1320
gtgccctggc cctaatggcg gatgtgtgca tgccgtcgtg tgcctgagac agggacctct    1380
gtatggccct ggcgctacag tggctggccc tcagcagagg ggctcccact cgtggtgta     1440 aagctcgctt tcttgctgtc caatttctat taaaggttcc tttgttccct aagtccaact    1500
actaaactgg gggatattat gaagggcctt gagcatctgg attctgccta ataagaaaca    1560
tttattgtca ttgcagagac gcggccgcgc gtctcaatga gagcgtcga cgcatgcgg     1619
```

<210> SEQ ID NO 9
<211> LENGTH: 3764
<212> TYPE: DNA
<213> ORGANISM: Artificial Sequence
<220> FEATURE:
<223> OTHER INFORMATION: Synthetic

<400> SEQUENCE: 9

```
agaccaggaa ttacatttgc ttctgacaca actgtgttca ctagcaacct caaacagagc     60
cgccatgggc ttttttaggg aagatctggc cttcccacaa gggaaggcca gggaattttc    120
ttcagagcag accagagcca acagccccac cagaagagag cttcaggttt ggggaagaga    180
caacaactcc ctctcagaag caggagccga tagacaagga actgtatcct ttagcttccc    240
tcagatcact ctttggcagc gaccectcgt cacaataaag atagggggc agctcaagga    300 ggctctcctg gacaccggag cagacgcacc cgtgctggag gagatgtcgt tgccaggccg    360
ctggaagccg aagatgatcg ggggaatcgg cggtttcatc aaggtgcgcc agtatgacca    420
gatcctcatc gaaatctgcg gccacaaggc tatcggtacc gtgctggtgg gccccacacc    480
cgtcaacatc atcggacgca acctgttgac gcagatcggt tgcacgctga acttcccat     540 tagccctatc gagacggtac cggtgaagct gaagcccggg atggacggcc cgaaggtcaa    600
gcaatggcca ttgacagagg agaagatcaa ggcactggtg gagatttgca cagagatgga    660
aaaggaaggg aaaatctcca agattgggcc tgagaacccg tacaacacgc cggtgttcgc    720
aatcaagaag aaggactcga cgaaatggcg caagctggtg gacttccgcg agctgaacaa    780
gcgcacgcaa gacttctggg aggttcagct gggcatcccg caccccgcag ggctgaagaa    840
gaagaaatcc gtgaccgtac tggatgtggg tgatgcctac ttctccgttc cctggacga    900 agacttcagg aagtacactg ccttcacaat cccttcgatc aacaacgaga caccggggat    960
tcgatatcag tacaacgtgc tgccccaggg ctggaaaggc ctcccgcaa tcttccagag   1020 tagcatgacc aaaatcctgg agcctttccg caaacagaac cccgacatcg tcatctatca   1080
gtacatggat gacttgtacg tgggctctga tctagagata gggcagcacc gcaccaagat   1140
cgaggagctg cgccagcacc tgttgaggtg gggactgacc acacccgaca agaagcacca   1200
gaaggagcct cccttcctct ggatgggtta cgagctgcac cctgacaaat ggaccgtgca   1260
gcctatcgtg ctgccagaga aagacagctg gactgtcaac gacatacaga gctggtggg    1320 gaagttgaac tgggccagtc agatttaccc agggattaag gtgaggcagc tgtgcaaact   1380
```

```
cctccgcgga accaaggcac tcacagaggt gatccccta accgaggagg ccgagctcga   1440
actggcagaa aaccgagaga tcctaaagga gcccgtgcac ggcgtgtact atgacccctc   1500
caaggacctg atcgccgaga tccagaagca ggggcaaggc cagtggacct atcagattta   1560
ccaggagccc ttcaagaacc tgaagaccgg caagtacgcc cggatgaggg gtgcccacac   1620
taacgacgtc aagcagctga ccgaggccgt gcagaagatc accaccgaaa gcatcgtgat   1680
ctggggaaag actcctaagt tcaagctgcc catccagaag gaaacctggg aaacctggtg   1740
gacagagtat tggcaggcca cctggattcc tgagtgggag ttcgtcaaca cccctcccct   1800
ggtgaagctg tggtaccagc tggagaagga gcccatagtg ggcgccgaaa ccttctacgt   1860
ggatggggcc gctaacaggg agactaagct gggcaaagcc ggatacgtca ctaaccgggg   1920
cagacagaag gttgtcaccc tcactgacac caccaaccag aagactgagc tgcaggccat   1980
ttacctcgct ttgcaggact cgggcctgga ggtgaacatc gtgacagact ctcagtatgc   2040
cctgggcatc attaagccc agccagacca gagtgagtcc gagctggtca atcagatcat   2100
cgagcagctg atcaagaagg aaaaggtcta tctggcctgg gtacccgccc acaaaggcat   2160
tggcggcaat gagcaggtcg acaagctggt ctcggctggc atcaggaagg tgctattcct   2220
ggatggcatc gacaaggccc aggacgagca cgagaaatac cacagcaact ggcgggccat   2280
ggctagcgac ttcaacctgc cccctgtggt ggccaaagag atcgtggcca gctgtgacaa   2340
gtgtcagctc aagggcgaag ccatgcatgg ccaggtggac tgtagcccg gcatctggca   2400
actcgattgc acccatctgg agggcaaggt tatcctggta gccgtccatg tggccagtgg   2460
ctacatcgag gccgaggtca ttcccgccga acagggcag gagacagcct acttcctcct   2520
gaagctggca ggccggtggc cagtgaagac catccatact gacaatggca gcaatttcac   2580
cagtgctacg gttaaggccg cctgctggtg ggcgggaatc aagcaggagt tcgggatccc   2640
ctacaatccc cagagtcagg gcgtcgtcga gtctatgaat aaggagttaa agaagattat   2700
cggccaggtc agagatcagg ctgagcatct caagaccgcg gtccaaatgg cggtattcat   2760
ccacaatttc aagcggaagg gggggattgg ggggtacagt gcggggggagc ggatcgtgga   2820
catcatcgcg accgacatcc agactaagga gctgcaaaag cagattacca agattcagaa   2880
tttccgggtc tactacaggg acagcagaaa tcccctctgg aaaggcccag cgaagctcct   2940
ctggaagggt gagggggcag tagtgatcca ggataatagc gacatcaagg tggtgcccag   3000
aagaaaggcg aagatcatta gggattatgg caaacagatg gcgggtgatg attgcgtggc   3060
gagcagacag gatgaggatg gcggcggcgg ctccatggcc ctgaccaacg cccagatcct   3120
ggccgtgatc gacagctggg aggaaaccgt gggccagttc cccgtgatca cccaccatgt   3180
gcctctgggc ggaggcctcc agggaaccct gcactgttac gagatccccc tggccgctcc   3240
ttacggcgtg ggctttgcca agaacggccc caccagatgg cagtacaagc ggaccatcaa   3300
ccaggtggtg cacagatggg gcagccacac cgtgcccttt ctgctggaac ccgacaacat   3360
caacggcaag acctgcaccg ccagccacct gtgccacaac accagatgcc acaaccccct   3420
gcacctgtgc tgggagagcc tggacgacgc caagggccgg aattggtgcc ctggccctaa   3480
tggcggatgt gtgcatgccg tcgtgtgcct gagacaggga cctctgtatg cccctggcgc   3540
tacagtggct ggccctcagc agagggggctc ccacttcgtg gtgtaaagct cgcttttcttg   3600
ctgtccaatt tctattaaag gttcctttgt tccctaagtc caactactaa actgggggat   3660
attatgaagg gccttgagca tctggattct gcctaataag aaacatttat tgtcattgca   3720
gagacgcggc cgcgcgtctc aatgaagagc gtcgacgcat gcgg              3764
```

<210> SEQ ID NO 10
<211> LENGTH: 4474
<212> TYPE: DNA
<213> ORGANISM: Artificial Sequence
<220> FEATURE:
<223> OTHER INFORMATION: Synthetic

<400> SEQUENCE: 10

```
gggtctctct ggttagacca gatctgagcc tgggagctct ctggctaact agggaaccca      60
ctgcttaagc ctcaataaag cttgccttga gtgcttcaag tagtgtgtgc ccgtctgttg     120
tgtgactctg gtaactagag atccctcaga ccctttagt cagtgtggaa aatctctagc      180
agtggcgccc gaacagggac ttgaaagcga agggaaacc agaggagctc tctcgacgca      240
ggactcggct tgctgaagcg cgcacggcaa gaggcgaggg gcggcgactg gtgagtacgc     300
caaaatttt gactagcgga ggctagaagg agagagatgg gtgcgagagc gtcagtatta     360
agcggggag aattagatcg cgatgggaaa aaattcggtt aaggccaggg ggaaagaaaa      420
aatataaatt aaaacatata gtatgggcaa gcagggagct agaacgattc gcagttaatc     480
ctggcctgtt agaaacatca gaaggctgta gacaaatact gggacagcta caaccatccc     540
ttcagacagg atcagaagaa cttagatcat tatataatac agtagcaacc ctctattgtg     600
tgcatcaaag gatagagata aaagacacca aggaagcttt agacaagata gaggaagagc     660
aaaacaaaag taagaccacc gcacagcaag cggccgctga tcttcagacc tggaggagga     720
gatatgaggg acaattggag aagtgaatta tataaatata agtagtaaaa attgaaccca     780
ttaggagtag caccccaccaa ggcaaagaga agagtggtgc agagagaaaa aagagcagtg     840
ggaataggag cttgttcct tgggttcttg ggagcagcag gaagcactat gggcgcagcg     900
tcaatgacgc tgacggtaca ggccagacaa ttattgtctg gtatagtgca gcagcagaac     960
aatttgctga gggctattga ggcgcaacag catctgttgc aactcacagt ctggggcatc    1020
aagcagctcc aggcaagaat cctggctgtg gaaagatacc taaaggatca acagctcctg    1080
gggatttggg gttgctctgg aaaactcatt tgcaccactg ctgtgccttg gaatgctagt    1140
tggagtaata aatctctgga acagatttgg aatcacacga cctggatgga gtgggacaga    1200
gaaattaaca attacacaag cttaatacac tccttaattg aagaatcgca aaaccagcaa    1260
gaaaagaatg aacaagaatt attggaatta gataaatggg caagtttgtg gaattggttt    1320
aacataacaa attggctgtg gtatataaaa ttattcataa tgatagtagg aggcttggta    1380
ggtttaagaa tagttttgc tgtactttct atagtgaata gagttaggca gggatattca    1440
ccattatcgt ttcagaccca cctcccaacc ccgagggac ccgacaggcc cgaaggaata    1500
gaagaagaag gtggagagag agacagagac agatccattc gattagtgaa cggatctcga    1560
cggtatcggt taacttttaa aagaaaaggg gggattgggg ggtacagtgc aggggaaaga    1620
atagtagaca taatagcaac agacatacaa actaaagaat acaaaaaaca aattacaaaa    1680
attcaaaatt ttatcgataa gcttgggagt tccgcgttac ataacttacg gtaaatggcc    1740
cgcctggctg accgcccaac gacccccgcc cattgacgtc aataatgacg tatgttccca    1800
tagtaacgcc aatagggact ttccattgac gtcaatgggt ggagtattta cggtaaactg    1860
cccacttggc agtacatcaa gtgtatcata tgccaagtac gccccctatt gacgtcaatg    1920
acggtaaatg gcccgcctgg cattatgccc agtacgatgac cttatgggac ttcctacttt    1980
ggcagtacat ctacgtatta gtcatcgcta ttaccatggt gatgcggttt tggcagtaca   2040
```

```
tcaatgggcg tggatagcgg tttgactcac ggggatttcc aagtctccac cccattgacg   2100
tcaatgggag tttgttttgg caccaaaatc aacgggactt tccaaaatgt cgtaacaact   2160 ccgcccatt  gacgcaaatg gcggtaggc  gtgtacggtg ggaggtctat ataagcagag   2220
ctcgtttagt gaaccgtcag atcgcctgga gacgccatcc acgctgtttt gacctccata   2280
gaagacaccg actctagagg atccactagt ccagtgtggt ggaattctgc agatatcaac   2340
aagtttgtac aaaaaagcag gctccaccat ggtcttcaca ctcgaagatt tcgttgggga   2400
ctggcgacag acagccggct acaacctgga ccaagtcctt gaacagggag gtgtgtccag   2460 tttgttcag  aatctcgggg tgtccgtaac tccgatccaa aggattgtcc tgagcggtga   2520
aaatgggctg aagatcgaca tccatgtcat catcccgtat gaaggtctga gcggcgacca   2580
aatgggccag atcgaaaaaa ttttttaaggt ggtgtaccct gtggatgatc atcactttaa   2640
ggtgatcctg cactatggca cactggtaat cgacggggtt acgccgaaca tgatcgacta   2700
tttcggacgg ccgtatgaag gcatcgccgt gttcgacggc aaaaagatca ctgtaacagg   2760
gaccctgtgg aacggcaaca aaattatcga cgagcgcctg atcaacccg  acggctccct   2820 gctgttccga gtaaccatca acggagtgac cggctggcgg ctgtgcgaac gcattctggc   2880
gtaaacccag ctttcttgta caaagtggtt gatatccagc acagtggcgg ccgctcgagt   2940
ctagagggcc cgcggttcga aggtaagcct atccctaacc ctctcctcgg tctcgattct   3000
acgcgtaccg gttagtaatg atcgacaatc aacctctgga ttacaaaatt tgtgaaagat   3060
tgactggtat tcttaactat gttgctcctt ttacgctatg tggatacgct gctttaatgc   3120
ctttgtatca tgctattgct tcccgtatgg ctttcatttt ctcctccttg tataaatcct   3180
ggttgctgtc tctttatgag gagttgtggc ccgttgtcag gcaacgtggc gtggtgtgca   3240
ctgtgtttgc tgacgcaacc cccactggtt ggggcattgc caccacctgt cagctccttt   3300
ccgggacttt cgctttcccc ctccctattg ccacggcgga actcatcgcc gcctgccttg   3360
cccgctgctg gacaggggct cggctgttgg cactgacaa  ttccgtggtg ttgtcgggga   3420
agctgacgtc ctttccatgg ctgctcgcct gtgttgccac ctggattctg cgcgggacgt   3480
ccttctgcta cgtcccttcg gccctcaatc cagcggacct tccttcccgc ggcctgctgc   3540
cggctctgcg gcctcttccg cgtcttcgcc ttcgccctca gacgagtcgg atctcccttt   3600
gggccgcctc cccgcctggc gatggtaccg gtgtggaaag tccccaggct ccccagcagg   3660
cagaagtatg caaagcatgc atctcaatta gtcagcaacc aggtgtggaa agtccccagg   3720
ctccccagca ggcagaagta tgcaaagcat gcatctcaat tagtcagcaa ccatagtccc   3780
gcccctaact ccgcccatcc cgcccctaac tccgccagt  tccgcccatt ctccgcccca   3840
tggctgacta ttttttttta tttatgcaga ggccgaggcc gcctctgcct ctgagctatt   3900
ccagaagtag tgaggaggct ttttggagg  cctaggcttt tgcaaaaagc tcccgggagc   3960
ttgtatatcc attttcggat ctgatcagca cgtgcacaat tcgagctcgg tacctttaag   4020
accaatgact tacaaggcag ctgtagatct tagccacttt ttaaaagaaa agggggact   4080 ggaagggcta attcactccc aacgaagaca agatctgctt tttgcttgta ctgggtctct   4140
ctggttagac cagatctgag cctgggagct ctctggctaa ctagggaacc cactgcttaa   4200
gcctcaataa agcttgcctt gagtgcttca agtagtgtgt gcccgtctgt tgtgtgactc   4260
tggtaactag agatccctca gacccttta  gtcagtgtgg aaaatctcta gcagtagtag   4320
ttcatgtcat cttattattc agtatttata acttgcaaag aaatgaatat cagagagtga   4380
gaggaacttg tttattgcag cttataatgg ttacaaataa agcaatagca tcacaaattt   4440
```
cacaaataaa gcattttttt cactgcacct aagg                                4474

<210> SEQ ID NO 11
<211> LENGTH: 3260
<212> TYPE: DNA
<213> ORGANISM: Artificial Sequence
<220> FEATURE:
<223> OTHER INFORMATION: Synthetic

<400> SEQUENCE: 11
agaccaggaa ttacatttgc ttctgacaca actgtgttca ctagcaacct caaacagagc    60
cgccatgggc ttttttaggg aagatctggc cttcccacaa gggaaggcca gggaattttc   120
ttcagagcag accagagcca acagccccac cagaagagag cttcaggttt ggggaagaga   180
caacaactcc ctctcagaag caggagccga tagacaagga actgtatcct ttagcttccc   240
tcagatcact ctttggcagc gaccectcgt cacaataaag ataggggggc agctcaagga   300
ggctctcctg gacaccggag cagacgacac cgtgctggag gagatgtcgt tgccaggccg   360
ctggaagccg aagatgatcg ggggaatcgg cggtttcatc aaggtgcgcc agtatgacca   420
gatcctcatc gaaatctgcg gccacaaggc tatcggtacc gtgctggtgg ccccacacc    480
cgtcaacatc atcggacgca acctgttgac gcagatcggt tgcacgctga acttccccat   540
tagccctatc gagacggtac cggtgaagct gaagcccggg atggacggcc gaaggtcaa    600
gcaatggcca ttgacagagg agaagatcaa ggcactggtg gagatttgca cagagatgga   660
aaaggaaggg aaaatctcca agattgggcc tgagaacccg tacaacacgc cggtgttcgc   720
aatcaagaag aaggactcga cgaaatggcg caagctggtg gacttccgcg agctgaacaa   780
gcgcacgcaa gacttctggg aggttcagct gggcatcccg caccccgcag ggctgaagaa   840
gaagaaatcc gtgaccgtac tggatgtggg tgatgcctac ttctccgttc cctggacga    900
agacttcagg aagtacactg cctcacaat cccttcgatc aacaacgaga caccggggat    960
tcgatatcag tacaacgtgc tgccccaggg ctggaaggc tctcccgcaa tcttccagag   1020
tagcatgacc aaaatcctgg agccttccg caaacagaac cccgacatcg tcatctatca   1080
gtacatggat gacttgtacg tgggctctga tctagagata gggcagcacc gcaccaagat   1140
cgaggagctg cgccagcacc tgttgaggtg gggactgacc acacccgaca agaagcacca   1200
gaaggagcct ccctccctct ggatgggtta cgagctgcac cctgacaaat ggaccgtgca   1260
gcctatcgtg ctgccagaga agacagctg gactgtcaac gacatacaga agctggtggg   1320
gaagttgaac tgggccagtc agatttaccc agggattaag gtgaggcagc tgtgcaaact   1380
cctccgcgga accaaggcac tcacagaggt gatcccccta accgaggagg ccgagctcga   1440
actggcagaa aaccgagaga tcctaaagga gcccgtgcac ggcgtgtact atgaccctc   1500
caaggacctg atcgccgaga tccagaagca ggggcaaggc cagtggacct atcagattta   1560
ccaggagccc ttcaagaacc tgaagaccgg caagtacgcc cggatgaggg gtgcccacac   1620
taacgacgtc aagcagctga ccgaggccgt gcagaagatc accaccgaaa gcatcgtgat   1680
ctggggaaag actcctaagt tcaagctgcc catccgaag gaaacctggg aaacctggtg   1740
gacagagtat tggcaggcca cctggattcc tgagtgggag ttcgtcaaca cccctcccct   1800
ggtgaagctg tggtaccagc tggagaagga gcccatagtg ggcgccgaaa ccttctacgt   1860
ggatgggcc gctaacaggg agactaagct gggcaaagcc ggatacgtca ctaaccgggg   1920
cagacagaag gttgtcaccc tcactgacac caccaaccag aagactgagc tgcaggccat   1980

| | |
|---|---|
| ttacctcgct ttgcaggact cgggcctgga ggtgaacatc gtgacagact ctcagtatgc | 2040 |
| cctgggcatc attcaagccc agccagacca gagtgagtcc gagctggtca atcagatcat | 2100 |
| cgagcagctg atcaagaagg aaaaggtcta tctggcctgg gtacccgccc acaaaggcat | 2160 |
| tggcggcaat gagcaggtcg acaagctggt ctcggctggc atcaggaagg tgctattcct | 2220 |
| ggatggcatc gacaaggccc aggacgagca cgagaaatac cacagcaact ggcgggccat | 2280 |
| ggctagcgac ttcaacctgc cccctgtggt ggccaaagag atcgtggcca gctgtgacaa | 2340 |
| gtgtcagctc aagggcgaag ccatgcatgg ccaggtggac tgtagccccg gcatctggca | 2400 |
| actcgattgc acccatctgg agggcaaggt tatcctggta gccgtccatg tggccagtgg | 2460 |
| ctacatcgag gccgaggtca ttcccgccga acagggcag gagacagcct acttcctcct | 2520 |
| gaagctggca ggccggtggc cagtgaagac catccatact gacaatggca gcaatttcac | 2580 |
| cagtgctacg gttaaggccg cctgctggtg ggcgggaatc aagcaggagt tcgggatccc | 2640 |
| ctacaatccc cagagtcagg gcgtcgtcga gtctatgaat aaggagttaa agaagattat | 2700 |
| cggccaggtc agagatcagg ctgagcatct caagaccgcg gtccaaatgg cggtattcat | 2760 |
| ccacaatttc aagcgaagg gggggattgg ggggtacagt gcggggagc ggatcgtgga | 2820 |
| catcatcgcg accgacatcc agactaagga gctgcaaaag cagattacca agattcagaa | 2880 |
| tttccgggtc tactacaggg acagcagaaa tccctctgg aaaggcccag cgaagctcct | 2940 |
| ctggaagggt gaggggcag tagtgatcca ggataatagc gacatcaagg tggtgcccag | 3000 |
| aagaaaggcg aagatcatta gggattatgg caaacagatg cgggtgatg attgcgtggc | 3060 |
| gagcagacag gatgaggatt agagctcgct ttcttgctgt ccaatttcta ttaaaggttc | 3120 |
| ctttgttccc taagtccaac tactaaactg ggggatatta tgaagggcct tgagcatctg | 3180 |
| gattctgcct aataagaaac atttattgtc attgcagaga cgcggccgcg cgtctcaatg | 3240 |
| aagagcgtcg acgcatgcgg | 3260 |

<210> SEQ ID NO 12
<211> LENGTH: 3212
<212> TYPE: DNA
<213> ORGANISM: Artificial Sequence
<220> FEATURE:
<223> OTHER INFORMATION: Synthetic

<400> SEQUENCE: 12

| | |
|---|---|
| agaccaggaa ttacatttgc ttctgacaca actgtgttca ctagcaacct caaacagagc | 60 |
| cgccatgttt tttagggaag atctggcctt cccacaaggg aaggcaggg aattttcttc | 120 |
| agagcagacc agagccaaca gccccaccag aagagagctt caggtttggg gaagagacaa | 180 |
| caactccctc tcagaagcag gagccgatag acaaggaact gtatccttta gcttccctca | 240 |
| gatcactctt tggcagcgac ccctcgtcac aataaagata gggggcaat taaggaagc | 300 |
| tctattagat acaggagcag atgatacagt attagaagaa atgaatttgc caggaagatg | 360 |
| gaaaccaaaa atgatagggg gaattggagg ttttatcaaa gtaagacagt atgatcagat | 420 |
| actcatagaa atctgcggac ataaagctat aggtacagta ttagtaggac ctacacctgt | 480 |
| caacataatt ggaagaaatc tgttgactca gattggctgc actttaaatt ttcccattag | 540 |
| tcctattgag actgtaccag taaaattaaa gccaggaatg gatggcccaa agttaaaaca | 600 |
| atggccattg acagaagaaa aaataaaagc attagtagaa atttgtacag aaatggaaaa | 660 |
| ggaaggaaaa atttcaaaaa ttgggcctga aaatccatac aatactccag tatttgccat | 720 |
| aaagaaaaaa gacagtacta atggagaaaa attagtagat ttcagagaac ttaataagag | 780 |

```
aactcaagat ttctgggaag ttcaattagg aataccacat cctgcagggt taaaacagaa      840
aaaatcagta acagtactgg atgtgggcga tgcatatttt tcagttccct tagataaaga      900
cttcaggaag tatactgcat ttaccatacc tagtataaac aatgagacac cagggattag      960
atatcagtac aatgtgcttc cacagggatg gaaaggatca ccagcaatat tccagtgtag     1020
catgacaaaa atcttagagc cttttagaaa acaaaatcca gacatagtca tctatcaata     1080
catggatgat ttgtatgtag gatctgactt agaaataggg cagcatagaa caaaaataga     1140
ggaactgaga caacatctgt tgaggtgggg atttaccaca ccagacaaaa aacatcagaa     1200
agaacctcca ttcctttgga tgggttatga actccatcct gataaatgga cagtacagcc     1260
tatagtgctg ccagaaaagg acagctggac tgtcaatgac atacagaaat tagtgggaaa     1320
attgaattgg gcaagtcaga tttatgcagg gattaaagta aggcaattat gtaaacttct     1380
taggggaacc aaagcactaa cagaagtagt accactaaca gaagaagcag agctagaact     1440
ggcagaaaac agggagattc taaaagaacc ggtacatgga gtgtattatg acccatcaaa     1500
agacttaata gcagaaatac agaagcaggg gcaaggccaa tggacatatc aaatttatca     1560
agagccattt aaaaatctga aaacaggaaa gtatgcaaga atgaagggtg cccacactaa     1620
tgatgtgaaa caattaacag aggcagtaca aaaaatagcc acagaaagca tagtaatatg     1680
gggaaagact cctaaattta aattacccat acaaaaggaa acatgggaag catggtggac     1740
agagtattgg caagccacct ggattcctga gtgggagttt gtcaataccc ctcccttagt     1800
gaagttatgg taccagttag agaaagaacc cataatagga gcagaaactt tctatgtaga     1860
tggggcagcc aatagggaaa ctaaattagg aaaagcagga tatgtaactg acagaggaag     1920
acaaaaagtt gtcccectaa cggacacaac aaatcagaag actgagttac aagcaattca     1980
tctagctttg caggattcgg gattagaagt aaacatagtg acagactcac aatatgcatt     2040
gggaatcatt caagcacaac cagataagag tgaatcagag ttagtcagtc aaataataga     2100
gcagttaata aaaaaggaaa agtctacctg gcatgggta ccagcacaca aaggaattgg     2160
aggaaatgaa caagtagata aattggtcag tgctggaatc aggaaagtac tatttttaga     2220
tggaatagat aaggcccaag aagaacatga gaaatatcac agtaattgga gagcaatggc     2280
tagtgatttt aacctaccac ctgtagtagc aaaagaaata gtagccagct gtgataaatg     2340
tcagctaaaa ggggaagcca tgcatggaca agtagactgt agcccaggaa tatggcagct     2400
agattgtaca catttagaag gaaaagttat cttggtagca gttcatgtag ccagtggata     2460
tatagaagca gaagtaattc cagcagagac agggcaagaa acagcatact tcctcttaaa     2520
attagcagga agatggccag taaaaacagt acatacagac aatggcagca atttcaccag     2580
tactacagtt aaggccgcct gttggtgggc ggggatcaag caggaatttg gcattcccta     2640
caatccccaa agtcaaggag taatagaatc tatgaataaa gaattaaaga aaattatagg     2700
acaggtaaga gatcaggctg aacatcttaa gacagcagta caaatggcag tattcatcca     2760
caatttaaaa agaaaagggg ggattggggg gtacagtgca ggggaaagaa tagtagacat     2820
aatagcaaca gacatacaaa ctaaagaatt acaaaaacaa attacaaaaa ttcaaaattt     2880
tcgggtttat tacagggaca gcagagatcc agtttggaaa ggaccagcaa agctcctctg     2940
gaaaggtgaa ggggcagtag taatacaaga taatagtgac ataaaagtag tgccaagaag     3000
aaaagcaaag atcatcaggg attatggaaa acagatggca ggtgatgatt gtgtggcaag     3060
tagacaggat gaggattaaa gctcgctttc ttgctgtcca atttctatta aaggttcctt     3120
```

```
tgttccctaa gtccaactac taaactgggg gatattatga agggccttga gcatctggat    3180
tctgcctaat aagaaacatt tattgtcatt gc                                  3212

<210> SEQ ID NO 13
<211> LENGTH: 1115
<212> TYPE: DNA
<213> ORGANISM: Artificial Sequence
<220> FEATURE:
<223> OTHER INFORMATION: Synthetic

<400> SEQUENCE: 13
agaccaggaa ttacatttgc ttctgacaca actgtgttca ctagcaacct caaacagagc      60
cgccatggga ttcctggacg gcattgacaa ggctcaggag gagcacgaga agtaccactc     120
gaattggcgg gccatggcct ccgacttcaa cctgccaccc gtcgtcgcta aggagatcgt     180
tgctagctgc gacaagtgcc agctgaaagg cgaggctatg cacgggcagg ttgattgctc     240
tcccggcatc tggcagctcg actgtactca cctggagggc aaggtcatcc tggtcgccgt     300
gcacgtggcc tctggttaca tcgaggctga ggtcatccct gcagagactg gccaggagac     360
tgcctatttc ctgctgaaac tggccggccg gtggcctgtg aagacagtgc acacagataa     420
cggctccaac ttcacctcca ccactgtgaa ggctgcctgc tggtgggctg ggatcaagca     480
ggagttcggg atcccctata acccacagtc tcagggcgtg atcgaatcca tgaacaagga     540
gctgaagaag atcatcggcc aggttccgga ccaggcagag cacctgaaga ctgcagtgca     600
catggccgtg ttcatccaca acttcaagcg aaagggcgcc atcggtgcct actcagccgg     660
cgagcggatc gtggacatca tcgccactga catccagacc aaagagctgc agaagcagat     720
caccaagatc cagaacttcc gtgtgtacta ccgggactcc cgggaccctg tgtggaaggg     780
ccctgccaag ctgctgtgga agggcgaggg cgccgtggtc attcaggaca actgtgacat     840
caaggttgtg cccaggcgca aggccaagat tatccgggac tacggcaagc agatggctgg     900
cgacgactgt gtggcctctc gtcaagatga ggactaaagc tcgctttctt gctgtccaat     960
ttctattaaa ggttcctttg ttccctaagt ccaactacta aactgggggga tattatgaag    1020 ggccttgagc atctggattc tgcctaataa gaaacattta ttgtcattgc agagacgcgg    1080
ccgcgcgtct caatgaagag cgtcgacgca tgcgg                                1115

<210> SEQ ID NO 14
<211> LENGTH: 1115
<212> TYPE: DNA
<213> ORGANISM: Artificial Sequence
<220> FEATURE:
<223> OTHER INFORMATION: Synthetic

<400> SEQUENCE: 14
agaccaggaa ttacatttgc ttctgacaca actgtgttca ctagcaacct caaacagagc      60
cgccatggga ttccttgacg gcatcgacaa ggcgcaagag gagcacgaga atatccatag     120
caactggagg gcgatggcat cagacttcaa cttgccgcca gtcgtggcta agagatagt      180 agcaagctgc gataagtgtc aactgaaggg tgaagcgatg cacggtcaag tggactgttc     240
ccctggtata tggcaactgg actgtaccca tctcgaaggt aaagtcattt tggttgctgt     300
acatgttgcc tctgggtata tcgaggctga ggtgattcca gcagaaacgg gacaggaaac     360
agcttatttc ttgctcaagc ttgccggag atggcctgtg aaaactgttc atacagataa      420
tggtagcaat tttactagta cgaccgtgaa agcagcttgt tggtgggcag ggattaagca     480
agaattcgga atcccgtata acccgcagag tcagggcgtt attgagagca tgaacaagga     540
```

```
actgaaaaaa ataattgggc aagtgagaga tcaggctgag catcttaaaa ctgctgtaca    600
aatggcggtg ttcatacata attttaagcg gaagggagga attggaggat actctgcggg    660
agagaggata gtggatataa tagcgaccga tattcagaca aaggagctgc aaaaacagat    720
aacgaaaata caaaatttc gagtttacta tcgggactcc cgcgatcccg tgtggaaagg     780
tccagcgaaa ttgctttgga agggcgaagg cgcggtagtg atccaggaca attctgatat    840
caaagtggtc ccaaggcgga aagcaaagat aatccgcgac tacggcaagc aaatggcagg    900
agatgattgc gtcgcatcac gacaggacga agattaaagc tcgctttctt gctgtccaat    960
ttctattaaa ggttcctttg ttccctaagt ccaactacta aactggggga tattatgaag   1020
ggccttgagc atctggattc tgcctaataa gaaacattta ttgtcattgc agagacgcgg   1080
ccgcgcgtct caatgaagag cgtcgacgca tgcgg                              1115
```

<210> SEQ ID NO 15
<211> LENGTH: 1067
<212> TYPE: DNA
<213> ORGANISM: Artificial Sequence
<220> FEATURE:
<223> OTHER INFORMATION: Synthetic

<400> SEQUENCE: 15

```
agaccaggaa ttacatttgc ttctgacaca actgtgttca ctagcaacct caaacagagc     60
cgccatgttt ttagatggaa tagataaggc ccaagaagaa catgagaaat atcacagtaa    120
ttggagagca atggctagtg attttaacct accacctgta gtagcaaaag aaatagtagc    180
cagctgtgat aaatgtcagc taaaagggga agccatgcat ggacaagtag actgtagccc    240
aggaatatgg cagctagatt gtacacattt agaaggaaaa gttatcttgg tagcagttca    300
tgtagccagt ggatatatag aagcagaagt aattccagca gagacagggc aagaaacagc    360
atacttcctc ttaaaattag caggaagatg gccagtaaaa acagtacata gacaatggc    420 cagcaatttc accagtacta cagttaaggc cgcctgttgg tgggcgggga tcaagcagga    480
atttggcatt ccctacaatc cccaaagtca aggagtaata gaatctatga ataaagaatt    540
aaagaaaatt ataggacagg taagagatca ggctgaacat cttaagacag cagtacaaat    600
ggcagtattc atccacaatt ttaaaagaaa aggggggatt ggggggtaca gtgcagggga    660
aagaatagta gacataatag caacagacat acaaactaaa gaattacaaa aacaaattac    720
aaaaattcaa aattttcggg tttattacag ggacagcaga gatccagttt ggaaaggacc    780
agcaaagctc ctctggaaag gtgaaggggc agtagtaata caagataata gtgacataaa    840
agtagtgcca agaagaaaag caaagatcat cagggattat ggaaaacaga tggcaggtga    900
tgattgtgtg gcaagtagac aggatgagga ttaaagctcg ctttcttgct gtccaatttc    960
tattaaaggt tcctttgttc cctaagtcca actactaaac tgggggatat tatgaagggc   1020
cttgagcatc tggattctgc ctaataagaa acatttattg tcattgc                 1067
```

<210> SEQ ID NO 16
<211> LENGTH: 1568
<212> TYPE: DNA
<213> ORGANISM: Artificial Sequence
<220> FEATURE:
<223> OTHER INFORMATION: Synthetic

<400> SEQUENCE: 16

```
agaccaggaa ttacatttgc ttctgacaca actgtgttca ctagcaacct caaacagagc     60
```

| | |
|---|---|
| cgccatgccc attagcccta tcgagacggt accggtgaag ctgaagcccg ggatggacgg | 120 |
| cccgaaggtc aagcaatggc cattgacaga ggagaagatc aaggcactgg tggagatttg | 180 |
| cacagagatg gaaaaggaag ggaaaatctc caagattggg cctgagaacc cgtacaacac | 240 |
| gccggtgttc gcaatcaaga agaaggactc gacgaaatgg cgcaagctgg tggacttccg | 300 |
| cgagctgaac aagcgcacgc aagacttctg ggaggttcag ctgggcatcc cgcacccgc | 360 |
| agggctgaag aagaagaaat ccgtgaccgt actggatgtg ggtgatgcct acttctccgt | 420 |
| tccccctggac gaagacttca ggaagtacac tgccttcaca atcccttcga tcaacaacga | 480 |
| gacaccgggg attcgatatc agtacaacgt gctgccccag ggctggaaag gctctcccgc | 540 |
| aatcttccag agtagcatga ccaaaatcct ggagcctttc cgcaaacaga ccccgacat | 600 |
| cgtcatctat cagtacatgg atgacttgta cgtgggctct gatctagaga tagggcagca | 660 |
| ccgcaccaag atcgaggagc tgcgccagca cctgttgagg tggggactga ccacacccga | 720 |
| caagaagcac cagaaggagc tccccttcct ctggatgggt tacgagctgc accctgacaa | 780 |
| atggaccgtg cagcctatcg tgctgccaga gaaagacagc tggactgtca acgacataca | 840 |
| gaagctggtg gggaagttga actgggccag tcagatttac ccagggatta aggtgaggca | 900 |
| gctgtgcaaa ctcctccgcg gaaccaaggc actcacagag tgatcccc taaccgagga | 960 |
| ggccgagctc gaactggcag aaaaccgaga gatcctaaag gagcccgtgc acggcgtgta | 1020 |
| ctatgacccc tccaaggacc tgatcgccga gatccagaag caggggcaag gccagtggac | 1080 |
| ctatcagatt taccaggagc ccttcaagaa cctgaagacc ggcaagtacg cccggatgag | 1140 |
| gggtgcccac actaacgacg tcaagcagct gaccgaggcc gtgcagaaga tcaccaccga | 1200 |
| aagcatcgtg atctggggaa agactcctaa gttcaagctg cccatccaga aggaaacctg | 1260 |
| ggaaacctgg tggacagagt attggcaggc cacctggatt cctgagtggg agttcgtcaa | 1320 |
| caccccctccc ctggtgaagc tgtggtacca gctggagaag gagcccatag tgggcgccga | 1380 |
| aaccttctaa agctcgcttt cttgctgtcc aatttctatt aaaggttcct ttgttcccta | 1440 |
| agtccaacta ctaaactggg ggatattatg aagggccttg agcatctgga ttctgcctaa | 1500 |
| taagaaacat ttattgtcat tgcagagacg cggccgcgcg tctcaatgaa gagcgtcgac | 1560 |
| gcatgcgg | 1568 |

<210> SEQ ID NO 17
<211> LENGTH: 1928
<212> TYPE: DNA
<213> ORGANISM: Artificial Sequence
<220> FEATURE:
<223> OTHER INFORMATION: Synthetic

<400> SEQUENCE: 17

| | |
|---|---|
| agaccaggaa ttacatttgc ttctgacaca actgtgttca ctagcaacct caaacagagc | 60 |
| cgccatgccc attagcccta tcgagacggt accggtgaag ctgaagcccg ggatggacgg | 120 |
| cccgaaggtc aagcaatggc cattgacaga ggagaagatc aaggcactgg tggagatttg | 180 |
| cacagagatg gaaaaggaag ggaaaatctc caagattggg cctgagaacc cgtacaacac | 240 |
| gccggtgttc gcaatcaaga agaaggactc gacgaaatgg cgcaagctgg tggacttccg | 300 |
| cgagctgaac aagcgcacgc aagacttctg ggaggttcag ctgggcatcc cgcacccgc | 360 |
| agggctgaag aagaagaaat ccgtgaccgt actggatgtg ggtgatgcct acttctccgt | 420 |
| tccccctggac gaagacttca ggaagtacac tgccttcaca atcccttcga tcaacaacga | 480 |
| gacaccgggg attcgatatc agtacaacgt gctgccccag ggctggaaag gctctcccgc | 540 |

```
aatcttccag agtagcatga ccaaaatcct ggagcctttc cgcaaacaga accccgacat      600
cgtcatctat cagtacatgg atgacttgta cgtgggctct gatctagaga tagggcagca      660
ccgcaccaag atcgaggagc tgcgccagca cctgttgagg tggggactga ccacacccga      720
caagaagcac cagaaggagc ctcccttcct ctggatgggt tacgagctgc accctgacaa      780
atggaccgtg cagcctatcg tgctgccaga gaaagacagc tggactgtca acgacataca      840
gaagctggtg gggaagttga actgggccag tcagatttac ccagggatta aggtgaggca      900
gctgtgcaaa ctcctccgcg gaaccaaggc actcacagag gtgatccccc taaccgagga      960
ggccgagctc gaactggcag aaaaccgaga gatcctaaag gagcccgtgc acggcgtgta     1020
ctatgacccc tccaaggacc tgatcgccga gatccagaag caggggcaag gccagtggac     1080
ctatcagatt taccaggagc ccttcaagaa cctgaagacc ggcaagtacg cccggatgag     1140
gggtgcccac actaacgacg tcaagcagct gaccgaggcc gtgcagaaga tcaccaccga     1200
aagcatcgtg atctggggaa agactcctaa gttcaagctg cccatccaga aggaaacctg     1260
ggaaacctgg tggacagagt attggcaggc cacctggatt cctgagtggg agttcgtcaa     1320 caccccctccc ctggtgaagc tgtggtacca gctggagaag gagcccatag tgggcgccga     1380
aaccttctac gtggatgggg ccgctaacag ggagactaag ctgggcaaag ccggatacgt     1440
cactaaccgg ggcagacaga aggttgtcac cctcactgac accaccaacc agaagactga     1500
gctgcaggcc atttacctcg ctttgcagga ctcgggcctg gaggtgaaca tcgtgacaga     1560
ctctcagtat gccctgggca tcattcaagc ccagccagac cagagtgagt ccgagctggt     1620
caatcagatc atcgagcagc tgatcaagaa ggaaaaggtc tatctggcct gggtacccgc     1680
ccacaaaggc attggcggca atgagcaggt cgacaagctg gtctcggctg gcatcaggaa     1740
ggtgctataa agctcgcttt cttgctgtcc aatttctatt aaaggttcct tgttcccta      1800 agtccaacta ctaaactggg ggatattatg aagggccttg agcatctgga ttctgcctaa     1860
taagaaacat ttattgtcat tgcagagacg cggccgcgcg tctcaatgaa gagcgtcgac     1920
gcatgcgg                                                              1928

<210> SEQ ID NO 18
<211> LENGTH: 18
<212> TYPE: RNA
<213> ORGANISM: Artificial Sequence
<220> FEATURE:
<223> OTHER INFORMATION: Synthetic

<400> SEQUENCE: 18
gucccuguuc gggcgcca                                                     18

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
gtccctgttc gggcgcca                                                     18
```